(12) United States Patent
Hayashi et al.

(10) Patent No.: US 6,620,593 B1
(45) Date of Patent: *Sep. 16, 2003

(54) METHOD FOR SAFETY EVALUATION OF CHEMICAL COMPOUND USING RECOMBINANT YEAST EXPRESSING HUMAN CYTOCHROME P450

(75) Inventors: Koji Hayashi, Takarazuka (JP); Toshiyuki Sakaki, Toyonaka (JP); Yoshiyasu Yabusaki, Kobe (JP); Koichiro Komai, Mino (JP); Hideo Kaneko, Kyoto (JP); Iwao Nakatsuka, Kobe (JP)

(73) Assignee: Sumitomo Chemical Company, Limited, Osaka-fu (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/277,031

(22) Filed: Jul. 19, 1994

(30) Foreign Application Priority Data

Jul. 20, 1993 (JP) .............................. 5-201120
Jul. 21, 1993 (JP) .............................. 5-180246
Jul. 30, 1993 (JP) .............................. 5-208279

(51) Int. Cl.[7] .............................. C12Q 1/26; C12Q 1/02; C12N 15/53; C12N 15/81
(52) U.S. Cl. ........................ 435/25; 435/29; 435/69.1; 435/69.7; 435/189; 435/254.21; 435/320.1; 536/23.2; 536/23.4
(58) Field of Search .............................. 435/69.1, 69.7, 435/189, 254.21, 320.1, 25, 29, 67.7; 536/23.2, 23.4

(56) References Cited

U.S. PATENT DOCUMENTS 5,114,852 A * 5/1992 Yabusaki et al. ............ 435/189
5,356,806 A * 10/1994 Harris et al. ............. 435/240.2
5,429,948 A * 7/1995 Crespi et al. ............. 435/240.2
5,506,131 A * 4/1996 Harris et al. ............. 435/240.2
5,525,482 A * 6/1996 States et al. .................. 435/32
5,660,986 A * 8/1997 Harris et al. .................... 435/6

FOREIGN PATENT DOCUMENTS

EP  0273771  7/1988
EP  9308260  4/1993
WO  9207085  4/1992
WO  9214817  9/1992

OTHER PUBLICATIONS

Murakami, H., et al., DNA, vol. 6, "A genetically engineered P450 monooxygenase: Construction of the functional fused enzyme between rat cytochrome P450c and NADPH–cytochrome P450 reductase", pp. 189–197, 1987.*

Yasumori, T., et al., Journal of Biochemistry, vol. 102, "Nucleotide sequence of a human liver cytochrome P–450 related to the rat male specific form", pp. 1075–1082, 1987.*

Yabusaki, Y., et al., Journal of Biochemistry, vol. 103, "Primary structure of Saccharomyces cerevisiae NADPH–cytochrome P450 reductase deduced from nucleotide sequence of its cloned gene", pp. 1004–1010, 1988.*

Sakaki, T., et al., DNA and Cell Biology, vol. 9, "Expression of bovine cytochrome P450c21 and its fused enzymes with yeast NADPH–cytochrome P450 reductase in Saccharomyces cerevisiae", pp. 603–614, 1990.*

Paolini, M., et al., Carcinogenesis, vol. 12, "Wide spectrum detection of precarcinogens in short–term bioassays by simultaneous superinductin of multiple forms of cytochrome P450 isoenzymes", pp. 759–766, 1991.*

Ellis et al., Biochemical Pharmacology 44:617–620 (1992).

Eugster et al., Biochemcial and Biophysical Research Communications, 172:737–744, (1990).

Bligh et al., Gene, 100:33–39, (1992).

Renaud et al., Eur. J. Biochem., 194:889–896 (1990).

Yasumori et al., Molecular Pharmacology, 35:443–449 (1989).

Daniel W. Nebert et al., *DNA*, vol. 8, No. 1, pp. 1–13 (1989).

Database WPI, Section Ch., Week 9046, Derwent Publ., Ltd., London, GB, XP002002550 & JP–A–02 249 488, Oct. 1990 (Abstract).

Database WPI, Section Ch., Week 9010, Derwent Pub., Ltd., London, GB; XP002002551 & JP–A–02 023 870, Jan. 1990 (Abstract).

* cited by examiner

*Primary Examiner*—Nashaat T. Nashed
*Assistant Examiner*—William W. Moore
(74) *Attorney, Agent, or Firm*—Birch, Stewart, Kolasch & Birch, LLP

(57) ABSTRACT

There is disclosed a method for evaluation of the safety of a chemical compound, which includes the steps of: (a) reacting a chemical compound with recombinant yeast cells expressing, or in other words producing, human cytochrome P450 molecular species P450 1A2, P450 2C9, P450 2E1 and P450 3A4 together with a yeast NADPH-P450 reductase, which may be in the form of a fused enzyme with each of said human cytochrome P450 molecular species, or with the cell free extracts of the yeast cells; and (b) analyzing the resulting metabolite to determine the safety of the compound. According to this method, it can be determined whether a test compound will be converted into a carcinogenic or mutagenic form through the metabolism in the human liver, and whether the test compound or its metabolite has mutagenicity.

14 Claims, 18 Drawing Sheets

| | | |
|---|---|---|
| 1A2 | 5'-CACAGAGCTCCTCCTGGCCTCTGCCATCTTC-3'<br>5'-TTACAGGCCCTGCACTTGGCTAAAGCTGC-3' | PRIMER FOR AMPLIFYING<br>P4501A2 1.5Kb FRAGMENT |
| 2C9 | 5'-AGTCTAGAATGGATTCTATTGTGTCCCTTGTGCTC-3'<br>5'-CTCCAAACAAGTCAACTGCAGTGTTTCCAAGC-3' | PRIMER FOR AMPLIFYING<br>P4502C9 0.9Kb FRAGMENT |
| | 5'-GCTTGGAAAACACTGCAGTTGACTTGTTTGGAG-3'<br>5'-ACTGAGCAGCAGGCCAGGCCATCTGCTCTTC-3' | PRIMER FOR AMPLIFYING<br>P4502C9 0.6Kb FRAGMENT |
| 2E1 | 5'-CCCCAGAATTCAATGTCTGCCCTCGGAGTG-3'<br>5'-CCTCTGGATCCGGCTCTCATTGCCCTGTTTC-3' | PRIMER FOR AMPLIFYING<br>P4502E1 0.5Kb FRAGMENT |
| | 5'-GAAACAGGGCAATGAGAGCCGGATCCAGAGG-3'<br>5'-GAAAACTTGTTTGCATGCGGGGGGTTCAGG-3' | PRIMER FOR AMPLIFYING<br>P4502E1 1.0Kb FRAGMENT |

FIG.1

| | | |
|---|---|---|
| 3A4 | 5'-AGTAAGGAATCTAGAAATGGCTCTCATCCCAG-3'<br>5'-ACGAGCTCCAGATCGGACAGAGCTTTG-3' | PRIMER FOR AMPLIFYING<br>P4503A4 0.6Kb FRAGMENT |
| | 5'-CAAAGCTCTGTCCGATCTGGAGCTCGT-3'<br>5'-CAAAGTAATTTGAGGTACCTGGTGTTCTCAGGC-3' | PRIMER FOR AMPLIFYING<br>P4503A4 0.9Kb FRAGMENT |
| 1A1 | 5'-CCTCTAGAAATGCTTTTCCCAATCTCCATG-3'<br>5'-CCAATCACTGTGTCGAGCTCCTCTTGGATC-3' | PRIMER FOR AMPLIFYING<br>P4501A1 1.0Kb FRAGMENT |
| | 5'-GATCCAAGAGGAGCTCGACACAGTGATTGG-3'<br>5'-GGGCTCTCAAGCACCTAAGAGCGCAGCTGC-3' | PRIMER FOR AMPLIFYING<br>P4501A1 0.5Kb FRAGMENT |
| 2A6 | 5'-GCTTCTAGAATGCTGGCCTCAGGGATGCTTC-3'<br>5'-CGTGGAGGTTGACGTGAACTGGAAGATTC-3' | PRIMER FOR AMPLIFYING<br>P4502A6 0.6Kb FRAGMENT |
| | 5'-GAATCTTCCAGTTCACGTCAACCTCCACG-3'<br>5'-AGACCTGGTACCGCACACAGCCCTCGCTCAG-3' | PRIMER FOR AMPLIFYING<br>P4502A6 0.9Kb FRAGMENT |

FIG.2

| | | |
|---|---|---|
| 2B6 | 5'-CCTCTAGAAAATGGAACTCAGGCGTCCTCCT-3'<br>5'-GGGGATCCTGAATGACCCCTGGAATCCTTTG-3' | PRIMER FOR AMPLIFYING<br>P4502B6 1.56Kb FRAGMENT |
| 2C8 | 5'-GAAGAGAAGTCTAGAATGGAACCTTTTGTGGTCC-3'<br>5'-ATAGCAGATCGGCAGCCAGATGGGCTAGCATTC-3' | PRIMER FOR AMPLIFYING<br>P4502C8 1.5Kb FRAGMENT |
| 2C18 | 5'-AGTCTAGAATGGTACCAGCTGTGGCTCTGG-3'<br>5'-CCCCAAACATATCAGTTACAGTGGCTATCAAGC-3' | PRIMER FOR AMPLIFYING<br>P4502C18 0.9Kb FRAGMENT |
| | 5'-CCCGATTATTGGAAAATATCCTGCAGTTAGATG-3'<br>5'-ACAGCACAGGAGCAGCCAAACTATCTGCC-3' | PRIMER FOR AMPLIFYING<br>P4502C18 1.4Kb FRAGMENT |

FIG.3

2C19  THE SEQUENCE SHOWN BY 5'-...-3' IS DESCRIBED IN SEQ
      ID NOS: 20 TO 40.

2D6   5'-TGTTCAGCCTGCAGCTGGCCTGGAC-3'          PRIMER FOR AMPLIFYING
      5'-AAGCGAGGGTCGTCGTATTCGAAGCG-3'         P4502D6 0.4Kb FRAGMENT

5'-GCTTCGAATACGACGACCCTGCTTCCTC-3'       PRIMER FOR AMPLIFYING
      5'-ACTAGGTACCCCATTCTAGCGGGGCACAG-3'      P4502D6 0.9Kb FRAGMENT

3A4   (AN ARTIFICIAL FUSED ENZYME)             PRIMER FOR AMPLIFYING
                                               P4503A4 XbaI-XhoI FRAGMENT
      5'-AATCTAGAGAAATGGCTCTCTCATCCCAG-3'
      5'-AGGACTCGAGCGGCTCCACTTACGGTGCCATCCC-3'

FIG.4

(1) LINKER FOR CLONING 1A2

5'-AGCTTAAAAAAATGGCATTGTCCCAGTCTGTTCCCTTCTCGGCCACAGAGCT-3'
3'-    ATTTTTTACCGTAACAGGGTCAGACAAGGGAAGAGCCGGTGTC    -5'

(2) LINKER FOR CLONING 2D6

5'-CTAGATATGGGGCTAGAAGCACTGGTGCCCTGGCCGTGATAGTGG-3'
3'-    TATACCCGATCTTCGTGACCACGGGGACCGGCACTATCACC-5'

5'-CCATCTTCCTGCTCCTGGTGGACCTGATGCACCGGCGCCAACGCTGGGCGCCCAAGCTGGGCGCCGGGTTGCGACCCGAGTCGTGGCCGCGGGTTGCGACCGGTTGCGATGGGTGGTCCGGGGGACGGTGACGGGGCCCG    -5'
3'-GGTAGAAGGACGAGGACCACCTGGACTACGTGGCCGCGGTTGCGACCCGCGGCCCAACGCTGCCGACCCGCGGCCCAAGCTGGGGCGCCGCTTCGGGGACGTGTTCAGCCTGCA-3'

5'-GGGCTGGGCAACCTGCTGCATGTGGACTTCCAGAACACACCATACTGCTTCGACCAGTTGCGGGCGCCGCTTCGGGGACGTGTTCAGCCTGCA-3'
3'-CCCGACCCGTTGGACGACGTACACCTGAAGGTCTTGTGTGGTATGACGAAGCTGGTCAACGCCGGCGGCGAAGCCCCTGCACAAGTCGG    -5'

FIG.5

SEQUENCE LISTING (1) GENERAL INFORMATION:

(iii) NUMBER OF SEQUENCES: 42

(2) INFORMATION FOR SEQ ID NO: 1:

(i) SEQUENCE CHARACTERISTICS:
      (A) LENGTH: 1551
      (B) TYPE: nucleic acid
      (C) STRANDEDNESS: double
      (D) TOPOLOGY: linear (ii) SEQUENCE DESCRIPTION: SEQ ID NO: 1:

```
ATG GCA TTG TCC CAG TCT GTT CCC TTC TCG GCC ACA GAG CTC CTC            45
Met Ala Leu Ser Gln Ser Val Pro Phe Ser Ala Thr Glu Leu Leu
 1               5                  10                  15

CTG GCC TCT GCC ATC TTC TGC CTG GTA TTC TGG GTG CTC AAG GGT            90
Leu Ala Ser Ala Ile Phe Cys Leu Val Phe Trp Val Leu Lys Gly
                20                  25                  30

TTG AGG CCT CGG GTC CCC AAA GGC CTG AAA AGT CCA CCA GAG CCA           135
Leu Arg Pro Arg Val Pro Lys Gly Leu Lys Ser Pro Pro Glu Pro
                35                  40                  45

TGG GGC TGG CCC TTG CTC GGG CAT GTG CTG ACC CTG GGG AAG AAC           180
Trp Gly Trp Pro Leu Leu Gly His Val Leu Thr Leu Gly Lys Asn
                50                  55                  60

CCG CAC CTG GCA CTG TCA AGG ATG AGC CAG CGC TAC GGG GAC GTC           225
Pro His Leu Ala Leu Ser Arg Met Ser Gln Arg Tyr Gly Asp Val
                65                  70                  75

CTG CAG ATC CGC ATT GGC TCC ACG CCC GTG CTG GTG CTG AGC CGC           270
Leu Gln Ile Arg Ile Gly Ser Thr Pro Val Leu Val Leu Ser Arg
                80                  85                  90

CTG GAC ACC ATC CGG CAG GCC CTG GTG CGG CAG GGC GAC GAT TTC           315
Leu Asp Thr Ile Arg Gln Ala Leu Val Arg Gln Gly Asp Asp Phe
```

-continued

```
                          95                  100                 105
AAG GGC CGG CCT GAC CTC TAC ACC TCC ACC CTC ATC ACT GAT GGC                    360
Lys Gly Arg Pro Asp Leu Tyr Thr Ser Thr Leu Ile Thr Asp Gly
                110                 115                 120

CAG AGC TTG ACC TTC AGC ACA GAC TCT GGA CCG GTG TGG GCT GCC                    405
Gln Ser Leu Thr Phe Ser Thr Asp Ser Gly Pro Val Trp Ala Ala
                125                 130                 135

CGC CGG CGC CTG GCC CAG AAT GCC CTC AAC ACC TTC TCC ATC GCC                    450
Arg Arg Arg Leu Ala Gln Asn Ala Leu Asn Thr Phe Ser Ile Ala
                140                 145                 150

TCT GAC CCA GCT TCC TCA TCC TCC TGC TAC CTG GAG GAG CAT GTG                    495
Ser Asp Pro Ala Ser Ser Ser Ser Cys Tyr Leu Glu Glu His Val
                155                 160                 165

AGC AAG GAG GCT AAG GCC CTG ATC AGC AGG TTG CAG GAG CTG ATG                    540
Ser Lys Glu Ala Lys Ala Leu Ile Ser Arg Leu Gln Glu Leu Met
                170                 175                 180

GCA GGG CCT GGG CAC TTC GAC CCT TAC AAT CAG GTG GTG GTG TCA                    585
Ala Gly Pro Gly His Phe Asp Pro Tyr Asn Gln Val Val Val Ser
                185                 190                 195

GTG GCC AAC GTC ATT GGT GCC ATG TGC TTC GGA CAG CAC TTC CCT                    630
Val Ala Asn Val Ile Gly Ala Met Cys Phe Gly Gln His Phe Pro
                200                 205                 210

GAG AGT AGC GAT GAG ATG CTC AGC CTC GTG AAG AAC ACT CAT GAG                    675
Glu Ser Ser Asp Glu Met Leu Ser Leu Val Lys Asn Thr His Glu
                215                 220                 225

TTC GTG GAG ACT GCC TCC TCC GGG AAC CCC CTG GAC TTC TTC CCC                    720
Phe Val Glu Thr Ala Ser Ser Gly Asn Pro Leu Asp Phe Phe Pro
                230                 235                 240

ATC CTT CGC TAC CTG CCT AAC CCT GCC CTG CAG AGG TTC AAG GCC                    765
Ile Leu Arg Tyr Leu Pro Asn Pro Ala Leu Gln Arg Phe Lys Ala
                245                 250                 255

TTC AAC CAG AGG TTC CTG TGG TTC CTG CAG AAA ACA GTC CAG GAG                    810
Phe Asn Gln Arg Phe Leu Trp Phe Leu Gln Lys Thr Val Gln Glu
                260                 265                 270

CAC TAT CAG GAC TTT GAC AAG AAC AGT GTC CGG GAC ATC ACG GGT                    855
His Tyr Gln Asp Phe Asp Lys Asn Ser Val Arg Asp Ile Thr Gly
                275                 280                 285

GCC CTG TTC AAG CAC AGC AAG AAG GGG CCT AGA GCC AGC GGC AAC                    900
Ala Leu Phe Lys His Ser Lys Lys Gly Pro Arg Ala Ser Gly Asn
                290                 295                 300

CTC ATC CCA CAG GAG AAG ATT GTC AAC CTT GTC AAT GAC ATC TTT                    945
Leu Ile Pro Gln Glu Lys Ile Val Asn Leu Val Asn Asp Ile Phe
                305                 310                 315

GGA GCA GGA TTT GAC ACA GTC ACC ACA GCC ATC TCC TGG AGC CTC                    990
Gly Ala Gly Phe Asp Thr Val Thr Thr Ala Ile Ser Trp Ser Leu
                320                 325                 330

ATG TAC CTT GTG ACC AAG CCT GAG ATA CAG AGG AAG ATC CAG AAG                   1035
Met Tyr Leu Val Thr Lys Pro Glu Ile Gln Arg Lys Ile Gln Lys
                335                 340                 345

GAG CTG GAC ACT GTG ATT GGC AGG GAG CGG CGG CCC CGG CTC TCT                   1080
Glu Leu Asp Thr Val Ile Gly Arg Glu Arg Arg Pro Arg Leu Ser
                350                 355                 360

GAC AGA CCC CAG CTG CCC TAC TTG GAG GCC TTC ATC CTG GAG ACC                   1125
Asp Arg Pro Gln Leu Pro Tyr Leu Glu Ala Phe Ile Leu Glu Thr
                365                 370                 375

TTC CGA CAC TCC TCC TTC TTG CCC TTC ACC ATC CCC CAC AGC ACA                   1170
Phe Arg His Ser Ser Phe Leu Pro Phe Thr Ile Pro His Ser Thr
                380                 385                 390

ACA AGG GAC ACA ACG CTG AAT GGC TTC TAC ATC CCC AAG AAA TGC                   1215
```

```
Thr Arg Asp Thr Thr Leu Asn Gly Phe Tyr Ile Pro Lys Lys Cys
                395                 400                 405

TGT GTC TTC GTA AAC CAG TGG CAG GTC AAC CAT GAC CCA GAG CTG          1260
Cys Val Phe Val Asn Gln Trp Gln Val Asn His Asp Pro Glu Leu
                410                 415                 420

TGG GAG GAC CCC TCT GAG TTC CGG CCT GAG CGG TTC CTC ACC GCC          1305
Trp Glu Asp Pro Ser Glu Phe Arg Pro Glu Arg Phe Leu Thr Ala
                425                 430                 435

GAT GGC ACT GCC ATT AAC AAG CCC TTG AGT GAG AAG ATG ATG CTG          1350
Asp Gly Thr Ala Ile Asn Lys Pro Leu Ser Glu Lys Met Met Leu
                440                 445                 450

TTT GGC ATG GGT AAG CGC CGG TGT ATC GGG GAA GTC CTG GCC AAG          1395
Phe Gly Met Gly Lys Arg Arg Cys Ile Gly Glu Val Leu Ala Lys
                455                 460                 465

TGG GAG ATC TTC CTC TTC CTG GCC ATC CTG CTA CAG CAA CTG GAG          1440
Trp Glu Ile Phe Leu Phe Leu Ala Ile Leu Leu Gln Gln Leu Glu
                470                 475                 480

TTC AGC GTG CCG CCG GGC GTG AAA GTC GAC CTG ACC CCC ATC TAC          1485
Phe Ser Val Pro Pro Gly Val Lys Val Asp Leu Thr Pro Ile Tyr
                485                 490                 495

GGG CTG ACC ATG AAG CAC GCC CGC TGT GAA CAT GTC CAG GCG CGG          1530
Gly Leu Thr Met Lys His Ala Arg Cys Glu His Val Gln Ala Arg
                500                 505                 510

CTG CGC TTC TCC ATC AAC TGA                                          1551
Leu Arg Phe Ser Ile Asn ***
                515

(2) INFORMATION FOR SEQ ID NO: 2:

(i) SEQUENCE CHARACTERISTICS:
        (A) LENGTH: 1473
        (B) TYPE: nucleic acid
        (C) STRANDEDNESS: double
        (D) TOPOLOGY: linear (ii) SEQUENCE DESCRIPTION: SEQ ID NO: 2:

ATG GAT TCT ATT GTG TCC CTT GTG CTC TGT CTC TCA TGT TTG CTT          45
Met Asp Ser Ile Val Ser Leu Val Leu Cys Leu Ser Cys Leu Leu
 1               5                  10                  15

CTC CTT TCA CTC TGG AGA CAG AGC TCT GGG AGA GGA AAA CTC CCT          90
Leu Leu Ser Leu Trp Arg Gln Ser Ser Gly Arg Gly Lys Leu Pro
                20                  25                  30

CCT GGC CCC ACT CCT CTC CCA GTG ATT GGA AAT ATC CTA CAG ATA          135
Pro Gly Pro Thr Pro Leu Pro Val Ile Gly Asn Ile Leu Gln Ile
                35                  40                  45

GGT ATT AAG GAC ATC AGC AAA TCC TTA ACC AAT CTC TCA AAG GTC          180
Gly Ile Lys Asp Ile Ser Lys Ser Leu Thr Asn Leu Ser Lys Val
                50                  55                  60

TAT GGC CCT GTG TTC ACT CTG TAT TTT GGC CTG AAA CCC ATA GTG          225
Tyr Gly Pro Val Phe Thr Leu Tyr Phe Gly Leu Lys Pro Ile Val
                65                  70                  75

GTG CTG CAT GGA TAT GAA GCA GTG AAG GAA GCC CTG ATT GAT CTT          270
Val Leu His Gly Tyr Glu Ala Val Lys Glu Ala Leu Ile Asp Leu
                80                  85                  90

GGA GAG GAG TTT TCT GGA AGA GGC ATT TTC CCA CTG GCT GAA AGA          315
Gly Glu Glu Phe Ser Gly Arg Gly Ile Phe Pro Leu Ala Glu Arg
                95                  100                 105

GCT AAC AGA GGA TTT GGA ATT GTT TTC AGC AAT GGA AAG AAA TGG          360
Ala Asn Arg Gly Phe Gly Ile Val Phe Ser Asn Gly Lys Lys Trp
                110                 115                 120

AAG GAG ATC CGG CGT TTC TCC CTC ATG ACG CTG CGG AAT TTT GGG          405
```

```
Lys Glu Ile Arg Arg Phe Ser Leu Met Thr Leu Arg Asn Phe Gly
             125                 130                 135

ATG GGG AAG AGG AGC ATT GAG GAC CGT GTT CAA GAG GAA GCC CGC              450
Met Gly Lys Arg Ser Ile Glu Asp Arg Val Gln Glu Glu Ala Arg
             140                 145                 150

TGC CTT GTG GAG GAG TTG AGA AAA ACC AAG GCC TCA CCC TGT GAT              495
Cys Leu Val Glu Glu Leu Arg Lys Thr Lys Ala Ser Pro Cys Asp
             155                 160                 165

CCC ACT TTC ATC CTG GGC TGT GCT CCC TGC AAT GTG ATC TGC TCC              540
Pro Thr Phe Ile Leu Gly Cys Ala Pro Cys Asn Val Ile Cys Ser
             170                 175                 180

ATT ATT TTC CAT AAA CGT TTT GAT TAT AAA GAT CAG CAA TTT CTT              585
Ile Ile Phe His Lys Arg Phe Asp Tyr Lys Asp Gln Gln Phe Leu
             185                 190                 195

AAC TTA ATG GAA AAG TTG AAT GAA AAC ATC AAG ATT TTG AGC AGC              630
Asn Leu Met Glu Lys Leu Asn Glu Asn Ile Lys Ile Leu Ser Ser
             200                 205                 210

CCC TGG ATC CAG ATC TGC AAT AAT TTT TCT CCT ATC ATT GAT TAC              675
Pro Trp Ile Gln Ile Cys Asn Asn Phe Ser Pro Ile Ile Asp Tyr
             215                 220                 225

TTC CCG GGA ACT CAC AAC AAA TTA CTT AAA AAC GTT GCT TTT ATG              720
Phe Pro Gly Thr His Asn Lys Leu Leu Lys Asn Val Ala Phe Met
             230                 235                 240

AAA AGT TAT ATT TTG GAA AAA GTA AAA GAA CAC CAA GAA TCA ATG              765
Lys Ser Tyr Ile Leu Glu Lys Val Lys Glu His Gln Glu Ser Met
             245                 250                 255

GAC ATG AAC AAC CCT CAG GAC TTT ATT GAT TGC TTC CTG ATG AAA              810
Asp Met Asn Asn Pro Gln Asp Phe Ile Asp Cys Phe Leu Met Lys
             260                 265                 270

ATG GAG AAG GAA AAG CAC AAC CAA CCA TCT GAA TTT ACT ATT GAA              855
Met Glu Lys Glu Lys His Asn Gln Pro Ser Glu Phe Thr Ile Glu
             275                 280                 285

AGC TTG GAA AAC ACT GCA GTT GAC TTG TTT GGA GCT GGG ACA GAG              900
Ser Leu Glu Asn Thr Ala Val Asp Leu Phe Gly Ala Gly Thr Glu
             290                 295                 300

ACG ACA AGC ACA ACC CTG AGA TAT GCT CTC CTT CTC CTG CTG AAG              945
Thr Thr Ser Thr Thr Leu Arg Tyr Ala Leu Leu Leu Leu Leu Lys
             305                 310                 315

CAC CCA GAG GTC ACA GCT AAA GTC CAG GAA GAG ATT GAA CGT GTG              990
His Pro Glu Val Thr Ala Lys Val Gln Glu Glu Ile Glu Arg Val
             320                 325                 330

ATT GGC AGA AAC CGG AGC CCC TGC ATG CAA GAC AGG AGC CAC ATG             1035
Ile Gly Arg Asn Arg Ser Pro Cys Met Gln Asp Arg Ser His Met
             335                 340                 345

CCC TAC ACA GAT GCT GTG GTG CAC GAG GTC CAG AGA TAC ATT GAC             1080
Pro Tyr Thr Asp Ala Val Val His Glu Val Gln Arg Tyr Ile Asp
             350                 355                 360

CTT CTC CCC ACC AGC CTG CCC CAT GCA GTG ACC TGT GAC ATT AAA             1125
Leu Leu Pro Thr Ser Leu Pro His Ala Val Thr Cys Asp Ile Lys
             365                 370                 375

TTC AGA AAC TAT CTC ATT CCC AAG GGC ACA ACC ATA TTA ATT TCC             1170
Phe Arg Asn Tyr Leu Ile Pro Lys Gly Thr Thr Ile Leu Ile Ser
             380                 385                 390

CTG ACT TCT GTG CTA CAT GAC AAC AAA GAA TTT CCC AAC CCA GAG             1215
Leu Thr Ser Val Leu His Asp Asn Lys Glu Phe Pro Asn Pro Glu
             395                 400                 405

ATG TTT GAC CCT CAT CAC TTT CTG GAT GAA GGT GGC AAT TTT AAG             1260
Met Phe Asp Pro His His Phe Leu Asp Glu Gly Gly Asn Phe Lys
             410                 415                 420
```

```
AAA AGT AAA TAC TTC ATG CCT TTC TCA GCA GGA AAA CGG ATT TGT      1305
Lys Ser Lys Tyr Phe Met Pro Phe Ser Ala Gly Lys Arg Ile Cys
            425                 430                 435

GTG GGA GAA GCC CTG GCC GGC ATG GAG CTG TTT TTA TTC CTG ACC      1350
Val Gly Glu Ala Leu Ala Gly Met Glu Leu Phe Leu Phe Leu Thr
            440                 445                 450

TCC ATT TTA CAG AAC TTT AAC CTG AAA TCT CTG GTT GAC CCA AAG      1395
Ser Ile Leu Gln Asn Phe Asn Leu Lys Ser Leu Val Asp Pro Lys
            455                 460                 465

AAC CTT GAC ACC ACT CCA GTT GTC AAT GGA TTT GCC TCT GTG CCG      1440
Asn Leu Asp Thr Thr Pro Val Val Asn Gly Phe Ala Ser Val Pro
            470                 475                 480

CCC TTC TAC CAG CTG TGC TTC ATT CCT GTC TGA                      1473
Pro Phe Tyr Gln Leu Cys Phe Ile Pro Val ***
            485                 490

(2) INFORMATION FOR SEQ ID NO: 3:

(i) SEQUENCE CHARACTERISTICS:
        (A) LENGTH:  1482
        (B) TYPE:  nucleic acid
        (C) STRANDEDNESS:  double
        (D) TOPOLOGY:  linear (ii) SEQUENCE DESCRIPTION: SEQ ID NO:  3:

ATG TCT GCC CTC GGA GTC ACC GTG GCC CTG CTG GTG TGG GCG GCC      45
Met Ser Ala Leu Gly Val Thr Val Ala Leu Leu Val Trp Ala Ala
  1               5                  10                  15

TTC CTC CTG CTG GTG TCC ATG TGG AGG CAG GTG CAC AGC AGC TGG      90
Phe Leu Leu Leu Val Ser Met Trp Arg Gln Val His Ser Ser Trp
             20                  25                  30

AAT CTG CCC CCA GGC CCT TTC CCG CTT CCC ATC ATC GGG AAC CTC      135
Asn Leu Pro Pro Gly Pro Phe Pro Leu Pro Ile Ile Gly Asn Leu
             35                  40                  45

TTC CAG TTG GAA TTG AAG AAT ATT CCC AAG TCC TTC ACC CGG TTG      180
Phe Gln Leu Glu Leu Lys Asn Ile Pro Lys Ser Phe Thr Arg Leu
             50                  55                  60

GCC CAG CGC TTC GGG CCG GTG TTC ACG CTG TAC GTG GGC TCG CAG      225
Ala Gln Arg Phe Gly Pro Val Phe Thr Leu Tyr Val Gly Ser Gln
             65                  70                  75

CGC ATG GTG GTG ATG CAC GGC TAC AAG GCG GTG AAG GAA GCG CTG      270
Arg Met Val Val Met His Gly Tyr Lys Ala Val Lys Glu Ala Leu
             80                  85                  90

CTG GAC TAC AAG GAC GAG TTC TCG GGC AGA GGC GAC CTC CCC GCG      315
Leu Asp Tyr Lys Asp Glu Phe Ser Gly Arg Gly Asp Leu Pro Ala
             95                 100                 105

TTC CAT GCG CAC AGG GAC AGG GGA ATC ATT TTT AAT AAT GGA CCT      360
Phe His Ala His Arg Asp Arg Gly Ile Ile Phe Asn Asn Gly Pro
            110                 115                 120

ACC TGG AAG GAC ATC CGG CGG TTT TCC CTG ACC ACC CTC CGG AAC      405
Thr Trp Lys Asp Ile Arg Arg Phe Ser Leu Thr Thr Leu Arg Asn
            125                 130                 135

TAT GGG ATG GGG AAA CAG GGC AAT GAG AGC CGG ATC CAG AGG GAG      450
Tyr Gly Met Gly Lys Gln Gly Asn Glu Ser Arg Ile Gln Arg Glu
            140                 145                 150

GCC CAC TTC CTG CTG GAA GCA CTC AGG AAG ACC CAA GGC CAG CCT      495
Ala His Phe Leu Leu Glu Ala Leu Arg Lys Thr Gln Gly Gln Pro
            155                 160                 165

TTC GAC CCC ACC TTC CTC ATC GGG TGC GCG CCC TGC AAC GTC ATA      540
Phe Asp Pro Thr Phe Leu Ile Gly Cys Ala Pro Cys Asn Val Ile
            170                 175                 180
```

```
GCC GAC ATC CTC TTC CGC AAG CAT TTT GAC TAC AAT GAT GAG AAG        585
Ala Asp Ile Leu Phe Arg Lys His Phe Asp Tyr Asn Asp Glu Lys
                185                 190                 195

TTT CTA AGG CTG ATG TAT TTG TTT AAT GAG AAC TTC CAC CTA CTC        630
Phe Leu Arg Leu Met Tyr Leu Phe Asn Glu Asn Phe His Leu Leu
                200                 205                 210

AGC ACT CCC TGG CTC CAG CTT TAC AAT AAT TTT CCC AGC TTT CTA        675
Ser Thr Pro Trp Leu Gln Leu Tyr Asn Asn Phe Pro Ser Phe Leu
                215                 220                 225

CAC TAC TTG CCT GGA AGC CAC AGA AAA GTC ATA AAA AAT GTG GCT        720
His Tyr Leu Pro Gly Ser His Arg Lys Val Ile Lys Asn Val Ala
                230                 235                 240

GAA GTA AAA GAG TAT GTG TCT GAA AGG GTG AAG GAG CAC CAT CAA        765
Glu Val Lys Glu Tyr Val Ser Glu Arg Val Lys Glu His His Gln
                245                 250                 255

TCT CTG GAC CCC AAC TGT CCC CGG GAC CTC ACC GAC TGC CTG CTC        810
Ser Leu Asp Pro Asn Cys Pro Arg Asp Leu Thr Asp Cys Leu Leu
                260                 265                 270

GTG GAA ATG GAG AAG GAA AAG CAC AGT GCA GAG CGC TTG TAC ACA        855
Val Glu Met Glu Lys Glu Lys His Ser Ala Glu Arg Leu Tyr Thr
                275                 280                 285

ATG GAC GGT ATC ACC GTG ACT GTG GCC GAC CTG TTC TTT GCG GGG        900
Met Asp Gly Ile Thr Val Thr Val Ala Asp Leu Phe Phe Ala Gly
                290                 295                 300

ACA GAG ACC ACC AGC ACA ACT CTG AGA TAT GGG CTC CTG ATT CTC        945
Thr Glu Thr Thr Ser Thr Thr Leu Arg Tyr Gly Leu Leu Ile Leu
                305                 310                 315

ATG AAA TAC CCT GAG ATC GAA GAG AAG CTC CAT GAA GAA ATT GAC        990
Met Lys Tyr Pro Glu Ile Glu Glu Lys Leu His Glu Glu Ile Asp
                320                 325                 330

AGG GTG ATT GGG CCA AGC CGA ATC CCT GCC ATC AAG GAT AGG CAA       1035
Arg Val Ile Gly Pro Ser Arg Ile Pro Ala Ile Lys Asp Arg Gln
                335                 340                 345

GAG ATG CCC TAC ATG GAT GCT GTG GTG CAT GAG ATT CAG CGG TTC       1080
Glu Met Pro Tyr Met Asp Ala Val Val His Glu Ile Gln Arg Phe
                350                 355                 360

ATC ACC CTC GTG CCC TCC AAC CTG CCC CAT GAA GCA ACC CGA GAC       1125
Ile Thr Leu Val Pro Ser Asn Leu Pro His Glu Ala Thr Arg Asp
                365                 370                 375

ACC ATT TTC AGA GGA TAC CTC ATC CCC AAG GGC ACA GTC GTA GTG       1170
Thr Ile Phe Arg Gly Tyr Leu Ile Pro Lys Gly Thr Val Val Val
                380                 385                 390

CCA ACT CTG GAC TCT GTT TTG TAT GAC AAC CAA GAA TTT CCT GAT       1215
Pro Thr Leu Asp Ser Val Leu Tyr Asp Asn Gln Glu Phe Pro Asp
                395                 400                 405

CCA GAA AAG TTT AAG CCA GAA CAC TTC CTG AAT GAA AAT GGA AAG       1260
Pro Glu Lys Phe Lys Pro Glu His Phe Leu Asn Glu Asn Gly Lys
                410                 415                 420

TTC AAG TAC AGT GAC TAT TTC AAG CCA TTT TCC ACA GGA AAA CGA       1305
Phe Lys Tyr Ser Asp Tyr Phe Lys Pro Phe Ser Thr Gly Lys Arg
                425                 430                 435

GTG TGT GCT GGA GAA GGC CTG GCT CGC ATG GAG TTG TTT CTT TTG       1350
Val Cys Ala Gly Glu Gly Leu Ala Arg Met Glu Leu Phe Leu Leu
                440                 445                 450

TTG TGT GCC ATT TTG CAG CAT TTT AAT TTG AAG CCT CTC GTT GAC       1395
Leu Cys Ala Ile Leu Gln His Phe Asn Leu Lys Pro Leu Val Asp
                455                 460                 465

CCA AAG GAT ATC GAC CTC AGC CCT ATA CAT ATT GGG TTT GGC TGT       1440
Pro Lys Asp Ile Asp Leu Ser Pro Ile His Ile Gly Phe Gly Cys
                470                 475                 480
```

```
ATC CCA CCA CGT TAC AAA CTC TGT GTC ATT CCC CGC TCA TGA               1482
Ile Pro Pro Arg Tyr Lys Leu Cys Val Ile Pro Arg Ser ***
            485                 490

(2) INFORMATION FOR SEQ ID NO: 4:

(i) SEQUENCE CHARACTERISTICS:
        (A) LENGTH: 1512
        (B) TYPE: nucleic acid
        (C) STRANDEDNESS: double
        (D) TOPOLOGY: linear (ii) SEQUENCE DESCRIPTION: SEQ ID NO: 4:

ATG GCT CTC ATC CCA GAC TTG GCC ATG GAA ACC TGG CTT CTC CTG            45
Met Ala Leu Ile Pro Asp Leu Ala Met Glu Thr Trp Leu Leu Leu
 1               5                  10                  15

GCT GTC AGC CTG GTG CTC CTC TAT CTA TAT GGA ACC CAT TCA CAT            90
Ala Val Ser Leu Val Leu Leu Tyr Leu Tyr Gly Thr His Ser His
                20                  25                  30

GGA CTT TTT AAG AAG CTT GGA ATT CCA GGG CCC ACA CCT CTG CCT           135
Gly Leu Phe Lys Lys Leu Gly Ile Pro Gly Pro Thr Pro Leu Pro
            35                  40                      45

TTT TTG GGA AAT ATT TTG TCC TAC CAT AAG GGC TTT TGT ATG TTT           180
Phe Leu Gly Asn Ile Leu Ser Tyr His Lys Gly Phe Cys Met Phe
                50                  55                  60

GAC ATG GAA TGT CAT AAA AAG TAT GGA AAA GTG TGG GGC TTT TAT           225
Asp Met Glu Cys His Lys Lys Tyr Gly Lys Val Trp Gly Phe Tyr
                65                  70                  75

GAT GGT CAA CAG CCT GTG CTG GCT ATC ACA GAT CCT GAC ATG ATC           270
Asp Gly Gln Gln Pro Val Leu Ala Ile Thr Asp Pro Asp Met Ile
                80                  85                  90

AAA ACA GTG CTA GTG AAA GAA TGT TAT TCT GTC TTC ACA AAC CGG           315
Lys Thr Val Leu Val Lys Glu Cys Tyr Ser Val Phe Thr Asn Arg
                95                 100                 105

AGG CCT TTT GGT CCA GTG GGA TTT ATG AAA AGT GCC ATC TCT ATA           360
Arg Pro Phe Gly Pro Val Gly Phe Met Lys Ser Ala Ile Ser Ile
               110                 115                 120

GCT GAG GAT GAA GAA TGG AAG AGA TTA CGA TCA TTG CTG TCT CCA           405
Ala Glu Asp Glu Glu Trp Lys Arg Leu Arg Ser Leu Leu Ser Pro
               125                 130                 135

ACC TTC ACC AGT GGA AAA CTC AAG GAG ATG GTC CCT ATC ATT GCC           450
Thr Phe Thr Ser Gly Lys Leu Lys Glu Met Val Pro Ile Ile Ala
               140                 145                 150

CAG TAT GGA GAT GTG TTG GTG AGA AAT CTG AGG CGG GAA GCA GAG           495
Gln Tyr Gly Asp Val Leu Val Arg Asn Leu Arg Arg Glu Ala Glu
               155                 160                 165

ACA GGC AAG CCT GTC ACC TTG AAA GAC GTC TTT GGG GCC TAC AGC           540
Thr Gly Lys Pro Val Thr Leu Lys Asp Val Phe Gly Ala Tyr Ser
               170                 175                 180

ATG GAT GTG ATC ACT AGC ACA TCA TTT GGA GTG AAC ATC GAC TCT           585
Met Asp Val Ile Thr Ser Thr Ser Phe Gly Val Asn Ile Asp Ser
               185                 190                 195

CTC AAC AAT CCA CAA GAC CCC TTT GTG GAA AAC ACC AAG AAG CTT           630
Leu Asn Asn Pro Gln Asp Pro Phe Val Glu Asn Thr Lys Lys Leu
               200                 205                 210

TTA AGA TTT GAT TTT TTG GAT CCA TTC TTT CTC TCA ATA ACA GTC           675
Leu Arg Phe Asp Phe Leu Asp Pro Phe Phe Leu Ser Ile Thr Val
               215                 220                 225

TTT CCA TTC CTC ATC CCA ATT CTT GAA GTA TTA AAT ATC TGT GTG           720
Phe Pro Phe Leu Ile Pro Ile Leu Glu Val Leu Asn Ile Cys Val
               230                 235                 240
```

```
TTT CCA AGA GAA GTT ACA AAT TTT TTA AGA AAA TCT GTA AAA AGG          765
Phe Pro Arg Glu Val Thr Asn Phe Leu Arg Lys Ser Val Lys Arg
                245                 250                 255

ATG AAA GAA AGT CGC CTC GAA GAT ACA CAA AAG CAC CGA GTG GAT          810
Met Lys Glu Ser Arg Leu Glu Asp Thr Gln Lys His Arg Val Asp
                260                 265                 270

TTC CTT CAG CTG ATG ATT GAC TCT CAG AAT TCA AAA GAA ACT GAG          855
Phe Leu Gln Leu Met Ile Asp Ser Gln Asn Ser Lys Glu Thr Glu
                275                 280                 285

TCC CAC AAA GCT CTG TCC GAT CTG GAG CTC GTG GCC CAA TCA ATT          900
Ser His Lys Ala Leu Ser Asp Leu Glu Leu Val Ala Gln Ser Ile
                290                 295                 300

ATC TTT ATT TTT GCT GGC TAT GAA ACC ACG AGC AGT GTT CTC TCC          945
Ile Phe Ile Phe Ala Gly Tyr Glu Thr Thr Ser Ser Val Leu Ser
                305                 310                 315

TTC ATT ATG TAT GAA CTG GCC ACT CAC CCT GAT GTC CAG CAG AAA          990
Phe Ile Met Tyr Glu Leu Ala Thr His Pro Asp Val Gln Gln Lys
                320                 325                 330

CTG CAG GAG GAA ATT GAT GCA GTT TTA CCC AAT AAG GCA CCA CCC         1035
Leu Gln Glu Glu Ile Asp Ala Val Leu Pro Asn Lys Ala Pro Pro
                335                 340                 345

ACC TAT GAT ACT GTG CTA CAG ATG GAG TAT CTT GAC ATG GTG GTG         1080
Thr Tyr Asp Thr Val Leu Gln Met Glu Tyr Leu Asp Met Val Val
                350                 355                 360

AAT GAA ACG CTC AGA TTA TTC CCA ATT GCT ATG AGA CTT GAG AGG         1125
Asn Glu Thr Leu Arg Leu Phe Pro Ile Ala Met Arg Leu Glu Arg
                365                 370                 375

GTC TGC AAA AAA GAT GTT GAG ATC AAT GGG ATG TTC ATT CCC AAA         1170
Val Cys Lys Lys Asp Val Glu Ile Asn Gly Met Phe Ile Pro Lys
                380                 385                 390

GGG TGG GTG GTG ATG ATT CCA AGC TAT GCT CTT CAC CGT GAC CCA         1215
Gly Trp Val Val Met Ile Pro Ser Tyr Ala Leu His Arg Asp Pro
                395                 400                 405

AAG TAC TGG ACA GAG CCT GAG AAG TTC CTC CCT GAA AGA TTC AGC         1260
Lys Tyr Trp Thr Glu Pro Glu Lys Phe Leu Pro Glu Arg Phe Ser
                410                 415                 420

AAG AAG AAC AAG GAC AAC ATA GAT CCT TAC ATA TAC ACA CCC TTT         1305
Lys Lys Asn Lys Asp Asn Ile Asp Pro Tyr Ile Tyr Thr Pro Phe
                425                 430                 435

GGA AGT GGA CCC AGA AAC TGC ATT GGC ATG AGG TTT GCT CTC ATG         1350
Gly Ser Gly Pro Arg Asn Cys Ile Gly Met Arg Phe Ala Leu Met
                440                 445                 450

AAC ATG AAA CTT GCT CTA ATC AGA GTC CTT CAG AAC TTC TCC TTC         1395
Asn Met Lys Leu Ala Leu Ile Arg Val Leu Gln Asn Phe Ser Phe
                455                 460                 465

AAA CCT TGT AAA GAA ACA CAG ATC CCC CTG AAA TTA AGC TTA GGA         1440
Lys Pro Cys Lys Glu Thr Gln Ile Pro Leu Lys Leu Ser Leu Gly
                470                 475                 480

GGA CTT CTT CAA CCA GAA AAA CCC GTT GTT CTA AAG GTT GAG TCA         1485
Gly Leu Leu Gln Pro Glu Lys Pro Val Val Leu Lys Val Glu Ser
                485                 490                 495

AGG GAT GGC ACC GTA AGT GGA GCC TGA                                 1512
Arg Asp Gly Thr Val Ser Gly Ala ***
                500

(2) INFORMATION FOR SEQ ID NO: 5:

(i) SEQUENCE CHARACTERISTICS:
        (A) LENGTH: 1539
        (B) TYPE: nucleic acid
```

```
        (C) STRANDEDNESS:  double
        (D) TOPOLOGY:      linear (ii) SEQUENCE DESCRIPTION: SEQ ID NO: 5:

ATG CTT TTC CCA ATC TCC ATG TCG GCC ACG GAG TTT CTT CTG GCC        45
Met Leu Phe Pro Ile Ser Met Ser Ala Thr Glu Phe Leu Leu Ala
 1               5                  10                  15

TCT GTC ATC TTC TGT CTG GTA TTC TGG GTA ATC AGG GCC TCA AGA        90
Ser Val Ile Phe Cys Leu Val Phe Trp Val Ile Arg Ala Ser Arg
                20                  25                  30

CCT CAG GTC CCC AAA GGC CTG AAG AAT CCA CCA GGG CCA TGG GGC       135
Pro Gln Val Pro Lys Gly Leu Lys Asn Pro Pro Gly Pro Trp Gly
             35                  40                  45

TGG CCT CTG ATT GGG CAC ATG CTG ACC CTG GGA AAG AAC CCG CAC       180
Trp Pro Leu Ile Gly His Met Leu Thr Leu Gly Lys Asn Pro His
         50                  55                  60

CTG GCA CTG TCA AGG ATG AGC CAG CAG TAT GGG GAC GTG CTG CAG       225
Leu Ala Leu Ser Arg Met Ser Gln Gln Tyr Gly Asp Val Leu Gln
     65                  70                  75

ATC CGA ATT GGC TCC ACA CCC GTG GTG GTG CTG AGC GGC CTG GAC       270
Ile Arg Ile Gly Ser Thr Pro Val Val Val Leu Ser Gly Leu Asp
 80                  85                  90

ACC ATC CGG CAG GCC CTG GTG CGG CAG GGC GAT GAT TTC AAG GGC       315
Thr Ile Arg Gln Ala Leu Val Arg Gln Gly Asp Asp Phe Lys Gly
                 95                 100                 105

CGG CCC GAC CTC TAC ACC TTC ACC CTC ATC AGT AAT GGT CAG AGC       360
Arg Pro Asp Leu Tyr Thr Phe Thr Leu Ile Ser Asn Gly Gln Ser
            110                 115                 120

ATG TCC TTC AGC CCA GAC TCT GGA CCA GTG TGG GCT GCC CGC CGG       405
Met Ser Phe Ser Pro Asp Ser Gly Pro Val Trp Ala Ala Arg Arg
        125                 130                 135

CGC CTG GCC CAG AAT GGC CTG AAA AGT TTC TCC ATT GCC TCT GAC       450
Arg Leu Ala Gln Asn Gly Leu Lys Ser Phe Ser Ile Ala Ser Asp
    140                 145                 150

CCA GCC TCC TCA ACC TCC TGC TAC CTG GAA GAG CAT GTG AGC AAG       495
Pro Ala Ser Ser Thr Ser Cys Tyr Leu Glu Glu His Val Ser Lys
155                 160                 165

GAG GCT GAG GTC CTG ATA AGC ACG TTG CAG GAG CTG ATG GCA GGG       540
Glu Ala Glu Val Leu Ile Ser Thr Leu Gln Glu Leu Met Ala Gly
                170                 175                 180

CCT GGG CAC TTT AAC CCC TAC AGG TAT GTG GTG GTA TCA GTG ACC       585
Pro Gly His Phe Asn Pro Tyr Arg Tyr Val Val Val Ser Val Thr
            185                 190                 195

AAT GTC ATC TGT GCC ATT TGC TTT GGC CGG CGC TAT GAC CAC AAC       630
Asn Val Ile Cys Ala Ile Cys Phe Gly Arg Arg Tyr Asp His Asn
        200                 205                 210

CAC CAA GAA CTG CTT AGC CTA GTC AAC CTG AAT AAT AAT TTC GGG       675
His Gln Glu Leu Leu Ser Leu Val Asn Leu Asn Asn Asn Phe Gly
    215                 220                 225

GAG GTG GTT GGC TCT GGA AAC CCA GCT GAC TTC ATC CCT ATT CTT       720
Glu Val Val Gly Ser Gly Asn Pro Ala Asp Phe Ile Pro Ile Leu
230                 235                 240

CGC TAC CTA CCC AAC CCT TCC CTG AAT GCC TTC AAG GAC CTG AAT       765
Arg Tyr Leu Pro Asn Pro Ser Leu Asn Ala Phe Lys Asp Leu Asn
                245                 250                 255

GAG AAG TTC TAC AGC TTC ATG CAG AAG ATG GTC AAG GAG CAC TAC       810
Glu Lys Phe Tyr Ser Phe Met Gln Lys Met Val Lys Glu His Tyr
            260                 265                 270

AAA ACC TTT GAG AAG GGC CAC ATC CGG GAC ATC ACA GAC AGC CTG       855
Lys Thr Phe Glu Lys Gly His Ile Arg Asp Ile Thr Asp Ser Leu
```

```
                   275                  280                  285
ATT GAG CAC TGT CAG GAG AAG CAG CTG GAT GAG AAC GCC AAT GTC         900
Ile Glu His Cys Gln Glu Lys Gln Leu Asp Glu Asn Ala Asn Val
              290                  295                  300

CAG CTG TCA GAT GAG AAG ATC ATT AAC ATC GTC TTG GAC CTC TTT         945
Gln Leu Ser Asp Glu Lys Ile Ile Asn Ile Val Leu Asp Leu Phe
              305                  310                  315

GGA GCT GGG TTT GAC ACA GTC ACA ACT GCT ATC TCC TGG AGC CTC         990
Gly Ala Gly Phe Asp Thr Val Thr Thr Ala Ile Ser Trp Ser Leu
              320                  325                  330

ATG TAT TTG GTG ATG AAC CCC AGG GTA CAG AGA AAG ATC CAA GAG        1035
Met Tyr Leu Val Met Asn Pro Arg Val Gln Arg Lys Ile Gln Glu
              335                  340                  345

GAG CTC GAC ACA GTG ATT GGC AGG TCA CGG CGG CCC CGG CTC TCT        1080
Glu Leu Asp Thr Val Ile Gly Arg Ser Arg Arg Pro Arg Leu Ser
              350                  355                  360

GAC AGA TCC CAT CTG CCC TAT ATG GAG GCC TTC ATC CTG GAG ACC        1125
Asp Arg Ser His Leu Pro Tyr Met Glu Ala Phe Ile Leu Glu Thr
              365                  370                  375

TTC CGA CAC TCT TCC TTC GTC CCC TTC ACC ATC CCC CAC AGC ACA        1170
Phe Arg His Ser Ser Phe Val Pro Phe Thr Ile Pro His Ser Thr
              380                  385                  390

ACA AGA GAC ACA AGT TTG AAA GGC TTT TAC ATC CCC AAG GGG CGT        1215
Thr Arg Asp Thr Ser Leu Lys Gly Phe Tyr Ile Pro Lys Gly Arg
              395                  400                  405

TGT GTC TTT GTA AAC CAG TGG CAG ATC AAC CAT GAC CAG AAG CTA        1260
Cys Val Phe Val Asn Gln Trp Gln Ile Asn His Asp Gln Lys Leu
              410                  415                  420

TGG GTC AAC CCA TCT GAG TTC CTA CCT GAA CGG TTT CTC ACC CCT        1305
Trp Val Asn Pro Ser Glu Phe Leu Pro Glu Arg Phe Leu Thr Pro
              425                  430                  435

GAT GGT GCT ATC GAC AAG GTG TTA AGT GAG AAG GTG ATT ATC TTT        1350
Asp Gly Ala Ile Asp Lys Val Leu Ser Glu Lys Val Ile Ile Phe
              440                  445                  450

GGC ATG GGC AAG CGG AAG TGT ATC GGT GAG ACC ATT GCC AGC TGG        1395
Gly Met Gly Lys Arg Lys Cys Ile Gly Glu Thr Ile Ala Ser Trp
              455                  460                  465

GAG GTC TTT CTC TTC CTG GCT ATC CTG CTG CAA CGG GTG GAA TTC        1440
Glu Val Phe Leu Phe Leu Ala Ile Leu Leu Gln Arg Val Glu Phe
              470                  475                  480

AGC GTG CCA CTG GGC GTG AAG GTG GAC ATG ACC CCC ATC TAT GGG        1485
Ser Val Pro Leu Gly Val Lys Val Asp Met Thr Pro Ile Tyr Gly
              485                  490                  495

CTA ACC ATG AAG CAT GCC TGC TGT GAG CAC TTC CAA ATG CAG CTG        1530
Leu Thr Met Lys His Ala Cys Cys Glu His Phe Gln Met Gln Leu
              500                  505                  510

CGC TCT TAG                                                        1539
Arg Ser ***

(2) INFORMATION FOR SEQ ID NO: 6:

(i) SEQUENCE CHARACTERISTICS:
        (A) LENGTH: 1539
        (B) TYPE: nucleic acid
        (C) STRANDEDNESS: double
        (D) TOPOLOGY: linear (ii) SEQUENCE DESCRIPTION: SEQ ID NO: 6:

ATG CTT TTC CCA ATC TCC ATG TCG GCC ACG GAG TTT CTT CTG GCC          45
Met Leu Phe Pro Ile Ser Met Ser Ala Thr Glu Phe Leu Leu Ala
  1                5                 10                 15
```

```
TCT GTC ATC TTC TGT CTG GTA TTC TGG GTA ATC AGG GCC TCA AGA        90
Ser Val Ile Phe Cys Leu Val Phe Trp Val Ile Arg Ala Ser Arg
             20                  25                  30

CCT CAG GTC CCC AAA GGC CTG AAG AAT CCA CCA GGG CCA TGG GGC       135
Pro Gln Val Pro Lys Gly Leu Lys Asn Pro Pro Gly Pro Trp Gly
             35                  40                  45

TGG CCT CTG ATT GGG CAC ATG CTG ACC CTG GGA AAG AAC CCG CAC       180
Trp Pro Leu Ile Gly His Met Leu Thr Leu Gly Lys Asn Pro His
             50                  55                  60

CTG GCA CTG TCA AGG ATG AGC CAG CAG TAT GGG GAC GTG CTG CAG       225
Leu Ala Leu Ser Arg Met Ser Gln Gln Tyr Gly Asp Val Leu Gln
             65                  70                  75

ATC CGA ATT GGC TCC ACA CCC GTG GTG GTG CTG AGC GGC CTG GAC       270
Ile Arg Ile Gly Ser Thr Pro Val Val Val Leu Ser Gly Leu Asp
             80                  85                  90

ACC ATC CGG CAG GCC CTG GTG CGG CAG GGC GAT GAT TTC AAG GGC       315
Thr Ile Arg Gln Ala Leu Val Arg Gln Gly Asp Asp Phe Lys Gly
             95                 100                 105

CGG CCC GAC CTC TAC ACC TTC ACC CTC ATC AGT AAT GGT CAG AGC       360
Arg Pro Asp Leu Tyr Thr Phe Thr Leu Ile Ser Asn Gly Gln Ser
            110                 115                 120

ATG TCC TTC AGC CCA GAC TCT GGA CCA GTG TGG GCT GCC CGC CGG       405
Met Ser Phe Ser Pro Asp Ser Gly Pro Val Trp Ala Ala Arg Arg
            125                 130                 135

CGC CTG GCC CAG AAT GGC CTG AAA AGT TTC TCC ATT GCC TCT GAC       450
Arg Leu Ala Gln Asn Gly Leu Lys Ser Phe Ser Ile Ala Ser Asp
            140                 145                 150

CCA GCC TCC TCA ACC TCC TGC TAC CTG GAA GAG CAT GTG AGC AAG       495
Pro Ala Ser Ser Thr Ser Cys Tyr Leu Glu Glu His Val Ser Lys
            155                 160                 165

GAG GCT GAG GTC CTG ATA AGC ACG TTG CAG GAG CTG ATG GCA GGG       540
Glu Ala Glu Val Leu Ile Ser Thr Leu Gln Glu Leu Met Ala Gly
            170                 175                 180

CCT GGG CAC TTT AAC CCC TAC AGG TAT GTG GTG GTA TCA GTG ACC       585
Pro Gly His Phe Asn Pro Tyr Arg Tyr Val Val Val Ser Val Thr
            185                 190                 195

AAT GTC ATC TGT GCC ATT TGC TTT GGC CGG CGC TAT GAC CAC AAC       630
Asn Val Ile Cys Ala Ile Cys Phe Gly Arg Arg Tyr Asp His Asn
            200                 205                 210

CAC CAA GAA CTG CTT AGC CTA GTC AAC CTG AAT AAT AAT TTC GGG       675
His Gln Glu Leu Leu Ser Leu Val Asn Leu Asn Asn Asn Phe Gly
            215                 220                 225

GAG GTG GTT GGC TCT GGA AAC CCA GCT GAC TTC ATC CCT ATT CTT       720
Glu Val Val Gly Ser Gly Asn Pro Ala Asp Phe Ile Pro Ile Leu
            230                 235                 240

CGC TAC CTA CCC AAC CCT TCC CTG AAT GCC TTC AAG GAC CTG AAT       765
Arg Tyr Leu Pro Asn Pro Ser Leu Asn Ala Phe Lys Asp Leu Asn
            245                 250                 255

GAG AAG TTC TAC AGC TTC ATG CAG AAG ATG GTC AAG GAG CAC TAC       810
Glu Lys Phe Tyr Ser Phe Met Gln Lys Met Val Lys Glu His Tyr
            260                 265                 270

AAA ACC TTT GAG AAG GGC CAC ATC CGG GAC ATC ACA GAC AGC CTG       855
Lys Thr Phe Glu Lys Gly His Ile Arg Asp Ile Thr Asp Ser Leu
            275                 280                 285

ATT GAG CAC TGT CAG GAG AAG CAG CTG GAT GAG AAC GCC AAT GTC       900
Ile Glu His Cys Gln Glu Lys Gln Leu Asp Glu Asn Ala Asn Val
            290                 295                 300

CAG CTG TCA GAT GAG AAG ATC ATT AAC ATC GTC TTG GAC CTC TTT       945
Gln Leu Ser Asp Glu Lys Ile Ile Asn Ile Val Leu Asp Leu Phe
```

```
                    305                 310                 315
GGA GCT GGG TTT GAC ACA GTC ACA ACT GCT ATC TCC TGG AGC CTC        990
Gly Ala Gly Phe Asp Thr Val Thr Thr Ala Ile Ser Trp Ser Leu
                    320                 325                 330

ATG TAT TTG GTG ATG AAC CCC AGG GTA CAG AGA AAG ATC CAA GAG       1035
Met Tyr Leu Val Met Asn Pro Arg Val Gln Arg Lys Ile Gln Glu
                    335                 340                 345

GAG CTC GAC ACA GTG ATT GGC AGG TCA CGG CGG CCC CGG CTC TCT       1080
Glu Leu Asp Thr Val Ile Gly Arg Ser Arg Arg Pro Arg Leu Ser
                    350                 355                 360

GAC AGA TCC CAT CTG CCC TAT ATG GAG GCC TTC ATC CTG GAG ACC       1125
Asp Arg Ser His Leu Pro Tyr Met Glu Ala Phe Ile Leu Glu Thr
                    365                 370                 375

TTC CGA CAC TCT TCC TTC GTC CCC TTC ACC ATC CCC CAC AGC ACA       1170
Phe Arg His Ser Ser Phe Val Pro Phe Thr Ile Pro His Ser Thr
                    380                 385                 390

ACA AGA GAC ACA AGT TTG AAA GGC TTT TAC ATC CCC AAG GGG CGT       1215
Thr Arg Asp Thr Ser Leu Lys Gly Phe Tyr Ile Pro Lys Gly Arg
                    395                 400                 405

TGT GTC TTT GTA AAC CAG TGG CAG ATC AAC CAT GAC CAG AAG CTA       1260
Cys Val Phe Val Asn Gln Trp Gln Ile Asn His Asp Gln Lys Leu
                    410                 415                 420

TGG GTC AAC CCA TCT GAG TTC CTA CCT GAA CGG TTT CTC ACC CCT       1305
Trp Val Asn Pro Ser Glu Phe Leu Pro Glu Arg Phe Leu Thr Pro
                    425                 430                 435

GAT GGT GCT ATC GAC AAG GTG TTA AGT GAG AAG GTG ATT ATC TTT       1350
Asp Gly Ala Ile Asp Lys Val Leu Ser Glu Lys Val Ile Ile Phe
                    440                 445                 450

GGC ATG GGC AAG CGG AAG TGT ATC GGT GAG ACC ATT GCC CGC TGG       1395
Gly Met Gly Lys Arg Lys Cys Ile Gly Glu Thr Ile Ala Arg Trp
                    455                 460                 465

GAG GTC TTT CTC TTC CTG GCT ATC CTG CTG CAA CGG GTG GAA TTC       1440
Glu Val Phe Leu Phe Leu Ala Ile Leu Leu Gln Arg Val Glu Phe
                    470                 475                 480

AGC GTG CCA CTG GGC GTG AAG GTG GAC ATG ACC CCC ATC TAT GGG       1485
Ser Val Pro Leu Gly Val Lys Val Asp Met Thr Pro Ile Tyr Gly
                    485                 490                 495

CTA ACC ATG AAG CAT GCC TGC TGT GAG CAC TTC CAA ATG CAG CTG       1530
Leu Thr Met Lys His Ala Cys Cys Glu His Phe Gln Met Gln Leu
                    500                 505                 510

CGC TCT TAG                                                       1539
Arg Ser ***

(2) INFORMATION FOR SEQ ID NO: 7:

(i) SEQUENCE CHARACTERISTICS:
        (A) LENGTH: 1539
        (B) TYPE: nucleic acid
        (C) STRANDEDNESS: double
        (D) TOPOLOGY: linear (ii) SEQUENCE DESCRIPTION: SEQ ID NO: 7:

ATG CTT TTC CCA ATC TCC ATG TCG GCC ACG GAG TTT CTT CTG GCC         45
Met Leu Phe Pro Ile Ser Met Ser Ala Thr Glu Phe Leu Leu Ala
 1                   5                  10                  15

TCT GTC ATC TTC TGT CTG GTA TTC TGG GTA ATC AGG GCC TCA AGA         90
Ser Val Ile Phe Cys Leu Val Phe Trp Val Ile Arg Ala Ser Arg
                    20                  25                  30

CCT CAG GTC CCC AAA GGC CTG AAG AAT CCA CCA GGG CCA TGG GGC        135
Pro Gln Val Pro Lys Gly Leu Lys Asn Pro Pro Gly Pro Trp Gly
                    35                  40                  45
```

```
TGG CCT CTG ATT GGG CAC ATG CTG ACC CTG GGA AAG AAC CCG CAC        180
Trp Pro Leu Ile Gly His Met Leu Thr Leu Gly Lys Asn Pro His
             50                  55                  60

CTG GCA CTG TCA AGG ATG AGC CAG CAG TAT GGG GAC GTG CTG CAG        225
Leu Ala Leu Ser Arg Met Ser Gln Gln Tyr Gly Asp Val Leu Gln
             65                  70                  75

ATC CGA ATT GGC TCC ACA CCC GTG GTG GTG CTG AGC GGC CTG GAC        270
Ile Arg Ile Gly Ser Thr Pro Val Val Val Leu Ser Gly Leu Asp
             80                  85                  90

ACC ATC CGG CAG GCC CTG GTG CGG CAG GGC GAT GAT TTC AAG GGC        315
Thr Ile Arg Gln Ala Leu Val Arg Gln Gly Asp Asp Phe Lys Gly
             95                 100                 105

CGG CCC GAC CTC TAC ACC TTC ACC CTC ATC AGT AAT GGT CAG AGC        360
Arg Pro Asp Leu Tyr Thr Phe Thr Leu Ile Ser Asn Gly Gln Ser
            110                 115                 120

ATG TCC TTC AGC CCA GAC TCT GGA CCA GTG TGG GCT GCC CGC CGG        405
Met Ser Phe Ser Pro Asp Ser Gly Pro Val Trp Ala Ala Arg Arg
            125                 130                 135

CGC CTG GCC CAG AAT GGC CTG AAA AGT TTC TCC ATT GCC TCT GAC        450
Arg Leu Ala Gln Asn Gly Leu Lys Ser Phe Ser Ile Ala Ser Asp
            140                 145                 150

CCA GCC TCC TCA ACC TCC TGC TAC CTG GAA GAG CAT GTG AGC AAG        495
Pro Ala Ser Ser Thr Ser Cys Tyr Leu Glu Glu His Val Ser Lys
            155                 160                 165

GAG GCT GAG GTC CTG ATA AGC ACG TTG CAG GAG CTG ATG GCA GGG        540
Glu Ala Glu Val Leu Ile Ser Thr Leu Gln Glu Leu Met Ala Gly
            170                 175                 180

CCT GGG CAC TTT AAC CCC TAC AGG TAT GTG GTG GTA TCA GTG ACC        585
Pro Gly His Phe Asn Pro Tyr Arg Tyr Val Val Val Ser Val Thr
            185                 190                 195

AAT GTC ATC TGT GCC ATT TGC TTT GGC CGG CGC TAT GAC CAC AAC        630
Asn Val Ile Cys Ala Ile Cys Phe Gly Arg Arg Tyr Asp His Asn
            200                 205                 210

CAC CAA GAA CTG CTT AGC CTA GTC AAC CTG AAT AAT AAT TTC GGG        675
His Gln Glu Leu Leu Ser Leu Val Asn Leu Asn Asn Asn Phe Gly
            215                 220                 225

GAG GTG GTT GGC TCT GGA AAC CCA GCT GAC TTC ATC CCT ATT CTT        720
Glu Val Val Gly Ser Gly Asn Pro Ala Asp Phe Ile Pro Ile Leu
            230                 235                 240

CGC TAC CTA CCC AAC CCT TCC CTG AAT GCC TTC AAG GAC CTG AAT        765
Arg Tyr Leu Pro Asn Pro Ser Leu Asn Ala Phe Lys Asp Leu Asn
            245                 250                 255

GAG AAG TTC TAC AGC TTC ATG CAG AAG ATG GTC AAG GAG CAC TAC        810
Glu Lys Phe Tyr Ser Phe Met Gln Lys Met Val Lys Glu His Tyr
            260                 265                 270

AAA ACC TTT GAG AAG GGC CAC ATC CGG GAC ATC ACA GAC AGC CTG        855
Lys Thr Phe Glu Lys Gly His Ile Arg Asp Ile Thr Asp Ser Leu
            275                 280                 285

ATT GAG CAC TGT CAG GAG AAG CAG CTG GAT GAG AAC GCC AAT GTC        900
Ile Glu His Cys Gln Glu Lys Gln Leu Asp Glu Asn Ala Asn Val
            290                 295                 300

CAG CTG TCA GAT GAG AAG ATC ATT AAC ATC GTC TTG GAC CTC TTT        945
Gln Leu Ser Asp Glu Lys Ile Ile Asn Ile Val Leu Asp Leu Phe
            305                 310                 315

GGA GCT GGG TTT GAC ACA GTC ACA ACT GCT ATC TCC TGG AGC CTC        990
Gly Ala Gly Phe Asp Thr Val Thr Thr Ala Ile Ser Trp Ser Leu
            320                 325                 330

ATG TAT TTG GTG ATG AAC CCC AGG GTA CAG AGA AAG ATC CAA GAG       1035
Met Tyr Leu Val Met Asn Pro Arg Val Gln Arg Lys Ile Gln Glu
```

```
                    335                 340                 345
GAG CTC GAC ACA GTG ATT GGC AGG TCA CGG CGG CCC CGG CTC TCT              1080
Glu Leu Asp Thr Val Ile Gly Arg Ser Arg Arg Pro Arg Leu Ser
                    350                 355                 360

GAC AGA TCC CAT CTG CCC TAT ATG GAG GCC TTC ATC CTG GAG ACC              1125
Asp Arg Ser His Leu Pro Tyr Met Glu Ala Phe Ile Leu Glu Thr
                    365                 370                 375

TTC CGA CAC TCT TCC TTC GTC CCC TTC ACC ATC CCC CAC AGC ACA              1170
Phe Arg His Ser Ser Phe Val Pro Phe Thr Ile Pro His Ser Thr
                    380                 385                 390

ACA AGA GAC ACA AGT TTG AAA GGC TTT TAC ATC CCC AAG GGG CGT              1215
Thr Arg Asp Thr Ser Leu Lys Gly Phe Tyr Ile Pro Lys Gly Arg
                    395                 400                 405

TGT GTC TTT GTA AAC CAG TGG CAG ATC AAC CAT GAC CAG AAG CTA              1260
Cys Val Phe Val Asn Gln Trp Gln Ile Asn His Asp Gln Lys Leu
                    410                 415                 420

TGG GTC AAC CCA TCT GAG TTC CTA CCT GAA CGG TTT CTC ACC CCT              1305
Trp Val Asn Pro Ser Glu Phe Leu Pro Glu Arg Phe Leu Thr Pro
                    425                 430                 435

GAT GGT GCT ATC GAC AAG GTG TTA AGT GAG AAG GTG ATT ATC TTT              1350
Asp Gly Ala Ile Asp Lys Val Leu Ser Glu Lys Val Ile Ile Phe
                    440                 445                 450

GGC ATG GGC AAG CGG AAG TGT ATC GGT GAG ACC GTT GCC CGC TGG              1395
Gly Met Gly Lys Arg Lys Cys Ile Gly Glu Thr Val Ala Arg Trp
                    455                 460                 465

GAG GTC TTT CTC TTC CTG GCT ATC CTG CTG CAA CGG GTG GAA TTC              1440
Glu Val Phe Leu Phe Leu Ala Ile Leu Leu Gln Arg Val Glu Phe
                    470                 475                 480

AGC GTG CCA CTG GGC GTG AAG GTG GAC ATG ACC CCC ATC TAT GGG              1485
Ser Val Pro Leu Gly Val Lys Val Asp Met Thr Pro Ile Tyr Gly
                    485                 490                 495

CTA ACC ATG AAG CAT GCC TGC TGT GAG CAC TTC CAA ATG CAG CTG              1530
Leu Thr Met Lys His Ala Cys Cys Glu His Phe Gln Met Gln Leu
                    500                 505                 510

CGC TCT TAG                                                              1539
Arg Ser ***

(2) INFORMATION FOR SEQ ID NO: 8:

(i) SEQUENCE CHARACTERISTICS:
        (A) LENGTH: 1485
        (B) TYPE: nucleic acid
        (C) STRANDEDNESS: double
        (D) TOPOLOGY: linear (ii) SEQUENCE DESCRIPTION: SEQ ID NO: 8:

ATG CTG GCC TCA GGG ATG CTT CTG GTG GCC TTG CTG GTC TGC CTG               45
Met Leu Ala Ser Gly Met Leu Leu Val Ala Leu Leu Val Cys Leu
  1                 5                  10                  15

ACT GTG ATG GTC TTG ATG TCT GTT TGG CAG CAG AGG AAG AGC AAG               90
Thr Val Met Val Leu Met Ser Val Trp Gln Gln Arg Lys Ser Lys
                    20                  25                  30

GGG AAG CTG CCT CCG GGA CCC ACC CCA TTG CCC TTC ATT GGA AAC              135
Gly Lys Leu Pro Pro Gly Pro Thr Pro Leu Pro Phe Ile Gly Asn
                    35                  40                  45

TAC CTG CAG CTG AAC ACA GAG CAG ATG TAC AAC TCC CTC ATG AAG              180
Tyr Leu Gln Leu Asn Thr Glu Gln Met Tyr Asn Ser Leu Met Lys
                    50                  55                  60

ATC AGT GAG CGC TAT GGC CCC GTG TTC ACC ATT CAC TTG GGG CCC              225
Ile Ser Glu Arg Tyr Gly Pro Val Phe Thr Ile His Leu Gly Pro
                    65                  70                  75
```

-continued

```
CGG CGG GTC GTG GTG CTG TGT GGA CAT GAT GCC GTC AGG GAG GCT        270
Arg Arg Val Val Val Leu Cys Gly His Asp Ala Val Arg Glu Ala
                80                  85                  90

CTG GTG GAC CAG GCT GAG GAG TTC AGC GGG CGA GGC GAG CAA GCC        315
Leu Val Asp Gln Ala Glu Glu Phe Ser Gly Arg Gly Glu Gln Ala
                95                  100                 105

ACC TTC GAC TGG GTC TTC AAA GGC TAT GGC GTG GTA TTC AGC AAC        360
Thr Phe Asp Trp Val Phe Lys Gly Tyr Gly Val Val Phe Ser Asn
                110                 115                 120

GGG GAG CGC GCC AAG CAG CTC CGG CGC TTC TCC ATC GCC ACC CTG        405
Gly Glu Arg Ala Lys Gln Leu Arg Arg Phe Ser Ile Ala Thr Leu
                125                 130                 135

CGG GAC TTC GGG GTG GGC AAG CGA GGC ATC GAG GAG CGC ATC CAG        450
Arg Asp Phe Gly Val Gly Lys Arg Gly Ile Glu Glu Arg Ile Gln
                140                 145                 150

GAG GAG GCG GGC TTC CTC ATC GAC GCC CTC CGG GGC ACT GGC GGC        495
Glu Glu Ala Gly Phe Leu Ile Asp Ala Leu Arg Gly Thr Gly Gly
                155                 160                 165

GCC AAT ATC GAT CCC ACC TTC TTC CTG AGC CGC ACA GTC TCC AAT        540
Ala Asn Ile Asp Pro Thr Phe Phe Leu Ser Arg Thr Val Ser Asn
                170                 175                 180

GTC ATC AGC TCC ATT GTC TTT GGG GAC CGC TTT GAC TAT AAG GAC        585
Val Ile Ser Ser Ile Val Phe Gly Asp Arg Phe Asp Tyr Lys Asp
                185                 190                 195

AAA GAG TTC CTG TCA CTG TTG CGC ATG ATG CTA GGA ATC TTC CAG        630
Lys Glu Phe Leu Ser Leu Leu Arg Met Met Leu Gly Ile Phe Gln
                200                 205                 210

TTC ACG TCA ACC TCC ACG GGG CAG CTC TAT GAG ATG TTC TCT TCG        675
Phe Thr Ser Thr Ser Thr Gly Gln Leu Tyr Glu Met Phe Ser Ser
                215                 220                 225

GTG ATG AAA CAC CTG CCA GGA CCA CAG CAA CAG GCC TTT CAG TTG        720
Val Met Lys His Leu Pro Gly Pro Gln Gln Gln Ala Phe Gln Leu
                230                 235                 240

CTG CAA GGG CTG GAG GAC TTC ATA GCC AAG AAG GTG GAG CAC AAC        765
Leu Gln Gly Leu Glu Asp Phe Ile Ala Lys Lys Val Glu His Asn
                245                 250                 255

CAG CGC ACG CTG GAT CCC AAT TCC CCA CGG GAC TTC ATT GAC TCC        810
Gln Arg Thr Leu Asp Pro Asn Ser Pro Arg Asp Phe Ile Asp Ser
                260                 265                 270

TTT CTC ATC CGC ATG CAG GAG GAG GAG AAG AAC CCC AAC ACG GAG        855
Phe Leu Ile Arg Met Gln Glu Glu Glu Lys Asn Pro Asn Thr Glu
                275                 280                 285

TTC TAC TTG AAA AAC CTG GTG ATG ACC ACG TTG AAC CTC TTC ATT        900
Phe Tyr Leu Lys Asn Leu Val Met Thr Thr Leu Asn Leu Phe Ile
                290                 295                 300

GGG GGC ACC GAG ACC GTC AGC ACC ACC CTG CGC TAT GGC TTC TTG        945
Gly Gly Thr Glu Thr Val Ser Thr Thr Leu Arg Tyr Gly Phe Leu
                305                 310                 315

CTG CTC ATG AAG CAC CCA GAG GTG GAG GCC AAG GTC CAT GAG GAG        990
Leu Leu Met Lys His Pro Glu Val Glu Ala Lys Val His Glu Glu
                320                 325                 330

ATT GAC AGA GTG ATC GGC AAG AAC CGG CAG CCC AAG TTT GAG GAC        1035
Ile Asp Arg Val Ile Gly Lys Asn Arg Gln Pro Lys Phe Glu Asp
                335                 340                 345

CGG GCC AAG ATG CCC TAC ATG GAG GCA GTG ATC CAC GAG ATC CAA        1080
Arg Ala Lys Met Pro Tyr Met Glu Ala Val Ile His Glu Ile Gln
                350                 355                 360

AGA TTT GGA GAC GTG ATC CCC ATG AGT TTG GCC CGC AGA GTC AAA        1125
Arg Phe Gly Asp Val Ile Pro Met Ser Leu Ala Arg Arg Val Lys
```

-continued

```
                    365                 370                 375
AAG GAC ACC AAG TTT CGG GAT TTC TTC CTC CCT AAG GGC ACC GAA           1170
Lys Asp Thr Lys Phe Arg Asp Phe Phe Leu Pro Lys Gly Thr Glu
                380                 385                 390

GTG TAC CCT ATG CTG GGC TCT GTG CTG AGA GAC CCC AGT TTC TTC           1215
Val Tyr Pro Met Leu Gly Ser Val Leu Arg Asp Pro Ser Phe Phe
                395                 400                 405

TCC AAC CCC CAG GAC TTC AAT CCC CAG CAC TTC CTG AAT GAG AAG           1260
Ser Asn Pro Gln Asp Phe Asn Pro Gln His Phe Leu Asn Glu Lys
                410                 415                 420

GGG CAG TTT AAG AAG AGT GAT GCT TTT GTG CCC TTT TCC ATC GGA           1305
Gly Gln Phe Lys Lys Ser Asp Ala Phe Val Pro Phe Ser Ile Gly
                425                 430                 435

AAG CGG AAC TGT TTC GGA GAA GGC CTG GCC AGA ATG GAG CTC TTT           1350
Lys Arg Asn Cys Phe Gly Glu Gly Leu Ala Arg Met Glu Leu Phe
                440                 445                 450

CTC TTC TTC ACC ACC GTC ATG CAG AAC TTC CGC CTC AAG TCC TCC           1395
Leu Phe Phe Thr Thr Val Met Gln Asn Phe Arg Leu Lys Ser Ser
                455                 460                 465

CAG TCA CCT AAG GAC ATT GAC GTG TCC CCC AGA CAC GTG GGC TTT           1440
Gln Ser Pro Lys Asp Ile Asp Val Ser Pro Arg His Val Gly Phe
                470                 475                 480

GCC ACG ATC CCA CGA AAC TAC ACC ATG AGC TTC CTG CCC CGC TGA           1485
Ala Thr Ile Pro Arg Asn Tyr Thr Met Ser Phe Leu Pro Arg ***
                485                 490                 495

(2) INFORMATION FOR SEQ ID NO: 9:

(i) SEQUENCE CHARACTERISTICS:
        (A) LENGTH: 1485
        (B) TYPE: nucleic acid
        (C) STRANDEDNESS: double
        (D) TOPOLOGY: linear (ii) SEQUENCE DESCRIPTION: SEQ ID NO: 9:

ATG CTG GCC TCA GGG ATG CTT CTG GTG GCC TTG CTG GTC TGC CTG             45
Met Leu Ala Ser Gly Met Leu Leu Val Ala Leu Leu Val Cys Leu
 1               5                  10                  15

ACT GTG ATG GTC TTG ATG TCT GTT TGG CAG CAG AGG AAG AGC AAG             90
Thr Val Met Val Leu Met Ser Val Trp Gln Gln Arg Lys Ser Lys
                20                  25                  30

GGG AAG CTG CCT CCG GGA CCC ACC CCA TTG CCC TTC ATT GGA AAC            135
Gly Lys Leu Pro Pro Gly Pro Thr Pro Leu Pro Phe Ile Gly Asn
                35                  40                  45

TAC CTG CAG CTG AAC ACA GAG CAG ATG TAC AAC TCC CTC ATG AAG            180
Tyr Leu Gln Leu Asn Thr Glu Gln Met Tyr Asn Ser Leu Met Lys
                50                  55                  60

ATC AGT GAG CGC TAT GGC CCC GTG TTC ACC ATT CAC TTG GGG CCC            225
Ile Ser Glu Arg Tyr Gly Pro Val Phe Thr Ile His Leu Gly Pro
                65                  70                  75

CGG CGG GTC GTG GTG CTG TGT GGA CAT GAT GCC GTC AGG GAG GCT            270
Arg Arg Val Val Val Leu Cys Gly His Asp Ala Val Arg Glu Ala
                80                  85                  90

CTG GTG GAC CAG GCT GAG GAG TTC AGC GGG CGA GGC GAG CAA GCC            315
Leu Val Asp Gln Ala Glu Glu Phe Ser Gly Arg Gly Glu Gln Ala
                95                  100                 105

ACC TTC GAC TGG GTC TTC AAA GGC TAT GGC GTG GTA TTC AGC AAC            360
Thr Phe Asp Trp Val Phe Lys Gly Tyr Gly Val Val Phe Ser Asn
                110                 115                 120

GGG GAG CGC GCC AAG CAG CTC CGG CGC TTC TCC ATC GCC ACC CTG            405
Gly Glu Arg Ala Lys Gln Leu Arg Arg Phe Ser Ile Ala Thr Leu
```

-continued

|  |  |  | 125 |  |  |  | 130 |  |  |  | 135 |  |  |
|---|---|---|---|---|---|---|---|---|---|---|---|---|---|

```
CGG GAC TTC GGG GTG GGC AAG CGA GGC ATC GAG GAG CGC ATC CAG           450
Arg Asp Phe Gly Val Gly Lys Arg Gly Ile Glu Glu Arg Ile Gln
            140                 145                 150

GAG GAG GCG GGC TTC CTC ATC GAC GCC CTC CGG GGC ACT GGC GGC           495
Glu Glu Ala Gly Phe Leu Ile Asp Ala Leu Arg Gly Thr Gly Gly
            155                 160                 165

GCC AAT ATC GAT CCC ACC TTC TTC CTG AGC CGC ACA GTC TCC AAT           540
Ala Asn Ile Asp Pro Thr Phe Phe Leu Ser Arg Thr Val Ser Asn
            170                 175                 180

GTC ATC AGC TCC ATT GTC TTT GGG GAC CGC TTT GAC TAT AAG GAC           585
Val Ile Ser Ser Ile Val Phe Gly Asp Arg Phe Asp Tyr Lys Asp
            185                 190                 195

AAA GAG TTC CTG TCA CTG TTG CGC ATG ATG CTA GGA ATC TTC CAG           630
Lys Glu Phe Leu Ser Leu Leu Arg Met Met Leu Gly Ile Phe Gln
            200                 205                 210

TTC ACG TCA ACC TCC ACG GGG CAG CTC TAT GAG ATG TTC TCT TCG           675
Phe Thr Ser Thr Ser Thr Gly Gln Leu Tyr Glu Met Phe Ser Ser
            215                 220                 225

GTG ATG AAA CAC CTG CCA GGA CCA CAG CAA CAG GCC TTT CAG TTG           720
Val Met Lys His Leu Pro Gly Pro Gln Gln Gln Ala Phe Gln Leu
            230                 235                 240

CTG CAA GGG CTG GAG GAC TTC ATA GCC AAG AAG GTG GAG CAC AAC           765
Leu Gln Gly Leu Glu Asp Phe Ile Ala Lys Lys Val Glu His Asn
            245                 250                 255

CAG CGC ACG CTG GAT CCC AAT TCC CCA CGG GAC TTC ATT GAC TCC           810
Gln Arg Thr Leu Asp Pro Asn Ser Pro Arg Asp Phe Ile Asp Ser
            260                 265                 270

TTT CTC ATC CGC ATG CAG GAG GAG GAG AAG AAC CCC AAC ACG GAG           855
Phe Leu Ile Arg Met Gln Glu Glu Glu Lys Asn Pro Asn Thr Glu
            275                 280                 285

TTC TAC TTG AAA AAC CTG GTG ATG ACC ACG TTG AAC CTC TTC ATT           900
Phe Tyr Leu Lys Asn Leu Val Met Thr Thr Leu Asn Leu Phe Ile
            290                 295                 300

GGG GGC ACC GAG ACC GTC AGC ACC ACC CTG CGC TAT GGC TTC TTG           945
Gly Gly Thr Glu Thr Val Ser Thr Thr Leu Arg Tyr Gly Phe Leu
            305                 310                 315

CTG CTC ATG AAG CAC CCA GAG GTG GAG GCC AAG GTC CAT GAG GAG           990
Leu Leu Met Lys His Pro Glu Val Glu Ala Lys Val His Glu Glu
            320                 325                 330

ATT GAC AGA GTG ATC GGC AAG AAC CGG CAG CCC AAG TTT GAG GAC          1035
Ile Asp Arg Val Ile Gly Lys Asn Arg Gln Pro Lys Phe Glu Asp
            335                 340                 345

CGG GCC AAG ATG CCC TAC ATG GAG GCA GTG ATC CAC GAG ATC CAA          1080
Arg Ala Lys Met Pro Tyr Met Glu Ala Val Ile His Glu Ile Gln
            350                 355                 360

AGA TTT GGA GAC GTG ATC CCC ATG AGT TTG GCC CGC AGA GTC AAA          1125
Arg Phe Gly Asp Val Ile Pro Met Ser Leu Ala Arg Arg Val Lys
            365                 370                 375

AAG GAC ACC AAG TTT CGG GAT TTC TTC CTC CCT AAG GGC ACC GAA          1170
Lys Asp Thr Lys Phe Arg Asp Phe Phe Leu Pro Lys Gly Thr Glu
            380                 385                 390

GTG TAC CCT ATG CTG GGC TCT GTG CTG AGA GAC CCC AGT TTC TTC          1215
Val Tyr Pro Met Leu Gly Ser Val Leu Arg Asp Pro Ser Phe Phe
            395                 400                 405

TCC AAC CCC CAG GAC TTC AAT CCC CAG CAC TTC CTG AAT GAG AAG          1260
Ser Asn Pro Gln Asp Phe Asn Pro Gln His Phe Leu Asn Glu Lys
            410                 415                 420

GGG CAG TTT AAG AAG AGT GAT GCT TTT GTG CCC TTT TCC ATC GGA          1305
```

```
Gly Gln Phe Lys Lys Ser Asp Ala Phe Val Pro Phe Ser Ile Gly
            425                 430                 435

AAG CGG AAC TGT TTC GGA AAA GGC CTG GCC AGA ATG GAG CTC TTT          1350
Lys Arg Asn Cys Phe Gly Glu Gly Leu Ala Arg Met Glu Leu Phe
                440                 445                 450

CTC TTC TTC ACC ACC GTC ATG CAG AAC TTC CGC CTC AAG TCC TCC          1395
Leu Phe Phe Thr Thr Val Met Gln Asn Phe Arg Leu Lys Ser Ser
                455                 460                 465

CAG TCA CCT AAG GAC ATT GAC GTG TCC CCC AAA CAC GTG GGC TTT          1440
Gln Ser Pro Lys Asp Ile Asp Val Ser Pro Lys His Val Gly Phe
                470                 475                 480

GCC ACG ATC CCA CGA AAC TAC ACC ATG AGC TTC CTG CCC CGC TGA          1485
Ala Thr Ile Pro Arg Asn Tyr Thr Met Ser Phe Leu Pro Arg ***
                485                 490                 495

(2) INFORMATION FOR SEQ ID NO: 10:

(i) SEQUENCE CHARACTERISTICS:
        (A) LENGTH: 1476
        (B) TYPE: nucleic acid
        (C) STRANDEDNESS: double
        (D) TOPOLOGY: linear (ii) SEQUENCE DESCRIPTION: SEQ ID NO: 10:

ATG GAA CTC AGC GTC CTC CTC TTC CTT GCA CTC CTC ACA GGA CTC           45
Met Glu Leu Ser Val Leu Leu Phe Leu Ala Leu Leu Thr Gly Leu
 1               5                  10                  15

TTG CTA CTC CTG GTT CAG CGC CAC CCT AAC ACC CAT GAC CGC CTC           90
Leu Leu Leu Leu Val Gln Arg His Pro Asn Thr His Asp Arg Leu
                20                  25                  30

CCA CCA GGG CCC CGC CCT CTG CCC CTT TTG GGA AAC CTT CTG CAG          135
Pro Pro Gly Pro Arg Pro Leu Pro Leu Leu Gly Asn Leu Leu Gln
                35                  40                  45

ATG GAT AGA AGA GGC CTA CTC AAA TCC TTT CTG AGG TTC CGA GAG          180
Met Asp Arg Arg Gly Leu Leu Lys Ser Phe Leu Arg Phe Arg Glu
                50                  55                  60

AAA TAT GGG GAC GTC TTC ACG GTA CAC CTG GGA CCG AGG CCC GTG          225
Lys Tyr Gly Asp Val Phe Thr Val His Leu Gly Pro Arg Pro Val
                65                  70                  75

GTC ATG CTG TGT GGA GTA GAG GCC ATA CGG GAG GCC CTT GTG GAC          270
Val Met Leu Cys Gly Val Glu Ala Ile Arg Glu Ala Leu Val Asp
                80                  85                  90

AAG GCT GAG GCC TTC TCT GGC CGG GGA AAA ATC GCC ATG GTC GAC          315
Lys Ala Glu Ala Phe Ser Gly Arg Gly Lys Ile Ala Met Val Asp
                95                  100                 105

CCA TTC TTC CGG GGA TAT GGT GTG ATC TTT GCC AAT GGA AAC CGC          360
Pro Phe Phe Arg Gly Tyr Gly Val Ile Phe Ala Asn Gly Asn Arg
                110                 115                 120

TGG AAG GTG CTT CGG CGA TTC TCT GTG ACC ACT ATG AGG GAC TTC          405
Trp Lys Val Leu Arg Arg Phe Ser Val Thr Thr Met Arg Asp Phe
                125                 130                 135

GGG ATG GGA AAG CGG AGT GTG GAG GAG CGG ATT CAG GAG GAG GCT          450
Gly Met Gly Lys Arg Ser Val Glu Glu Arg Ile Gln Glu Glu Ala
                140                 145                 150

CAG TGT CTG ATA GAG GAG CTT CGG AAA TCC AAG GGG GCC CTC ATG          495
Gln Cys Leu Ile Glu Glu Leu Arg Lys Ser Lys Gly Ala Leu Met
                155                 160                 165

GAC CCC ACC TTC CTC TTC CAG TCC ATT ACC GCC AAC ATC ATC TGC          540
Asp Pro Thr Phe Leu Phe Gln Ser Ile Thr Ala Asn Ile Ile Cys
                170                 175                 180

TCC ATC GTC TTT GGA AAA CGA TTC CAC TAC CAA GAT CAA GAG TTC          585
```

```
                                                         -continued

Ser Ile Val Phe Gly Lys Arg Phe His Tyr Gln Asp Gln Glu Phe
            185                 190                 195

CTG AAG ATG CTG AAC TTG TTC TAC CAG ACT TTT TCA CTC ATC AGC       630
Leu Lys Met Leu Asn Leu Phe Tyr Gln Thr Phe Ser Leu Ile Ser
            200                 205                 210

TCT GTA TTC GGC CAG CTG TTT GAG CTC TTC TCT GGC TTC TTG AAA       675
Ser Val Phe Gly Gln Leu Phe Glu Leu Phe Ser Gly Phe Leu Lys
            215                 220                 225

TAC TTT CCT GGG GCA CAC AGG CAA GTT TAC AAA AAC CTG CAG GAA       720
Tyr Phe Pro Gly Ala His Arg Gln Val Tyr Lys Asn Leu Gln Glu
            230                 235                 240

ATC AAT GCT TAC ATT GGC CAC AGT GTG GAG AAG CAC CGT GAA ACC       765
Ile Asn Ala Tyr Ile Gly His Ser Val Glu Lys His Arg Glu Thr
            245                 250                 255

CTG GAC CCC AGC GCC CCC AAG GAC CTC ATC GAC ACC TAC CTG CTC       810
Leu Asp Pro Ser Ala Pro Lys Asp Leu Ile Asp Thr Tyr Leu Leu
            260                 265                 270

CAC ATG GAA AAA GAG AAA TCC AAC GCA CAC AGT GAA TTC AGC CAC       855
His Met Glu Lys Glu Lys Ser Asn Ala His Ser Glu Phe Ser His
            275                 280                 285

CAG AAC CTC AAC CTC AAC ACG CTC TCG CTC TTC TTT GCT GGC ACT       900
Gln Asn Leu Asn Leu Asn Thr Leu Ser Leu Phe Phe Ala Gly Thr
            290                 295                 300

GAG ACC ACC AGC ACC ACT CTC CGC TAC GGC TTC CTG CTC ATG CTC       945
Glu Thr Thr Ser Thr Thr Leu Arg Tyr Gly Phe Leu Leu Met Leu
            305                 310                 315

AAA TAC CCT CAT GTT GCA GAG AGA GTC TAC AGG GAG ATT GAA CAG       990
Lys Tyr Pro His Val Ala Glu Arg Val Tyr Arg Glu Ile Glu Gln
            320                 325                 330

GTG ATT GGC CCA CAT CGC CCT CCA GAG CTT CAT GAC CGA GCC AAA      1035
Val Ile Gly Pro His Arg Pro Pro Glu Leu His Asp Arg Ala Lys
            335                 340                 345

ATG CCA TAC ACA GAG GCA GTC ATC TAT GAG ATT CAG AGA TTT TCC      1080
Met Pro Tyr Thr Glu Ala Val Ile Tyr Glu Ile Gln Arg Phe Ser
            350                 355                 360

GAC CTT CTC CCC ATG GGT GTG CCC CAC ATT GTC ACC CAA CAC ACC      1125
Asp Leu Leu Pro Met Gly Val Pro His Ile Val Thr Gln His Thr
            365                 370                 375

AGC TTC CGA GGG TAC ATC ATC CCC AAG GAC ACA GAA GTA TTT CTC      1170
Ser Phe Arg Gly Tyr Ile Ile Pro Lys Asp Thr Glu Val Phe Leu
            380                 385                 390

ATC CTG AGC ACT GCT CTC CAT GAC CCA CAC TAC TTT GAA AAA CCA      1215
Ile Leu Ser Thr Ala Leu His Asp Pro His Tyr Phe Glu Lys Pro
            395                 400                 405

GAC GCC TTC AAT CCT GAC CAC TTT CTG GAT GCC AAT GGG GCA CTG      1260
Asp Ala Phe Asn Pro Asp His Phe Leu Asp Ala Asn Gly Ala Leu
            410                 415                 420

AAA AAG ACT GAA GCT TTT ATC CCC TTC TCC TTA GGG AAG CGG ATT      1305
Lys Lys Thr Glu Ala Phe Ile Pro Phe Ser Leu Gly Lys Arg Ile
            425                 430                 435

TGT CTT GGT GAA GGC ATC GCC CGT GCG GAA TTG TTC CTC TTC TTC      1350
Cys Leu Gly Glu Gly Ile Ala Arg Ala Glu Leu Phe Leu Phe Phe
            440                 445                 450

ACC ACC ATC CTC CAG AAC TTC TCC ATG GCC AGC CCC GTG GCC CCA      1395
Thr Thr Ile Leu Gln Asn Phe Ser Met Ala Ser Pro Val Ala Pro
            455                 460                 465

GAA GAC ATC GAT CTG ACA CCC CAG GAG TGT GGT GTG GGC AAA ATA      1440
Glu Asp Ile Asp Leu Thr Pro Gln Glu Cys Gly Val Gly Lys Ile
            470                 475                 480
```

```
CCC CCA ACA TAC CAG ATC CGC TTC CTG CCC CGC TGA                                    1476
Pro Pro Thr Tyr Gln Ile Arg Phe Leu Pro Arg ***
            485                 490
```

(2) INFORMATION FOR SEQ ID NO: 11:

(i) SEQUENCE CHARACTERISTICS:
        (A) LENGTH: 1473
        (B) TYPE: nucleic acid
        (C) STRANDEDNESS: double
        (D) TOPOLOGY: linear (ii) SEQUENCE DESCRIPTION: SEQ ID NO: 11:

```
ATG GAA CCT TTT GTG GTC CTG GTG CTG TGT CTC TCT TTT ATG CTT                         45
Met Glu Pro Phe Val Val Leu Val Leu Cys Leu Ser Phe Met Leu
 1               5                  10                  15

CTC TTT TCA CTC TGG AGA CAG AGC TGT AGG AGA AGG AAG CTC CCT                         90
Leu Phe Ser Leu Trp Arg Gln Ser Cys Arg Arg Arg Lys Leu Pro
                20                  25                  30

CCT GGC CCC ACT CCT CTT CCT ATT ATT GGA AAT ATG CTA CAG ATA                        135
Pro Gly Pro Thr Pro Leu Pro Ile Ile Gly Asn Met Leu Gln Ile
                35                  40                  45

GAT GTT AAG GAC ATC TGC AAA TCT TTC ACC AAT TTC TCA AAA GTC                        180
Asp Val Lys Asp Ile Cys Lys Ser Phe Thr Asn Phe Ser Lys Val
                50                  55                  60

TAT GGT CCT GTG TTC ACC GTG TAT TTT GGC ATG AAT CCC ATA GTG                        225
Tyr Gly Pro Val Phe Thr Val Tyr Phe Gly Met Asn Pro Ile Val
                65                  70                  75

GTG TTT CAT GGA TAT GAG GCA GTG AAG GAA GCC CTG ATT GAT AAT                        270
Val Phe His Gly Tyr Glu Ala Val Lys Glu Ala Leu Ile Asp Asn
                80                  85                  90

GGA GAG GAG TTT TCT GGA AGA GGC AAT TCC CCA ATA TCT CAA AGA                        315
Gly Glu Glu Phe Ser Gly Arg Gly Asn Ser Pro Ile Ser Gln Arg
                95                 100                 105

ATT ACT AAA GGA CTT GGA ATC ATT TCC AGC AAT GGA AAG AGA TGG                        360
Ile Thr Lys Gly Leu Gly Ile Ile Ser Ser Asn Gly Lys Arg Trp
               110                 115                 120

AAG GAG ATC CGG CGT TTC TCC CTC ACA ACC TTG CGG AAT TTT GGG                        405
Lys Glu Ile Arg Arg Phe Ser Leu Thr Thr Leu Arg Asn Phe Gly
               125                 130                 135

ATG GGG AAG AGG AGC ATT GAG GAC CGT GTT CAA GAG GAA GCT CAC                        450
Met Gly Lys Arg Ser Ile Glu Asp Arg Val Gln Glu Glu Ala His
               140                 145                 150

TGC CTT GTG GAG GAG TTG AGA AAA ACC AAG GCT TCA CCC TGT GAT                        495
Cys Leu Val Glu Glu Leu Arg Lys Thr Lys Ala Ser Pro Cys Asp
               155                 160                 165

CCC ACT TTC ATC CTG GGC TGT GCT CCC TGC AAT GTG ATC TGC TCC                        540
Pro Thr Phe Ile Leu Gly Cys Ala Pro Cys Asn Val Ile Cys Ser
               170                 175                 180

GTT GTT TTC CAG AAA CGA TTT GAT TAT AAA GAT CAG AAT TTT CTC                        585
Val Val Phe Gln Lys Arg Phe Asp Tyr Lys Asp Gln Asn Phe Leu
               185                 190                 195

ACC CTG ATG AAA AGA TTC AAT GAA AAC TTC AGG ATT CTG AAC TCC                        630
Thr Leu Met Lys Arg Phe Asn Glu Asn Phe Arg Ile Leu Asn Ser
               200                 205                 210

CCA TGG ATC CAG GTC TGC AAT AAT TTC CCT CTA CTC ATT GAT TGT                        675
Pro Trp Ile Gln Val Cys Asn Asn Phe Pro Leu Leu Ile Asp Cys
               215                 220                 225

TTC CCA GGA ACT CAC AAC AAA GTG CTT AAA AAT GTT GCT CTT ACA                        720
Phe Pro Gly Thr His Asn Lys Val Leu Lys Asn Val Ala Leu Thr
               230                 235                 240
```

```
CGA AGT TAC ATT AGG GAG AAA GTA AAA GAA CAC CAA GCA TCA CTG         765
Arg Ser Tyr Ile Arg Glu Lys Val Lys Glu His Gln Ala Ser Leu
            245                 250                 255

GAT GTT AAC AAT CCT CGG GAC TTT ATC GAT TGC TTC CTG ATC AAA         810
Asp Val Asn Asn Pro Arg Asp Phe Ile Asp Cys Phe Leu Ile Lys
            260                 265                 270

ATG GAG CAG GAA AAG GAC AAC CAA AAG TCA GAA TTC AAT ATT GAA         855
Met Glu Gln Glu Lys Asp Asn Gln Lys Ser Glu Phe Asn Ile Glu
            275                 280                 285

AAC TTG GTT GGC ACT GTA GCT GAT CTA TTT GTT GCT GGA ACA GAG         900
Asn Leu Val Gly Thr Val Ala Asp Leu Phe Val Ala Gly Thr Glu
            290                 295                 300

ACA ACA AGC ACC ACT CTG AGA TAT GGA CTC CTC CTG CTG AAG             945
Thr Thr Ser Thr Thr Leu Arg Tyr Gly Leu Leu Leu Leu Lys
            305                 310                 315

CAC CCA GAG GTC ACA GCT AAA GTC CAG GAA GAG ATT GAT CAT GTA         990
His Pro Glu Val Thr Ala Lys Val Gln Glu Glu Ile Asp His Val
            320                 325                 330

ATT GGC AGA CAC AGG AGC CCC TGC ATG CAG GAT AGG AGC CAC ATG        1035
Ile Gly Arg His Arg Ser Pro Cys Met Gln Asp Arg Ser His Met
            335                 340                 345

CCT TAC ACT GAT GCT GTA GTG CAC GAG ATC CAG AGA TAC AGT GAC        1080
Pro Tyr Thr Asp Ala Val Val His Glu Ile Gln Arg Tyr Ser Asp
            350                 355                 360

CTT GTC CCC ACC GGT GTG CCC CAT GCA GTG ACC ACT GAT ACT AAG        1125
Leu Val Pro Thr Gly Val Pro His Ala Val Thr Thr Asp Thr Lys
            365                 370                 375

TTC AGA AAC TAC CTC ATC CCC AAG GGC ACA ACC ATA ATG GCA TTA        1170
Phe Arg Asn Tyr Leu Ile Pro Lys Gly Thr Thr Ile Met Ala Leu
            380                 385                 390

CTG ACT TCC GTG CTA CAT GAT GAC AAA GAA TTT CCT AAT CCA AAT        1215
Leu Thr Ser Val Leu His Asp Asp Lys Glu Phe Pro Asn Pro Asn
            395                 400                 405

ATC TTT GAC CCT GGC CAC TTT CTA GAT AAG AAT GGC AAC TTT AAG        1260
Ile Phe Asp Pro Gly His Phe Leu Asp Lys Asn Gly Asn Phe Lys
            410                 415                 420

AAA AGT GAC TAC TTC ATG CCT TTC TCA GCA GGA AAA CGA ATT TGT        1305
Lys Ser Asp Tyr Phe Met Pro Phe Ser Ala Gly Lys Arg Ile Cys
            425                 430                 435

GCA GGA GAA GGA CTT GCC CGC ATG GAG CTA TTT TTA TTT CTA ACC        1350
Ala Gly Glu Gly Leu Ala Arg Met Glu Leu Phe Leu Phe Leu Thr
            440                 445                 450

ACA ATT TTA CAG AAC TTT AAC CTG AAA TCT GTT GAT GAT TTA AAG        1395
Thr Ile Leu Gln Asn Phe Asn Leu Lys Ser Val Asp Asp Leu Lys
            455                 460                 465

AAC CTC AAT ACT ACT GCA GTT ACC AAA GGG ATT GTT TCT CTG CCA        1440
Asn Leu Asn Thr Thr Ala Val Thr Lys Gly Ile Val Ser Leu Pro
            470                 475                 480

CCC TCA TAC CAG ATC TGC TTC ATC CCT GTC TGA                        1473
Pro Ser Tyr Gln Ile Cys Phe Ile Pro Val ***
            485                 490
```

(2) INFORMATION FOR SEQ ID NO: 12:

(i) SEQUENCE CHARACTERISTICS:
        (A) LENGTH: 1473
        (B) TYPE: nucleic acid
        (C) STRANDEDNESS: double
        (D) TOPOLOGY: linear (ii) SEQUENCE DESCRIPTION: SEQ ID NO: 12:

```
ATG GAA CCT TTT GTG GTC CTG GTG CTG TGT CTC TCT TTT ATG CTT         45
Met Glu Pro Phe Val Val Leu Val Leu Cys Leu Ser Phe Met Leu
 1               5                  10                  15

CTC TTT TCA CTC TGG AGA CAG AGC TGT AGG AGA AGG AAG CTC CCT         90
Leu Phe Ser Leu Trp Arg Gln Ser Cys Arg Arg Arg Lys Leu Pro
             20                  25                  30

CCT GGC CCC ACT CCT CTT CCT ATT ATT GGA AAT ATG CTA CAG ATA        135
Pro Gly Pro Thr Pro Leu Pro Ile Ile Gly Asn Met Leu Gln Ile
                 35                  40                  45

GAT GTT AAG GAC ATC TGC AAA TCT TTC ACC AAT TTC TCA AAA GTC        180
Asp Val Lys Asp Ile Cys Lys Ser Phe Thr Asn Phe Ser Lys Val
                     50                  55                  60

TAT GGT CCT GTG TTC ACC GTG TAT TTT GGC ATG AAT CCC ATA GTG        225
Tyr Gly Pro Val Phe Thr Val Tyr Phe Gly Met Asn Pro Ile Val
                         65                  70                  75

GTG TTT CAT GGA TAT GAG GCA GTG AAG GAA GCC CTG ATT GAT AAT        270
Val Phe His Gly Tyr Glu Ala Val Lys Glu Ala Leu Ile Asp Asn
                             80                  85                  90

GGA GAG GAG TTT TCT GGA AGA GGC AAT TCC CCA ATA TCT CAA AGA        315
Gly Glu Glu Phe Ser Gly Arg Gly Asn Ser Pro Ile Ser Gln Arg
                                 95                 100                 105

ATT ACT AAA GGA CTT GGA ATC ATT TCC AGC AAT GGA AAG AGA TGG        360
Ile Thr Lys Gly Leu Gly Ile Ile Ser Ser Asn Gly Lys Arg Trp
                                    110                 115                 120

AAG GAG ATC CGG CGT TTC TCC CTC ACA ACC TTG CGG AAT TTT GGG        405
Lys Glu Ile Arg Arg Phe Ser Leu Thr Thr Leu Arg Asn Phe Gly
                                        125                 130                 135

ATG GGG AAG AAG AGC ATT GAG GAC CGT GTT CAA GAG GAA GCT CAC        450
Met Gly Lys Lys Ser Ile Glu Asp Arg Val Gln Glu Glu Ala His
                                            140                 145                 150

TGC CTT GTG GAG GAG TTG AGA AAA ACC AAG GCT TCA CCC TGT GAT        495
Cys Leu Val Glu Glu Leu Arg Lys Thr Lys Ala Ser Pro Cys Asp
                                                155                 160                 165

CCC ACT TTC ATC CTG GGC TGT GCT CCC TGC AAT GTG ATC TGC TCC        540
Pro Thr Phe Ile Leu Gly Cys Ala Pro Cys Asn Val Ile Cys Ser
                                                    170                 175                 180

GTT GTT TTC CAG AAA CGA TTT GAT TAT AAA GAT CAG AAT TTT CTC        585
Val Val Phe Gln Lys Arg Phe Asp Tyr Lys Asp Gln Asn Phe Leu
                                                        185                 190                 195

ACC CTG ATG AAA AGA TTC AAT GAA AAC TTC AGG ATT CTG AAC TCC        630
Thr Leu Met Lys Arg Phe Asn Glu Asn Phe Arg Ile Leu Asn Ser
                                                            200                 205                 210

CCA TGG ATC CAG GTC TGC AAT AAT TTC CCT CTA CTC ATT GAT TGT        675
Pro Trp Ile Gln Val Cys Asn Asn Phe Pro Leu Leu Ile Asp Cys
                                                                215                 220                 225

TTC CCA GGA ACT CAC AAC AAA GTG CTT AAA AAT GTT GCT CTT ACA        720
Phe Pro Gly Thr His Asn Lys Val Leu Lys Asn Val Ala Leu Thr
                                                                    230                 235                 240

CGA AGT TAC ATT AGG GAG AAA GTA AAA GAA CAC CAA GCA TCA CTG        765
Arg Ser Tyr Ile Arg Glu Lys Val Lys Glu His Gln Ala Ser Leu
                                                                        245                 250                 255

GAT GTT AAC AAT CCT CGG GAC TTT ATC GAT TGC TTC CTG ATC AAA        810
Asp Val Asn Asn Pro Arg Asp Phe Ile Asp Cys Phe Leu Ile Lys
                                                                            260                 265                 270

ATG GAG CAG GAA AAG GAC AAC CAA AAG TCA GAA TTC AAT ATT GAA        855
Met Glu Gln Glu Lys Asp Asn Gln Lys Ser Glu Phe Asn Ile Glu
                                                                                275                 280                 285

AAC TTG GTT GGC ACT GTA GCT GAT CTA TTT GTT GCT GGA ACA GAG        900
Asn Leu Val Gly Thr Val Ala Asp Leu Phe Val Ala Gly Thr Glu
                                                                                    290                 295                 300
```

```
ACA ACA AGC ACC ACT CTG AGA TAT GGA CTC CTG CTC CTG CTG AAG         945
Thr Thr Ser Thr Thr Leu Arg Tyr Gly Leu Leu Leu Leu Leu Lys
                    305                 310                 315

CAC CCA GAG GTC ACA GCT AAA GTC CAG GAA GAG ATT GAT CAT GTA         990
His Pro Glu Val Thr Ala Lys Val Gln Glu Glu Ile Asp His Val
                    320                 325                 330

ATT GGC AGA CAC AGG AGC CCC TGC ATG CAG GAT AGG AGC CAC ATG        1035
Ile Gly Arg His Arg Ser Pro Cys Met Gln Asp Arg Ser His Met
                    335                 340                 345

CCT TAC ACT GAT GCT GTA GTG CAC GAG ATC CAG AGA TAC AGT GAC        1080
Pro Tyr Thr Asp Ala Val Val His Glu Ile Gln Arg Tyr Ser Asp
                    350                 355                 360

CTT GTC CCC ACC GGT GTG CCC CAT GCA GTG ACC ACT GAT ACT AAG        1125
Leu Val Pro Thr Gly Val Pro His Ala Val Thr Thr Asp Thr Lys
                    365                 370                 375

TTC AGA AAC TAC CTC ATC CCC AAG GGC ACA ACC ATA ATG GCA TTA        1170
Phe Arg Asn Tyr Leu Ile Pro Lys Gly Thr Thr Ile Met Ala Leu
                    380                 385                 390

CTG ACT TCC GTG CTA CAT GAT GAC AGA GAA TTT CCT AAT CCA AAT        1215
Leu Thr Ser Val Leu His Asp Asp Arg Glu Phe Pro Asn Pro Asn
                    395                 400                 405

ATC TTT GAC CCT GGC CAC TTT CTA GAT AAG AAT GGC AAC TTT AAG        1260
Ile Phe Asp Pro Gly His Phe Leu Asp Lys Asn Gly Asn Phe Lys
                    410                 415                 420

AAA AGT GAC TAC TTC ATG CCT TTC TCA GCA GGA AAA CGA ATT TGT        1305
Lys Ser Asp Tyr Phe Met Pro Phe Ser Ala Gly Lys Arg Ile Cys
                    425                 430                 435

GCA GGA GAA GGA CTT GCC CGC ATG GAG CTA TTT TTA TTT CTA ACC        1350
Ala Gly Glu Gly Leu Ala Arg Met Glu Leu Phe Leu Phe Leu Thr
                    440                 445                 450

ACA ATT TTA CAG AAC TTT AAC CTG AAA TCT GTT GAT GAT TTA AAG        1395
Thr Ile Leu Gln Asn Phe Asn Leu Lys Ser Val Asp Asp Leu Lys
                    455                 460                 465

AAC CTC AAT ACT ACT GCA GTT ACC AAA GGG ATT GTT TCT CTG CCA        1440
Asn Leu Asn Thr Thr Ala Val Thr Lys Gly Ile Val Ser Leu Pro
                    470                 475                 480

CCC TCA TAC CAG ATC TGC TTC ATC CCT GTC TGA                        1473
Pro Ser Tyr Gln Ile Cys Phe Ile Pro Val ***
                    480                 490

(2) INFORMATION FOR SEQ ID NO: 13:

(i) SEQUENCE CHARACTERISTICS:
        (A) LENGTH: 1473
        (B) TYPE: nucleic acid
        (C) STRANDEDNESS: double
        (D) TOPOLOGY: linear (ii) SEQUENCE DESCRIPTION: SEQ ID NO: 13:

ATG GAA CCT TTT GTG GTC CTG GTG CTG TGT CTC TCT TTT ATG CTT          45
Met Glu Pro Phe Val Val Leu Val Leu Cys Leu Ser Phe Met Leu
 1                   5                  10                  15

CTC TTT TCA CTC TGG AGA CAG AGC TGT AGG AGA AGG AAG CTC CCT          90
Leu Phe Ser Leu Trp Arg Gln Ser Cys Arg Arg Arg Lys Leu Pro
                    20                  25                  30

CCT GGC CCC ACT CCT CTT CCT ATT ATT GGA AAT ATG CTA CAG ATA         135
Pro Gly Pro Thr Pro Leu Pro Ile Ile Gly Asn Met Leu Gln Ile
                    35                  40                  45

GAT GTT AAG GAC ATC TGC AAA TCT TTC ACC AAT TTC TCA AAA GTC         180
Asp Val Lys Asp Ile Cys Lys Ser Phe Thr Asn Phe Ser Lys Val
                    50                  55                  60
```

```
TAT GGT CCT GTG TTC ACC GTG TAT TTT GGC ATG AAT CCC ATA GTG              225
Tyr Gly Pro Val Phe Thr Val Tyr Phe Gly Met Asn Pro Ile Val
                65                  70                  75

GTG TTT CAT GGA TAT GTG GCA GTG AAG GAA GCC CTG ATT GAT AAT              270
Val Phe His Gly Tyr Val Ala Val Lys Glu Ala Leu Ile Asp Asn
                80                  85                  90

GGA GAG GAG TTT TCT GGA AGA GGC AAT TCC CCA ATA TCT CAA AGA              315
Gly Glu Glu Phe Ser Gly Arg Gly Asn Ser Pro Ile Ser Gln Arg
                95                 100                 105

ATT ACT AAA GGA CTT GGA ATC ATT TCC AGC AAT GGA AAG AGA TGG              360
Ile Thr Lys Gly Leu Gly Ile Ile Ser Ser Asn Gly Lys Arg Trp
               110                 115                 120

AAG GAG ATC CGG CGT TTC TCC CTC ACA ACC TTG CGG AAT TTT GGG              405
Lys Glu Ile Arg Arg Phe Ser Leu Thr Thr Leu Arg Asn Phe Gly
               125                 130                 135

ATG GGG AAG AAG AGC ATT GAG GAC CGT GTT CAA GAG GAA GCT CAC              450
Met Gly Lys Lys Ser Ile Glu Asp Arg Val Gln Glu Glu Ala His
               140                 145                 150

TGC CTT GTG GAG GAG TTG AGA AAA ACC AAG GCT TCA CCC TGT GAT              495
Cys Leu Val Glu Glu Leu Arg Lys Thr Lys Ala Ser Pro Cys Asp
               155                 160                 165

CCC ACT TTC ATC CTG GGC TGT GCT CCC TGC AAT GTG ATC TGC TCC              540
Pro Thr Phe Ile Leu Gly Cys Ala Pro Cys Asn Val Ile Cys Ser
               170                 175                 180

GTT GTT TTC CAG AAA CGA TTT GAT TAT AAA GAT CAG AAT TTT CTC              585
Val Val Phe Gln Lys Arg Phe Asp Tyr Lys Asp Gln Asn Phe Leu
               185                 190                 195

ACC CTG ATG AAA AGA TTC AAT GAA AAC TTC AGG ATT CTG AAC TCC              630
Thr Leu Met Lys Arg Phe Asn Glu Asn Phe Arg Ile Leu Asn Ser
               200                 205                 210

CCA TGG ATC CAG GTC TGC AAT AAT TTC CCT CTA CTC ATT GAT TGT              675
Pro Trp Ile Gln Val Cys Asn Asn Phe Pro Leu Leu Ile Asp Cys
               215                 220                 225

TTC CCA GGA ACT CAC AAC AAA GTG CTT AAA AAT GTT GCT CTT ACA              720
Phe Pro Gly Thr His Asn Lys Val Leu Lys Asn Val Ala Leu Thr
               230                 235                 240

CGA AGT TAC ATT AGG GAG AAA GTA AAA GAA CAC CAA GCA TCA CTG              765
Arg Ser Tyr Ile Arg Glu Lys Val Lys Glu His Gln Ala Ser Leu
               245                 250                 255

GAT GTT AAC AAT CCT CGG GAC TTT ATC GAT TGC TTC CTG ATC AAA              810
Asp Val Asn Asn Pro Arg Asp Phe Ile Asp Cys Phe Leu Ile Lys
               260                 265                 270

ATG GAG CAG GAA AAG GAC AAC CAA AAG TCA GAA TTC AAT ATT GAA              855
Met Glu Gln Glu Lys Asp Asn Gln Lys Ser Glu Phe Asn Ile Glu
               275                 280                 285

AAC TTG GTT GGC ACT GTA GCT GAT CTA TTT GTT GCT GGA ACA GAG              900
Asn Leu Val Gly Thr Val Ala Asp Leu Phe Val Ala Gly Thr Glu
               290                 295                 300

ACA ACA AGC ACC ACT CTG AGA TAT GGA CTC CTG CTC CTG CTG AAG              945
Thr Thr Ser Thr Thr Leu Arg Tyr Gly Leu Leu Leu Leu Leu Lys
               305                 310                 315

CAC CCA GAG GTC ACA GCT AAA GTC CAG GAA GAG ATT GAT CAT GTA              990
His Pro Glu Val Thr Ala Lys Val Gln Glu Glu Ile Asp His Val
               320                 325                 330

ATT GGC AGA CAC AGG AGC CCC TGC ATG CAG GAT AGG AGC CAC ATG             1035
Ile Gly Arg His Arg Ser Pro Cys Met Gln Asp Arg Ser His Met
               335                 340                 345

CCT TAC ACT GAT GCT GTA GTG CAC GAG ATC CAG AGA TAC AGT GAC             1080
Pro Tyr Thr Asp Ala Val Val His Glu Ile Gln Arg Tyr Ser Asp
```

```
              350             355             360
CTT GTC CCC ACC GGT GTG CCC CAT GCA GTG ACC ACT GAT ACT AAG           1125
Leu Val Pro Thr Gly Val Pro His Ala Val Thr Thr Asp Thr Lys
                365             370             375

TTC AGA AAC TAC CTC ATC CCC AAG GGC ACA ACC ATA ATG GCA TTA           1170
Phe Arg Asn Tyr Leu Ile Pro Lys Gly Thr Thr Ile Met Ala Leu
                380             385             390

CTG ACT TCC GTG CTA CAT GAT GAC AGA GAA TTT CCT AAT CCA AAT           1215
Leu Thr Ser Val Leu His Asp Asp Arg Glu Phe Pro Asn Pro Asn
                395             400             405

ATC TTT GAC CCT GGC CAC TTT CTA GAT AAG AAT GGC AAC TTT AAG           1260
Ile Phe Asp Pro Gly His Phe Leu Asp Lys Asn Gly Asn Phe Lys
                410             415             420

AAA AGT GAC TAC TTC ATG CCT TTC TCA GCA GGA AAA CGA ATT TGT           1305
Lys Ser Asp Tyr Phe Met Pro Phe Ser Ala Gly Lys Arg Ile Cys
                425             430             435

GCA GGA GAA GGA CTT GCC CGC ATG GAG CTA TTT TTA TTT CTA ACC           1350
Ala Gly Glu Gly Leu Ala Arg Met Glu Leu Phe Leu Phe Leu Thr
                440             445             450

ACA ATT TTA CAG AAC TTT AAC CTG AAA TCT GTT GAT GAT TTA AAG           1395
Thr Ile Leu Gln Asn Phe Asn Leu Lys Ser Val Asp Asp Leu Lys
                455             460             465

AAC CTC AAT ACT ACT GCA GTT ACC AAA GGG ATT GTT TCT CTG CCA           1440
Asn Leu Asn Thr Thr Ala Val Thr Lys Gly Ile Val Ser Leu Pro
                470             475             480

CCC TCA TAC CAG ATC TGC TTC ATC CCT GTC TGA                           1473
Pro Ser Tyr Gln Ile Cys Phe Ile Pro Val ***
                485             490

(2) INFORMATION FOR SEQ ID NO: 14:

(i) SEQUENCE CHARACTERISTICS:
        (A) LENGTH: 1473
        (B) TYPE:   nucleic acid
        (C) STRANDEDNESS: double
        (D) TOPOLOGY: linear (ii) SEQUENCE DESCRIPTION: SEQ ID NO: 14:

ATG GAT CCA GCT GTG GCT CTG GTG CTC TGT CTC TCC TGT TTG TTT            45
Met Asp Pro Ala Val Ala Leu Val Leu Cys Leu Ser Cys Leu Phe
 1               5              10              15

CTC CTT TCA CTC TGG AGG CAG AGC TCT GGA AGA GGG AGG CTC CCG            90
Leu Leu Ser Leu Trp Arg Gln Ser Ser Gly Arg Gly Arg Leu Pro
                20              25              30

TCT GGC CCC ACT CCT CTC CCG ATT ATT GGA AAT ATC CTG CAG TTA           135
Ser Gly Pro Thr Pro Leu Pro Ile Ile Gly Asn Ile Leu Gln Leu
                35              40              45

GAT GTT AAG GAC ATG AGC AAA TCC TTA ACC AAT TTC TCA AAA GTC           180
Asp Val Lys Asp Met Ser Lys Ser Leu Thr Asn Phe Ser Lys Val
                50              55              60

TAT GGC CCT GTG TTC ACT GTG TAT TTT GGC CTG AAG CCC ATT GTG           225
Tyr Gly Pro Val Phe Thr Val Tyr Phe Gly Leu Lys Pro Ile Val
                65              70              75

GTG TTG CAT GGA TAT GAA GCA GTG AAG GAG GCC CTG ATT GAT CAT           270
Val Leu His Gly Tyr Glu Ala Val Lys Glu Ala Leu Ile Asp His
                80              85              90

GGA GAG GAG TTT TCT GGA AGA GGA AGT TTT CCA GTG GCT GAA AAA           315
Gly Glu Glu Phe Ser Gly Arg Gly Ser Phe Pro Val Ala Glu Lys
                95             100             105

GTT AAC AAA GGA CTT GGA ATC CTT TTC AGC AAT GGA AAG AGA TGG           360
Val Asn Lys Gly Leu Gly Ile Leu Phe Ser Asn Gly Lys Arg Trp
```

-continued

```
                    110                 115                 120
AAG GAG ATC CGG CGT TTC TGC CTC ATG ACT CTG CGG AAT TTT GGG        405
Lys Glu Ile Arg Arg Phe Cys Leu Met Thr Leu Arg Asn Phe Gly
                125                 130                 135

ATG GGG AAG AGG AGC ATC GAG GAC CGT GTT CAA GAG GAA GCC CGC        450
Met Gly Lys Arg Ser Ile Glu Asp Arg Val Gln Glu Glu Ala Arg
                140                 145                 150

TGC CTT GTG GAG GAG TTG AGA AAA ACC AAT GCC TCA CCC TGT GAT        495
Cys Leu Val Glu Glu Leu Arg Lys Thr Asn Ala Ser Pro Cys Asp
                155                 160                 165

CCC ACT TTC ATC CTG GGC TGT GCT CCC TGC AAT GTG ATC TGC TCT        540
Pro Thr Phe Ile Leu Gly Cys Ala Pro Cys Asn Val Ile Cys Ser
                170                 175                 180

GTT ATT TTC CAT GAT CGA TTT GAT TAT AAA GAT CAG AGG TTT CTT        585
Val Ile Phe His Asp Arg Phe Asp Tyr Lys Asp Gln Arg Phe Leu
                185                 190                 195

AAC TTG ATG GAA AAA TTC AAT GAA AAC CTC AGG ATT CTG AGC TCT        630
Asn Leu Met Glu Lys Phe Asn Glu Asn Leu Arg Ile Leu Ser Ser
                200                 205                 210

CCA TGG ATC CAG GTC TGC AAT AAT TTC CCT GCT CTC ATC GAT TAT        675
Pro Trp Ile Gln Val Cys Asn Asn Phe Pro Ala Leu Ile Asp Tyr
                215                 220                 225

CTC CCA GGA AGT CAT AAT AAA ATA GCT GAA AAT TTT GCT TAC ATT        720
Leu Pro Gly Ser His Asn Lys Ile Ala Glu Asn Phe Ala Tyr Ile
                230                 235                 240

AAA AGT TAT GTA TTG GAG AGA ATA AAA GAA CAT CAA GAA TCC CTG        765
Lys Ser Tyr Val Leu Glu Arg Ile Lys Glu His Gln Glu Ser Leu
                245                 250                 255

GAC ATG AAC AGT GCT CGG GAC TTT ATT GAT TGT TTC CTG ATC AAA        810
Asp Met Asn Ser Ala Arg Asp Phe Ile Asp Cys Phe Leu Ile Lys
                260                 265                 270

ATG GAA CAG GAA AAG CAC AAT CAA CAG TCT GAA TTT ACT GTT GAA        855
Met Glu Gln Glu Lys His Asn Gln Gln Ser Glu Phe Thr Val Glu
                275                 280                 285

AGC TTG ATA GCC ACT GTA ACT GAT ATG TTT GGG GCT GGA ACA GAG        900
Ser Leu Ile Ala Thr Val Thr Asp Met Phe Gly Ala Gly Thr Glu
                290                 295                 300

ACA ACG AGC ACC ACT CTG AGA TAT GGA CTC CTG CTC CTG CTG AAG        945
Thr Thr Ser Thr Thr Leu Arg Tyr Gly Leu Leu Leu Leu Leu Lys
                305                 310                 315

TAC CCA GAG GTC ACA GCT AAA GTC CAG GAA GAG ATT GAA TGT GTA        990
Tyr Pro Glu Val Thr Ala Lys Val Gln Glu Glu Ile Glu Cys Val
                320                 325                 330

GTT GGC AGA AAC CGG AGC CCC TGT ATG CAG GAC AGG AGT CAC ATG       1035
Val Gly Arg Asn Arg Ser Pro Cys Met Gln Asp Arg Ser His Met
                335                 340                 345

CCC TAC ACA GAT GCT GTG GTG CAC GAG ATC CAG AGA TAC ATT GAC       1080
Pro Tyr Thr Asp Ala Val Val His Glu Ile Gln Arg Tyr Ile Asp
                350                 355                 360

CTC CTC CCC ACC AAC CTG CCC CAT GCA GTG ACC TGT GAT GTT AAA       1125
Leu Leu Pro Thr Asn Leu Pro His Ala Val Thr Cys Asp Val Lys
                365                 370                 375

TTC AAA AAC TAC CTC ATC CCC AAG GGC ACG ACC ATA ATA ACA TCC       1170
Phe Lys Asn Tyr Leu Ile Pro Lys Gly Thr Thr Ile Ile Thr Ser
                380                 385                 390

CTG ACT TCT GTG CTG CAC AAT GAC AAA GAA TTC CCC AAC CCA GAG       1215
Leu Thr Ser Val Leu His Asn Asp Lys Glu Phe Pro Asn Pro Glu
                395                 400                 405

ATG TTT GAC CCT GGC CAC TTT CTG GAT AAG AGT GGC AAC TTT AAG       1260
```

```
                    -continued

Met Phe Asp Pro Gly His Phe Leu Asp Lys Ser Gly Asn Phe Lys
            410                 415                 420

AAA AGT GAC TAC TTC ATG CCT TTC TCA GCA GGA AAA CGG ATG TGT         1305
Lys Ser Asp Tyr Phe Met Pro Phe Ser Ala Gly Lys Arg Met Cys
            425                 430                 435

ATG GGA GAG GGC CTG GCC CGC ATG GAG CTG TTT TTA TTC CTG ACC         1350
Met Gly Glu Gly Leu Ala Arg Met Glu Leu Phe Leu Phe Leu Thr
            440                 445                 450

ACC ATT TTG CAG AAC TTT AAC CTG AAA TCT CAG GTT GAC CCA AAG         1395
Thr Ile Leu Gln Asn Phe Asn Leu Lys Ser Gln Val Asp Pro Lys
            455                 460                 465

GAT ATT GAC ATC ACC CCC ATT GCC AAT GCA TTT GGT CGT GTG CCA         1440
Asp Ile Asp Ile Thr Pro Ile Ala Asn Ala Phe Gly Arg Val Pro
            470                 475                 480

CCC TTG TAC CAG CTC TGC TTC ATT CCT GTC TGA                         1473
Pro Leu Tyr Gln Leu Cys Phe Ile Pro Val ***
            485                 490

(2) INFORMATION FOR SEQ ID NO: 15:

(i) SEQUENCE CHARACTERISTICS:
          (A) LENGTH: 1473
          (B) TYPE: nucleic acid
          (C) STRANDEDNESS: double
          (D) TOPOLOGY: linear (ii) SEQUENCE DESCRIPTION: SEQ ID NO: 15:

ATG GAT CCT TTT GTG GTC CTT GTG CTC TGT CTC TCA TGT TTG CTT           45
Met Asp Pro Phe Val Val Leu Val Leu Cys Leu Ser Cys Leu Leu
  1               5                  10                  15

CTC CTT TCA CTC TGG AGA CAG AGC TCT GGG AGA GGA AAA CTC CCT           90
Leu Leu Ser Leu Trp Arg Gln Ser Ser Gly Arg Gly Lys Leu Pro
             20                  25                  30

CCT GGC CCC ACT CCT CTC CCA GTG ATT GGA AAT ATC CTA CAG ATA          135
Pro Gly Pro Thr Pro Leu Pro Val Ile Gly Asn Ile Leu Gln Ile
             35                  40                  45

GAT ATT AAG GAT GTC AGC AAA TCC TTA ACC AAT CTC TCA AAA ATC          180
Asp Ile Lys Asp Val Ser Lys Ser Leu Thr Asn Leu Ser Lys Ile
             50                  55                  60

TAT GGC CCT GTG TTC ACT CTG TAT TTT GGC CTC GAG CGC ATG GTG          225
Tyr Gly Pro Val Phe Thr Leu Tyr Phe Gly Leu Glu Arg Met Val
             65                  70                  75

GTG CTG CAT GGA TAT GAA GTG GTG AAG GAA GCC CTG ATT GAT CTT          270
Val Leu His Gly Tyr Glu Val Val Lys Glu Ala Leu Ile Asp Leu
             80                  85                  90

GGA GAG GAG TTT TCT GGA AGA GGC CAT TTC CCA CTG GCT GAA AGA          315
Gly Glu Glu Phe Ser Gly Arg Gly His Phe Pro Leu Ala Glu Arg
             95                 100                 105

GCT AAC AGA GGA TTT GGA ATC GTT TTC AGC AAT GGA AAG AGA TGG          360
Ala Asn Arg Gly Phe Gly Ile Val Phe Ser Asn Gly Lys Arg Trp
            110                 115                 120

AAG GAG ATC CGG CGT TTC TCC CTC ATG ACG CTG CGG AAT TTT GGG          405
Lys Glu Ile Arg Arg Phe Ser Leu Met Thr Leu Arg Asn Phe Gly
            125                 130                 135

ATG GGG AAG AGG AGC ATT GAG GAC CGT GTT CAA GAG GAA GCC CGC          450
Met Gly Lys Arg Ser Ile Glu Asp Arg Val Gln Glu Glu Ala Arg
            140                 145                 150

TGC CTT GTG GAG GAG TTG AGA AAA ACC AAG GCT TCA CCC TGT GAT          495
Cys Leu Val Glu Glu Leu Arg Lys Thr Lys Ala Ser Pro Cys Asp
            155                 160                 165

CCC ACT TTC ATC CTG GGC TGT GCT CCC TGC AAT GTG ATC TGC TCC          540
```

```
Pro Thr Phe Ile Leu Gly Cys Ala Pro Cys Asn Val Ile Cys Ser
            170                 175                 180

ATT ATT TTC CAG AAA CGT TTC GAT TAT AAA GAT CAG CAA TTT CTT        585
Ile Ile Phe Gln Lys Arg Phe Asp Tyr Lys Asp Gln Gln Phe Leu
            185                 190                 195

AAC TTG ATG GAA AAA TTG AAT GAA AAC ATC AGG ATT GTA AGC ACC        630
Asn Leu Met Glu Lys Leu Asn Glu Asn Ile Arg Ile Val Ser Thr
            200                 205                 210

CCC TGG ATC CAG ATA TGC AAT AAT TTT CCC ACT ATC ATT GAT TAT        675
Pro Trp Ile Gln Ile Cys Asn Asn Phe Pro Thr Ile Ile Asp Tyr
            215                 220                 225

TTC CCG GGA ACC CAT AAC AAA TTA CTT AAA AAC CTT GCT TTT ATG        720
Phe Pro Gly Thr His Asn Lys Leu Leu Lys Asn Leu Ala Phe Met
            230                 235                 240

GAA AGT GAT ATT TTG GAG AAA GTA AAA GAA CAC CAA GAA TCG ATG        765
Glu Ser Asp Ile Leu Glu Lys Val Lys Glu His Gln Glu Ser Met
            245                 250                 255

GAC ATC AAC AAC CCT CGG GAC TTT ATT GAT TGC TTC CTG ATC AAA        810
Asp Ile Asn Asn Pro Arg Asp Phe Ile Asp Cys Phe Leu Ile Lys
            260                 265                 270

ATG GAG AAG GAA AAG CAA AAC CAA CAG TCT GAA TTC ACT ATT GAA        855
Met Glu Lys Glu Lys Gln Asn Gln Gln Ser Glu Phe Thr Ile Glu
            275                 280                 285

AAC TTG GTA ATC ACT GCA GCT GAC TTA CTT GGA GCT GGG ACA GAG        900
Asn Leu Val Ile Thr Ala Ala Asp Leu Leu Gly Ala Gly Thr Glu
            290                 295                 300

ACA ACA AGC ACA ACC CTG AGA TAT GCT CTC CTT CTC CTG AAG            945
Thr Thr Ser Thr Thr Leu Arg Tyr Ala Leu Leu Leu Leu Lys
            305                 310                 315

CAC CCA GAG GTC ACA GCT AAA GTC CAG GAA GAG ATT GAA CGT GTC        990
His Pro Glu Val Thr Ala Lys Val Gln Glu Glu Ile Glu Arg Val
            320                 325                 330

GTT GGC AGA AAC CGG AGC CCC TGC ATG CAG GAC AGG GGC CAC ATG        1035
Val Gly Arg Asn Arg Ser Pro Cys Met Gln Asp Arg Gly His Met
            335                 340                 345

CCC TAC ACA GAT GCT GTG GTG CAC GAG GTC CAG AGA TAC ATC GAC        1080
Pro Tyr Thr Asp Ala Val Val His Glu Val Gln Arg Tyr Ile Asp
            350                 355                 360

CTC ATC CCC ACC AGC CTG CCC CAT GCA GTG ACC TGT GAC GTT AAA        1125
Leu Ile Pro Thr Ser Leu Pro His Ala Val Thr Cys Asp Val Lys
            365                 370                 375

TTC AGA AAC TAC CTC ATT CCC AAG GGC ACA ACC ATA TTA ACT TCC        1170
Phe Arg Asn Tyr Leu Ile Pro Lys Gly Thr Thr Ile Leu Thr Ser
            380                 385                 390

CTC ACT TCT GTG CTA CAT GAC AAC AAA GAA TTC CCC AAC CCA GAG        1215
Leu Thr Ser Val Leu His Asp Asn Lys Glu Phe Pro Asn Pro Glu
            395                 400                 405

ATG TTT GAC CCT CGT CAC TTT CTG GAT GAA GGT GGA AAT TTT AAG        1260
Met Phe Asp Pro Arg His Phe Leu Asp Glu Gly Gly Asn Phe Lys
            410                 415                 420

AAA AGT AAC TAC TTC ATG CCT TTC TCA GCA GGA AAA CGG ATT TGT        1305
Lys Ser Asn Tyr Phe Met Pro Phe Ser Ala Gly Lys Arg Ile Cys
            425                 430                 435

GTG GGA GAG GGC CTG GCC CGC ATG GAG CTG TTT TTA TTC CTG ACC        1350
Val Gly Glu Gly Leu Ala Arg Met Glu Leu Phe Leu Phe Leu Thr
            440                 445                 450

TTC ATT TTA CAG AAC TTT AAC CTG AAA TCT CTG ATT GAC CCA AAG        1395
Phe Ile Leu Gln Asn Phe Asn Leu Lys Ser Leu Ile Asp Pro Lys
            455                 460                 465
```

```
GAC CTT GAC ACA ACT CCT GTT GTC AAT GGA TTT GCT TCT GTC CCG        1440
Asp Leu Asp Thr Thr Pro Val Val Asn Gly Phe Ala Ser Val Pro
            470                 475                 480

CCC TTC TAT CAG CTG TGC TTC ATT CCT GTC TGA                        1473
Pro Phe Tyr Gln Leu Cys Phe Ile Pro Val ***
            485                 490
```

(2) INFORMATION FOR SEQ ID NO: 16:

(i) SEQUENCE CHARACTERISTICS:
        (A) LENGTH: 1494
        (B) TYPE: nucleic acid
        (C) STRANDEDNESS: double
        (D) TOPOLOGY: linear (ii) SEQUENCE DESCRIPTION: SEQ ID NO: 16:

```
ATG GGG CTA GAA GCA CTG GTG CCC CTG GCC GTG ATA GTG GCC ATC          45
Met Gly Leu Glu Ala Leu Val Pro Leu Ala Val Ile Val Ala Ile
 1               5                  10                  15

TTC CTG CTC CTG GTG GAC CTG ATG CAC CGG CGC CAA CGC TGG GCT          90
Phe Leu Leu Leu Val Asp Leu Met His Arg Arg Gln Arg Trp Ala
                20                  25                  30

GCA CGC TAC CCA CCA GGC CCC CTG CCA CTG CCC GGG CTG GGC AAC         135
Ala Arg Tyr Pro Pro Gly Pro Leu Pro Leu Pro Gly Leu Gly Asn
            35                  40                  45

CTG CTG CAT GTG GAC TTC CAG AAC ACA CCA TAC TGC TTC GAC CAG         180
Leu Leu His Val Asp Phe Gln Asn Thr Pro Tyr Cys Phe Asp Gln
            50                  55                  60

TTG CGG CGC CGC TTC GGG GAC GTG TTC AGC CTG CAG CTG GCC TGG         225
Leu Arg Arg Arg Phe Gly Asp Val Phe Ser Leu Gln Leu Ala Trp
            65                  70                  75

ACG CCG GTG GTC GTG CTC AAT GGG CTG GCG GCC GTG CGC GAG GCG         270
Thr Pro Val Val Val Leu Asn Gly Leu Ala Ala Val Arg Glu Ala
            80                  85                  90

CTG GTG ACC CAC GGC GAG GAC ACC GCC GAC CGC CCG CCT GTG CCC         315
Leu Val Thr His Gly Glu Asp Thr Ala Asp Arg Pro Pro Val Pro
            95                 100                 105

ATC ACC CAG ATC CTG GGT TTC GGG CCG CGT TCC CAA GGG GTG TTC         360
Ile Thr Gln Ile Leu Gly Phe Gly Pro Arg Ser Gln Gly Val Phe
           110                 115                 120

CTG GCG CGC TAT GGG CCC GCG TGG CGC GAG CAG AGG CGC TTC TCC         405
Leu Ala Arg Tyr Gly Pro Ala Trp Arg Glu Gln Arg Arg Phe Ser
           125                 130                 135

GTC TCC ACC TTG CGC AAC TTG GGC CTG GGC AAG AAG TCG CTG GAG         450
Val Ser Thr Leu Arg Asn Leu Gly Leu Gly Lys Lys Ser Leu Glu
           140                 145                 150

CAG TGG GTG ACC GAG GAG GCC GCC TGC CTT TGT GCC GCC TTC GCC         495
Gln Trp Val Thr Glu Glu Ala Ala Cys Leu Cys Ala Ala Phe Ala
           155                 160                 165

AAC CAC TCC GGA CGC CCC TTT CGC CCC AAC GGT CTC TTG GAC AAA         540
Asn His Ser Gly Arg Pro Phe Arg Pro Asn Gly Leu Leu Asp Lys
           170                 175                 180

GCC GTG AGC AAC GTG ATC GCC TCC CTC ACC TGC GGG CGC CGC TTC         585
Ala Val Ser Asn Val Ile Ala Ser Leu Thr Cys Gly Arg Arg Phe
           185                 190                 195

GAA TAC GAC GAC CCT CGC TTC CTC AGG CTG CTG GAC CTA GCT CAG         630
Glu Tyr Asp Asp Pro Arg Phe Leu Arg Leu Leu Asp Leu Ala Gln
           200                 205                 210

GAG GGA CTG AAG GAG GAG TCG GGC TTT CTG CGC GAG GTG CTG AAT         675
Glu Gly Leu Lys Glu Glu Ser Gly Phe Leu Arg Glu Val Leu Asn
           215                 220                 225
```

-continued

```
GCT GTC CCC GTC CTC CTG CAT ATC CCA GCG CTG GCT GGC AAG GTC          720
Ala Val Pro Val Leu Leu His Ile Pro Ala Leu Ala Gly Lys Val
            230                 235                 240

CTA CGC TTC CAA AAG GCT TTC CTG ACC CAG CTG GAT GAG CTG CTA          765
Leu Arg Phe Gln Lys Ala Phe Leu Thr Gln Leu Asp Glu Leu Leu
            245                 250                 255

ACT GAG CAC AGG ATG ACC TGG GAC CCA GCC CAG CCC CCC CGA GAC          810
Thr Glu His Arg Met Thr Trp Asp Pro Ala Gln Pro Pro Arg Asp
            260                 265                 270

CTG ACT GAG GCC TTC CTG GCA GAG ATG GAG AAG GCC AAG GGG AAC          855
Leu Thr Glu Ala Phe Leu Ala Glu Met Glu Lys Ala Lys Gly Asn
            275                 280                 285

CCT GAG AGC AGC TTC AAT GAT GAG AAC CTG TGC ATA GTG GTG GCT          900
Pro Glu Ser Ser Phe Asn Asp Glu Asn Leu Cys Ile Val Val Ala
            290                 295                 300

GAC CTG TTC TCT GCC GGG ATG GTG ACC ACC TCG ACC ACG CTG GCC          945
Asp Leu Phe Ser Ala Gly Met Val Thr Thr Ser Thr Thr Leu Ala
            305                 310                 315

TGG GGC CTC CTG CTC ATG ATC CTA CAT CCG GAT GTG CAG CGC CGT          990
Trp Gly Leu Leu Leu Met Ile Leu His Pro Asp Val Gln Arg Arg
            320                 325                 330

GTC CAA CAG GAG ATC GAC GAC GTG ATA GGG CAG GTG CGG CGA CCA         1035
Val Gln Gln Glu Ile Asp Asp Val Ile Gly Gln Val Arg Arg Pro
            335                 340                 345

GAG ATG GGT GAC CAG GCT CAC ATG CCC TAC ACC ACT GCC GTG ATT         1080
Glu Met Gly Asp Gln Ala His Met Pro Tyr Thr Thr Ala Val Ile
            350                 355                 360

CAT GAG GTG CAG CGC TTT GGG GAC ATC GTC CCC CTG GGT GTG ACC         1125
His Glu Val Gln Arg Phe Gly Asp Ile Val Pro Leu Gly Val Thr
            365                 370                 375

CAT ATG ACA TCC CGT GAC ATC GAA GTA CAG GGC TTC CGC ATC CCT         1170
His Met Thr Ser Arg Asp Ile Glu Val Gln Gly Phe Arg Ile Pro
            380                 385                 390

AAG GGA ACG ACA CTC ATC ACC AAC CTG TCA TCG GTG CTG AAG GAT         1215
Lys Gly Thr Thr Leu Ile Thr Asn Leu Ser Ser Val Leu Lys Asp
            395                 400                 405

GAG GCC GTC TGG GAG AAG CCC TTC CGC TTC CAC CCC GAA CAC TTC         1260
Glu Ala Val Trp Glu Lys Pro Phe Arg Phe His Pro Glu His Phe
            410                 415                 420

CTG GAT GCC CAG GGC CAC TTT GTG AAG CCG GAG GCC TTC CTG CCT         1305
Leu Asp Ala Gln Gly His Phe Val Lys Pro Glu Ala Phe Leu Pro
            425                 430                 435

TTC TCA GCA GGC CGC CGT GCA TGC CTC GGG GAG CCC CTG GCC CGC         1350
Phe Ser Ala Gly Arg Arg Ala Cys Leu Gly Glu Pro Leu Ala Arg
            440                 445                 450

ATG GAG CTC TTC CTC TTC TTC ACC TCC CTG CTG CAG CAC TTC AGC         1395
Met Glu Leu Phe Leu Phe Phe Thr Ser Leu Leu Gln His Phe Ser
            455                 460                 465

TTC TCG GTG CCC ACT GGA CAG CCC CGG CCC AGC CAC CAT GGT GTC         1440
Phe Ser Val Pro Thr Gly Gln Pro Arg Pro Ser His His Gly Val
            470                 475                 480

TTT GCT TTC CTG GTG ACC CCA TCC CCC TAT GAG CTT TGT GCT GTG         1485
Phe Ala Phe Leu Val Thr Pro Ser Pro Tyr Glu Leu Cys Ala Val
            485                 490                 495

CCC CGC TAG                                                         1494
Pro Arg ***
```

(2) INFORMATION FOR SEQ ID NO: 17:

(i) SEQUENCE CHARACTERISTICS:

(A) LENGTH: 1494
(B) TYPE: nucleic acid
(C) STRANDEDNESS: double
(D) TOPOLOGY: linear (ii) SEQUENCE DESCRIPTION: SEQ ID NO: 17:

| | | | | | | | | | | | | | | | |
|---|---|---|---|---|---|---|---|---|---|---|---|---|---|---|---|
| ATG | GGG | CTA | GAA | GCA | CTG | GTG | CCC | CTG | GCC | GTG | ATA | GTG | GCC | ATC | 45 |
| Met | Gly | Leu | Glu | Ala | Leu | Val | Pro | Leu | Ala | Val | Ile | Val | Ala | Ile | |
| 1 | | | | 5 | | | | | 10 | | | | | 15 | |

| | | | | | | | | | | | | | | | |
|---|---|---|---|---|---|---|---|---|---|---|---|---|---|---|---|
| TTC | CTG | CTC | CTG | GTG | GAC | CTG | ATG | CAC | CGG | CGC | CAA | CGC | TGG | GCT | 90 |
| Phe | Leu | Leu | Leu | Val | Asp | Leu | Met | His | Arg | Arg | Gln | Arg | Trp | Ala | |
| | | | | 20 | | | | | 25 | | | | | 30 | |

| | | | | | | | | | | | | | | | |
|---|---|---|---|---|---|---|---|---|---|---|---|---|---|---|---|
| GCA | CGC | TAC | CCA | CCA | GGC | CCC | CTG | CCA | CTG | CCC | GGG | CTG | GGC | AAC | 135 |
| Ala | Arg | Tyr | Pro | Pro | Gly | Pro | Leu | Pro | Leu | Pro | Gly | Leu | Gly | Asn | |
| | | | | 35 | | | | | 40 | | | | | 45 | |

| | | | | | | | | | | | | | | | |
|---|---|---|---|---|---|---|---|---|---|---|---|---|---|---|---|
| CTG | CTG | CAT | GTG | GAC | TTC | CAG | AAC | ACA | CCA | TAC | TGC | TTC | GAC | CAG | 180 |
| Leu | Leu | His | Val | Asp | Phe | Gln | Asn | Thr | Pro | Tyr | Cys | Phe | Asp | Gln | |
| | | | | 50 | | | | | 55 | | | | | 60 | |

| | | | | | | | | | | | | | | | |
|---|---|---|---|---|---|---|---|---|---|---|---|---|---|---|---|
| TTG | CGG | CGC | CGC | TTC | GGG | GAC | GTG | TTC | AGC | CTG | CAG | CTG | GCC | TGG | 225 |
| Leu | Arg | Arg | Arg | Phe | Gly | Asp | Val | Phe | Ser | Leu | Gln | Leu | Ala | Trp | |
| | | | | 65 | | | | | 70 | | | | | 75 | |

| | | | | | | | | | | | | | | | |
|---|---|---|---|---|---|---|---|---|---|---|---|---|---|---|---|
| ACG | CCG | GTG | GTC | GTG | CTC | AAT | GGG | CTG | GCG | GCC | GTG | CGC | GAG | GCG | 270 |
| Thr | Pro | Val | Val | Val | Leu | Asn | Gly | Leu | Ala | Ala | Val | Arg | Glu | Ala | |
| | | | | 80 | | | | | 85 | | | | | 90 | |

| | | | | | | | | | | | | | | | |
|---|---|---|---|---|---|---|---|---|---|---|---|---|---|---|---|
| CTG | GTG | ACC | CAC | GGC | GAG | GAC | ACC | GCC | GAC | CGC | CCG | CCT | GTG | CCC | 315 |
| Leu | Val | Thr | His | Gly | Glu | Asp | Thr | Ala | Asp | Arg | Pro | Pro | Val | Pro | |
| | | | | 95 | | | | | 100 | | | | | 105 | |

| | | | | | | | | | | | | | | | |
|---|---|---|---|---|---|---|---|---|---|---|---|---|---|---|---|
| ATC | ACC | CAG | ATC | CTG | GGT | TTC | GGG | CCG | CGT | TCC | CAA | GGG | GTG | TTC | 360 |
| Ile | Thr | Gln | Ile | Leu | Gly | Phe | Gly | Pro | Arg | Ser | Gln | Gly | Val | Phe | |
| | | | | 110 | | | | | 115 | | | | | 120 | |

| | | | | | | | | | | | | | | | |
|---|---|---|---|---|---|---|---|---|---|---|---|---|---|---|---|
| CTG | GCG | CGC | TAT | GGG | CCC | GCG | TGG | CGC | GAG | CAG | AGG | CGC | TTC | TCC | 405 |
| Leu | Ala | Arg | Tyr | Gly | Pro | Ala | Trp | Arg | Glu | Gln | Arg | Arg | Phe | Ser | |
| | | | | 125 | | | | | 130 | | | | | 135 | |

| | | | | | | | | | | | | | | | |
|---|---|---|---|---|---|---|---|---|---|---|---|---|---|---|---|
| GTC | TCC | ACC | TTG | CGC | AAC | TTG | GGC | CTG | GGC | AAG | AAG | TCG | CTG | GAG | 450 |
| Val | Ser | Thr | Leu | Arg | Asn | Leu | Gly | Leu | Gly | Lys | Lys | Ser | Leu | Glu | |
| | | | | 140 | | | | | 145 | | | | | 150 | |

| | | | | | | | | | | | | | | | |
|---|---|---|---|---|---|---|---|---|---|---|---|---|---|---|---|
| CAG | TGG | GTG | ACC | GAG | GAG | GCC | GCC | TGC | CTT | TGT | GCC | GCC | TTC | GCC | 495 |
| Gln | Trp | Val | Thr | Glu | Glu | Ala | Ala | Cys | Leu | Cys | Ala | Ala | Phe | Ala | |
| | | | | 155 | | | | | 160 | | | | | 165 | |

| | | | | | | | | | | | | | | | |
|---|---|---|---|---|---|---|---|---|---|---|---|---|---|---|---|
| AAC | CAC | TCC | GGA | CGC | CCC | TTT | CGC | CCC | AAC | GGT | CTC | TTG | GAC | AAA | 540 |
| Asn | His | Ser | Gly | Arg | Pro | Phe | Arg | Pro | Asn | Gly | Leu | Leu | Asp | Lys | |
| | | | | 170 | | | | | 175 | | | | | 180 | |

| | | | | | | | | | | | | | | | |
|---|---|---|---|---|---|---|---|---|---|---|---|---|---|---|---|
| GCC | GTG | AGC | AAC | GTG | ATC | GCC | TCC | CTC | ACC | TGC | GGG | CGC | CGC | TTC | 585 |
| Ala | Val | Ser | Asn | Val | Ile | Ala | Ser | Leu | Thr | Cys | Gly | Arg | Arg | Phe | |
| | | | | 185 | | | | | 190 | | | | | 195 | |

| | | | | | | | | | | | | | | | |
|---|---|---|---|---|---|---|---|---|---|---|---|---|---|---|---|
| GAA | TAC | GAC | GAC | CCT | CGC | TTC | CTC | AGG | CTG | CTG | GAC | CTA | GCT | CAG | 630 |
| Glu | Tyr | Asp | Asp | Pro | Arg | Phe | Leu | Arg | Leu | Leu | Asp | Leu | Ala | Gln | |
| | | | | 200 | | | | | 205 | | | | | 210 | |

| | | | | | | | | | | | | | | | |
|---|---|---|---|---|---|---|---|---|---|---|---|---|---|---|---|
| GAG | GGA | CTG | AAG | GAG | GAG | TCG | GGC | TTT | CTG | CGC | GAG | GTG | CTG | AAT | 675 |
| Glu | Gly | Leu | Lys | Glu | Glu | Ser | Gly | Phe | Leu | Arg | Glu | Val | Leu | Asn | |
| | | | | 215 | | | | | 220 | | | | | 225 | |

| | | | | | | | | | | | | | | | |
|---|---|---|---|---|---|---|---|---|---|---|---|---|---|---|---|
| GCT | GTC | CCC | GTC | CTC | CTG | CAT | ATC | CCA | GCG | CTG | GCT | GGC | AAG | GTC | 720 |
| Ala | Val | Pro | Val | Leu | Leu | His | Ile | Pro | Ala | Leu | Ala | Gly | Lys | Val | |
| | | | | 230 | | | | | 235 | | | | | 240 | |

| | | | | | | | | | | | | | | | |
|---|---|---|---|---|---|---|---|---|---|---|---|---|---|---|---|
| CTA | CGC | TTC | CAA | AAG | GCT | TTC | CTG | ACC | CAG | CTG | GAT | GAG | CTG | CTA | 765 |
| Leu | Arg | Phe | Gln | Lys | Ala | Phe | Leu | Thr | Gln | Leu | Asp | Glu | Leu | Leu | |
| | | | | 245 | | | | | 250 | | | | | 255 | |

| | | | | | | | | | | | | | | | |
|---|---|---|---|---|---|---|---|---|---|---|---|---|---|---|---|
| ACT | GAG | CAC | AGG | ATG | ACC | TGG | GAC | CCA | GCC | CAG | CCC | CCC | CGA | GAC | 810 |
| Thr | Glu | His | Arg | Met | Thr | Trp | Asp | Pro | Ala | Gln | Pro | Pro | Arg | Asp | |
| | | | | 260 | | | | | 265 | | | | | 270 | |

```
CTG ACT GAG GCC TTC CTG GCA GAG ATG GAG AAG GCC AAG GGG AAC        855
Leu Thr Glu Ala Phe Leu Ala Glu Met Glu Lys Ala Lys Gly Asn
            275                 280                 285

CCT GAG AGC AGC TTC AAT GAT GAG AAC CTG CGC ATA GTG GTG GCT        900
Pro Glu Ser Ser Phe Asn Asp Glu Asn Leu Arg Ile Val Val Ala
            290                 295                 300

GAC CTG TTC TCT GCC GGG ATG GTG ACC TCG ACC ACG CTG GCC            945
Asp Leu Phe Ser Ala Gly Met Val Thr Ser Thr Thr Leu Ala
            305                 310                 315

TGG GGC CTC CTG CTC ATG ATC CTA CAT CCG GAT GTG CAG CGC CGT        990
Trp Gly Leu Leu Leu Met Ile Leu His Pro Asp Val Gln Arg Arg
            320                 325                 330

GTC CAA CAG GAG ATC GAC GAC GTG ATA GGG CAG GTG CGG CGA CCA       1035
Val Gln Gln Glu Ile Asp Asp Val Ile Gly Gln Val Arg Arg Pro
            335                 340                 345

GAG ATG GGT GAC CAG GCT CAC ATG CCC TAC ACC ACT GCC GTG ATT       1080
Glu Met Gly Asp Gln Ala His Met Pro Tyr Thr Thr Ala Val Ile
            350                 355                 360

CAT GAG GTG CAG CGC TTT GGG GAC ATC GTC CCC CTG GGT GTG ACC       1125
His Glu Val Gln Arg Phe Gly Asp Ile Val Pro Leu Gly Val Thr
            365                 370                 375

CAT ATG ACA TCC CGT GAC ATC GAA GTA CAG GGC TTC CGC ATC CCT       1170
His Met Thr Ser Arg Asp Ile Glu Val Gln Gly Phe Arg Ile Pro
            380                 385                 390

AAG GGA ACG ACA CTC ATC ACC AAC CTG TCA TCG GTG CTG AAG GAT       1215
Lys Gly Thr Thr Leu Ile Thr Asn Leu Ser Ser Val Leu Lys Asp
            395                 400                 405

GAG GCC GTC TGG GAG AAG CCC TTC CGC TTC CAC CCC GAA CAC TTC       1260
Glu Ala Val Trp Glu Lys Pro Phe Arg Phe His Pro Glu His Phe
            410                 415                 420

CTG GAT GCC CAG GGC CAC TTT GTG AAG CCG GAG GCC TTC CTG CCT       1305
Leu Asp Ala Gln Gly His Phe Val Lys Pro Glu Ala Phe Leu Pro
            425                 430                 435

TTC TCA GCA GGC CGC CGT GCA TGC CTC GGG GAG CCC CTG GCC CGC       1350
Phe Ser Ala Gly Arg Arg Ala Cys Leu Gly Glu Pro Leu Ala Arg
            440                 445                 450

ATG GAG CTC TTC CTC TTC TTC ACC TCC CTG CTG CAG CAC TTC AGC       1395
Met Glu Leu Phe Leu Phe Phe Thr Ser Leu Leu Gln His Phe Ser
            455                 460                 465

TTC TCG GTG CCC ACT GGA CAG CCC CGG CCC AGC CAC CAT GGT GTC       1440
Phe Ser Val Pro Thr Gly Gln Pro Arg Pro Ser His His Gly Val
            470                 475                 480

TTT GCT TTC CTG GTG ACC CCA TCC CCC TAT GAG CTT TGT GCT GTG       1485
Phe Ala Phe Leu Val Thr Pro Ser Pro Tyr Glu Leu Cys Ala Val
            485                 490                 495

CCC CGC TAG                                                       1494
Pro Arg ***

(2) INFORMATION FOR SEQ ID NO: 18:

(i) SEQUENCE CHARACTERISTICS:
        (A) LENGTH: 1494
        (B) TYPE: nucleic acid
        (C) STRANDEDNESS: double
        (D) TOPOLOGY: linear (ii) SEQUENCE DESCRIPTION: SEQ ID NO: 18:

ATG GGG CTA GAA GCA CTG GTG CCC CTG GCC GTG ATA GTG GCC ATC         45
Met Gly Leu Glu Ala Leu Val Pro Leu Ala Val Ile Val Ala Ile
 1               5                  10                  15

TTC CTG CTC CTG GTG GAC CTG ATG CAC CGG CGC CAA CGC TGG GCT         90
```

-continued

```
                Phe Leu Leu Leu Val Asp Leu Met His Arg Arg Gln Arg Trp Ala
                             20                  25                  30

GCA CGC TAC CCA CCA GGC CCC CTG CCA CTG CCC GGG CTG GGC AAC         135
Ala Arg Tyr Pro Pro Gly Pro Leu Pro Leu Pro Gly Leu Gly Asn
             35                  40                  45

CTG CTG CAT GTG GAC TTC CAG AAC ACA CCA TAC TGC TTC GAC CAG         180
Leu Leu His Val Asp Phe Gln Asn Thr Pro Tyr Cys Phe Asp Gln
             50                  55                  60

TTG CGG CGC CGC TTC GGG GAC GTG TTC AGC CTG CAG CTG GCC TGG         225
Leu Arg Arg Arg Phe Gly Asp Val Phe Ser Leu Gln Leu Ala Trp
             65                  70                  75

ACG CCG GTG GTC GTG CTC AAT GGG CTG GCG GCC GTG CGC GAG GCG         270
Thr Pro Val Val Val Leu Asn Gly Leu Ala Ala Val Arg Glu Ala
             80                  85                  90

CTG GTG ACC CAC GGC GAG GAC ACC GCC GAC CGC CCG CCT GTG CCC         315
Leu Val Thr His Gly Glu Asp Thr Ala Asp Arg Pro Pro Val Pro
             95                 100                 105

ATC ACC CAG ATC CTG GGT TTC GGG CCG CGT TCC CAA GGG GTG TTC         360
Ile Thr Gln Ile Leu Gly Phe Gly Pro Arg Ser Gln Gly Val Phe
            110                 115                 120

CTG GCG CGC TAT GGG CCC GCG TGG CGC GAG CAG AGG CGC TTC TCC         405
Leu Ala Arg Tyr Gly Pro Ala Trp Arg Glu Gln Arg Arg Phe Ser
            125                 130                 135

GTC TCC ACC TTG CGC AAC TTG GGC CTG GGC AAG AAG TCG CTG GAG         450
Val Ser Thr Leu Arg Asn Leu Gly Leu Gly Lys Lys Ser Leu Glu
            140                 145                 150

CAG TGG GTG ACC GAG GAG GCC GCC TGC CTT TGT GCC GCC TTC GCC         495
Gln Trp Val Thr Glu Glu Ala Ala Cys Leu Cys Ala Ala Phe Ala
            155                 160                 165

AAC CAC TCC GGA CGC CCC TTT CGC CCC AAC GGT CTC TTG GAC AAA         540
Asn His Ser Gly Arg Pro Phe Arg Pro Asn Gly Leu Leu Asp Lys
            170                 175                 180

GCC GTG AGC AAC GTG ATC GCC TCC CTC ACC TGC GGG CGC CGC TTC         585
Ala Val Ser Asn Val Ile Ala Ser Leu Thr Cys Gly Arg Arg Phe
            185                 190                 195

GAA TAC GAC GAC CCT CGC TTC CTC AGG CTG CTG GAC CTA GCT CAG         630
Glu Tyr Asp Asp Pro Arg Phe Leu Arg Leu Leu Asp Leu Ala Gln
            200                 205                 210

GAG GGA CTG AAG GAG GAG TCG GGC TTT CTG CGC GAG GTG CTG AAT         675
Glu Gly Leu Lys Glu Glu Ser Gly Phe Leu Arg Glu Val Leu Asn
            215                 220                 225

GCT GTC CCC GTC CTC CTG CAT ATC CCA GCG CTG GCT GGC AAG GTC         720
Ala Val Pro Val Leu Leu His Ile Pro Ala Leu Ala Gly Lys Val
            230                 235                 240

CTA CGC TTC CAA AAG GCT TTC CTG ACC CAG CTG GAT GAG CTG CTA         765
Leu Arg Phe Gln Lys Ala Phe Leu Thr Gln Leu Asp Glu Leu Leu
            245                 250                 255

ACT GAG CAC AGG ATG ACC TGG GAC CCA GCC CAG CCC CCC CGA GAC         810
Thr Glu His Arg Met Thr Trp Asp Pro Ala Gln Pro Pro Arg Asp
            260                 265                 270

CTG ACT GAG GCC TTC CTG GCA GAG ATG GAG AAG GCC AAG GGG AAC         855
Leu Thr Glu Ala Phe Leu Ala Glu Met Glu Lys Ala Lys Gly Asn
            275                 280                 285

CCT GAG AGC AGC TTC AAT GAT GAG AAC CTG CGC ATA GTG GTG GCT         900
Pro Glu Ser Ser Phe Asn Asp Glu Asn Leu Arg Ile Val Val Ala
            290                 295                 300

GAC CTG TTC TCT GCC GGG ATG GTG ACC ACC TCG ACC ACG CTG GCC         945
Asp Leu Phe Ser Ala Gly Met Val Thr Thr Ser Thr Thr Leu Ala
            305                 310                 315
```

```
TGG GGC CTC CTG CTC ATG ATC CTA CAT CCG GAT GTG CAG CGC CGT        990
Trp Gly Leu Leu Leu Met Ile Leu His Pro Asp Val Gln Arg Arg
            320                 325                 330

GTC CAA CAG GAG ATC GAC GAC GTG ATA GGG CAG GTG CGG CGA CCA       1035
Val Gln Gln Glu Ile Asp Asp Val Ile Gly Gln Val Arg Arg Pro
            335                 340                 345

GAG ATG GGT GAC CAG GCT CAC ATG CCC TAC ACC ACT GCC GTG ATT       1080
Glu Met Gly Asp Gln Ala His Met Pro Tyr Thr Thr Ala Val Ile
            350                 355                 360

CAT GAG GTG CAG CGC TTT GGG GAC ATC GTC CCC CTG GGT GTG ACC       1125
His Glu Val Gln Arg Phe Gly Asp Ile Val Pro Leu Gly Val Thr
            365                 370                 375

CAT ATG ACA TCC CGT GAC ATC GAA GTA CAG GGC TTC CGC ATC CCT       1170
His Met Thr Ser Arg Asp Ile Glu Val Gln Gly Phe Arg Ile Pro
            380                 385                 390

AAG GGA ACG ACA CTC ATC ACC AAC CTG TCA TCG GTG CTG AAG GAT       1215
Lys Gly Thr Thr Leu Ile Thr Asn Leu Ser Ser Val Leu Lys Asp
            395                 400                 405

GAG GCC GTC TGG GAG AAG CCC TTC CGC TTC CAC CCC GAA CAC TTC       1260
Glu Ala Val Trp Glu Lys Pro Phe Arg Phe His Pro Glu His Phe
            410                 415                 420

CTG GAT GCC CAG GGC CAC TTT GTG AAG CCG GAG GCC TTC CTG CCT       1305
Leu Asp Ala Gln Gly His Phe Val Lys Pro Glu Ala Phe Leu Pro
            425                 430                 435

TTC TCA GCA GGC CGC CGT GCA TGC CTC GGG GAG CCC CTG GCC CGC       1350
Phe Ser Ala Gly Arg Arg Ala Cys Leu Gly Glu Pro Leu Ala Arg
            440                 445                 450

ATG GAG CTC TTC CTC TTC TTC ACC TCC CTG CTG CAG CAC TTC AGC       1395
Met Glu Leu Phe Leu Phe Phe Thr Ser Leu Leu Gln His Phe Ser
            455                 460                 465

TTC TCG GTG CCC ACT GGA CAG CCC CGG CCC AGC CAC CAT GGT GTC       1440
Phe Ser Val Pro Thr Gly Gln Pro Arg Pro Ser His His Gly Val
            470                 475                 480

TTT GCT TTC CTG GTG AGC CCA TCC CCC TAT GAG CTT TGT GCT GTG       1485
Phe Ala Phe Leu Val Ser Pro Ser Pro Tyr Glu Leu Cys Ala Val
            485                 490                 495

CCC CGC TAG                                                       1494
Pro Arg ***

(2) INFORMATION FOR SEQ ID NO: 19:

(i) SEQUENCE CHARACTERISTICS:
        (A) LENGTH:  1494
        (B) TYPE:  nucleic acid
        (C) STRANDEDNESS:  double
        (D) TOPOLOGY:  linear (ii) SEQUENCE DESCRIPTION: SEQ ID NO: 19:

ATG GGG CTA GAA GCA CTG GTG CCC CTG GCC GTG ATA GTG GCC ATC         45
Met Gly Leu Glu Ala Leu Val Pro Leu Ala Val Ile Val Ala Ile
  1               5                  10                  15

TTC CTG CTC CTG GTG GAC CTG ATG CAC CGG CGC CAA CGC TGG GCT         90
Phe Leu Leu Leu Val Asp Leu Met His Arg Arg Gln Arg Trp Ala
            20                  25                  30

GCA CGC TAC CCA CCA GGC CCC CTG CCA CTG CCC GGG CTG GGC AAC        135
Ala Arg Tyr Pro Pro Gly Pro Leu Pro Leu Pro Gly Leu Gly Asn
            35                  40                  45

CTG CTG CAT GTG GAC TTC CAG AAC ACA CCA TAC TGC TTC GAC CAG        180
Leu Leu His Val Asp Phe Gln Asn Thr Pro Tyr Cys Phe Asp Gln
            50                  55                  60

TTG CGG CGC CGC TTC GGG GAC GTG TTC AGC CTG CAG CTG GCC TGG        225
```

```
Leu Arg Arg Arg Phe Gly Asp Val Phe Ser Leu Gln Leu Ala Trp
             65                  70                  75

ACG CCG GTG GTC GTG CTC AAT GGG CTG GCG GCC GTG CGC GAG GCG         270
Thr Pro Val Val Val Leu Asn Gly Leu Ala Ala Val Arg Glu Ala
             80                  85                  90

CTG GTG ACC CAC GGC GAG GAC ACC GCC GAC CGC CCG CCT GTG CCC         315
Leu Val Thr His Gly Glu Asp Thr Ala Asp Arg Pro Pro Val Pro
             95                 100                 105

ATC ACC CAG ATC CTG GGT TTC GGG CCG CGT TCC CAA GGG GTG TTC         360
Ile Thr Gln Ile Leu Gly Phe Gly Pro Arg Ser Gln Gly Val Phe
            110                 115                 120

CTG GCG CGC TAT GGG CCC GCG TGG CGC GAG CAG AGG CGC TTC TCC         405
Leu Ala Arg Tyr Gly Pro Ala Trp Arg Glu Gln Arg Arg Phe Ser
            125                 130                 135

GTC TCC ACC TTG CGC AAC TTG GGC CTG GGC AAG AAG TCG CTG GAG         450
Val Ser Thr Leu Arg Asn Leu Gly Leu Gly Lys Lys Ser Leu Glu
            140                 145                 150

CAG TGG GTG ACC GAG GAG GCC GCC TGC CTT TGT GCC GCC TTC GCC         495
Gln Trp Val Thr Glu Glu Ala Ala Cys Leu Cys Ala Ala Phe Ala
            155                 160                 165

AAC CAC TCC GGA CGC CCC TTT CGC CCC AAC GGT CTC TTG GAC AAA         540
Asn His Ser Gly Arg Pro Phe Arg Pro Asn Gly Leu Leu Asp Lys
            170                 175                 180

GCC GTG AGC AAC GTG ATC GCC TCC CTC ACC TGC GGG CGC CGC TTC         585
Ala Val Ser Asn Val Ile Ala Ser Leu Thr Cys Gly Arg Arg Phe
            185                 190                 195

GAA TAC GAC GAC CCT CGC TTC CTC AGG CTG CTG GAC CTA GCT CAG         630
Glu Tyr Asp Asp Pro Arg Phe Leu Arg Leu Leu Asp Leu Ala Gln
            200                 205                 210

GAG GGA CTG AAG GAG GAG TCG GGC TTT CTG CGC GAG GTG CTG AAT         675
Glu Gly Leu Lys Glu Glu Ser Gly Phe Leu Arg Glu Val Leu Asn
            215                 220                 225

GCT GTC CCC GTC CTC CTG CAT ATC CCA GCG CTG GCT GGC AAG GTC         720
Ala Val Pro Val Leu Leu His Ile Pro Ala Leu Ala Gly Lys Val
            230                 235                 240

CTA CGC TTC CAA AAG GCT TTC CTG ACC CAG CTG GAT GAG CTG CTA         765
Leu Arg Phe Gln Lys Ala Phe Leu Thr Gln Leu Asp Glu Leu Leu
            245                 250                 255

ACT GAG CAC AGG ATG ACC TGG GAC CCA GCC CAG CCC CCC CGA GAC         810
Thr Glu His Arg Met Thr Trp Asp Pro Ala Gln Pro Pro Arg Asp
            260                 265                 270

CTG ACT GAG GCC TTC CTG GCA GAG ATG GAG AAG GCC AAG GGG AAC         855
Leu Thr Glu Ala Phe Leu Ala Glu Met Glu Lys Ala Lys Gly Asn
            275                 280                 285

CCT GAG AGC AGC TTC AAT GAT GAG AAC CTG TGC ATA GTG GTG GCT         900
Pro Glu Ser Ser Phe Asn Asp Glu Asn Leu Cys Ile Val Val Ala
            290                 295                 300

GAC CTG TTC TCT GCC GGG ATG GTG ACC ACC TCG ACC ACG CTG GCC         945
Asp Leu Phe Ser Ala Gly Met Val Thr Thr Ser Thr Thr Leu Ala
            305                 310                 315

TGG GGC CTC CTG CTC ATG ATC CTA CAT CCG GAT GTG CAG CGC CGT         990
Trp Gly Leu Leu Leu Met Ile Leu His Pro Asp Val Gln Arg Arg
            320                 325                 330

GTC CAA CAG GAG ATC GAC GAC GTG ATA GGG CAG GTG CGG CGA CCA        1035
Val Gln Gln Glu Ile Asp Asp Val Ile Gly Gln Val Arg Arg Pro
            335                 340                 345

GAG ATG GGT GAC CAG GCT CAC ATG CCC TAC ACC ACT GCC GTG ATT        1080
Glu Met Gly Asp Gln Ala His Met Pro Tyr Thr Thr Ala Val Ile
            350                 355                 360
```

```
CAT GAG GTG CAG CGC TTT GGG GAC ATC GTC CCC CTG GGT GTG ACC        1125
His Glu Val Gln Arg Phe Gly Asp Ile Val Pro Leu Gly Val Thr
                365                 370                 375

CAT ATG ACA TCC CGT GAC ATC GAA GTA CAG GGC TTC CGC ATC CCT        1170
His Met Thr Ser Arg Asp Ile Glu Val Gln Gly Phe Arg Ile Pro
                380                 385                 390

AAG GGA ACG ACA CTC ATC ACC AAC CTG TCA TCG GTG CTG AAG GAT        1215
Lys Gly Thr Thr Leu Ile Thr Asn Leu Ser Ser Val Leu Lys Asp
                395                 400                 405

GAG GCC GTC TGG GAG AAG CCC TTC CGC TTC CAC CCC GAA CAC TTC        1260
Glu Ala Val Trp Glu Lys Pro Phe Arg Phe His Pro Glu His Phe
                410                 415                 420

CTG GAT GCC CAG GGC CAC TTT GTG AAG CCG GAG GCC TTC CTG CCT        1305
Leu Asp Ala Gln Gly His Phe Val Lys Pro Glu Ala Phe Leu Pro
                425                 430                 435

TTC TCA GCA GGC CGC CGT GCA TGC CTC GGG GAG CCC CTG GCC CGC        1350
Phe Ser Ala Gly Arg Arg Ala Cys Leu Gly Glu Pro Leu Ala Arg
                440                 445                 450

ATG GAG CTC TTC CTC TTC TTC ACC TCC CTG CTG CAG CAC TTC AGC        1395
Met Glu Leu Phe Leu Phe Phe Thr Ser Leu Leu Gln His Phe Ser
                455                 460                 465

TTC TCG GTG CCC ACT GGA CAG CCC CGG CCC AGC CAC CAT GGT GTC        1440
Phe Ser Val Pro Thr Gly Gln Pro Arg Pro Ser His His Gly Val
                470                 475                 480

TTT GCT TTC CTG GTG AGC CCA TCC CCC TAT GAG CTT TGT GCT GTG        1485
Phe Ala Phe Leu Val Ser Pro Ser Pro Tyr Glu Leu Cys Ala Val
                485                 490                 495

CCC CGC TAG                                                        1494
Pro Arg ***

(2) INFORMATION FOR SEQ ID NO: 20:

(i) SEQUENCE CHARACTERISTICS:
        (A) LENGTH: 34
        (B) TYPE: nucleic acid
        (C) STRANDEDNESS: single
        (D) TOPOLOGY: linear (ii) SEQUENCE DESCRIPTION: SEQ ID NO: 20:

GGAACGCATG GTGGTGCTGC ATGGATATGA AGTG                                34

(2) INFORMATION FOR SEQ ID NO: 21:

(i) SEQUENCE CHARACTERISTICS:
        (A) LENGTH: 56
        (B) TYPE: nucleic acid
        (C) STRANDEDNESS: single
        (D) TOPOLOGY: linear (ii) SEQUENCE DESCRIPTION: SEQ ID NO: 21:

CTCAAAGATC TATGGCCCTG TGTTCACTCT GTATTTTGGC CTCGAGCGCA TGGTGG        56

(2) INFORMATION FOR SEQ ID NO: 22:

(i) SEQUENCE CHARACTERISTICS:
        (A) LENGTH: 28
        (B) TYPE: nucleic acid
        (C) STRANDEDNESS: single
        (D) TOPOLOGY: linear (ii) SEQUENCE DESCRIPTION: SEQ ID NO: 22:

CCACCATGCG CTCGAGGCCA AAATACAG                                       28
```

(2) INFORMATION FOR SEQ ID NO: 23:

(i) SEQUENCE CHARACTERISTICS:
        (A) LENGTH: 31
        (B) TYPE: nucleic acid
        (C) STRANDEDNESS: single
        (D) TOPOLOGY: linear (ii) SEQUENCE DESCRIPTION: SEQ ID NO: 23:

GGGTTCCCGG GAAATAATCA ATGATAGTGG G                           31

(2) INFORMATION FOR SEQ ID NO: 24:

(i) SEQUENCE CHARACTERISTICS:
        (A) LENGTH: 32
        (B) TYPE: nucleic acid
        (C) STRANDEDNESS: single
        (D) TOPOLOGY: linear (ii) SEQUENCE DESCRIPTION: SEQ ID NO: 24:

GGATTGTAAG CACCCCCTGG ATCCAGATAT GC                         32

(2) INFORMATION FOR SEQ ID NO: 25:

(i) SEQUENCE CHARACTERISTICS:
        (A) LENGTH: 34
        (B) TYPE: nucleic acid
        (C) STRANDEDNESS: single
        (D) TOPOLOGY: linear (ii) SEQUENCE DESCRIPTION: SEQ ID NO: 25:

CCCAGCTCCA AGTAAGTCAG CTGCAGTGAT TACC                       34

(2) INFORMATION FOR SEQ ID NO: 26:

(i) SEQUENCE CHARACTERISTICS:
        (A) LENGTH: 42
        (B) TYPE: nucleic acid
        (C) STRANDEDNESS: single
        (D) TOPOLOGY: linear (ii) SEQUENCE DESCRIPTION: SEQ ID NO: 26:

GGTGGTACCC TTGGGAATGA GGTAGTTTCT GAATTTAACG TC               42

(2) INFORMATION FOR SEQ ID NO: 27:

(i) SEQUENCE CHARACTERISTICS:
        (A) LENGTH: 33
        (B) TYPE: nucleic acid
        (C) STRANDEDNESS: single
        (D) TOPOLOGY: linear (ii) SEQUENCE DESCRIPTION: SEQ ID NO: 27:

AGTCTAGAAT GGATCCTTTT GTGGTCCTTG TGC                        33

(2) INFORMATION FOR SEQ ID NO: 28:

(i) SEQUENCE CHARACTERISTICS:
        (A) LENGTH: 30
        (B) TYPE: nucleic acid
        (C) STRANDEDNESS: single
        (D) TOPOLOGY: linear (ii) SEQUENCE DESCRIPTION: SEQ ID NO: 28:

CCCAGAGCTC TGTCTCCAGA GTGAAAGGAG                            30

(2) INFORMATION FOR SEQ ID NO: 29:

(i) SEQUENCE CHARACTERISTICS:
    (A) LENGTH: 30
    (B) TYPE: nucleic acid
    (C) STRANDEDNESS: single
    (D) TOPOLOGY: linear (ii) SEQUENCE DESCRIPTION: SEQ ID NO: 29:

```
ACAGAGCTCT GGGAGAGGAA AACTCCCTCC                              30
```

(2) INFORMATION FOR SEQ ID NO: 30:

(i) SEQUENCE CHARACTERISTICS:
        (A) LENGTH: 54
        (B) TYPE: nucleic acid
        (C) STRANDEDNESS: single
        (D) TOPOLOGY: linear (ii) SEQUENCE DESCRIPTION: SEQ ID NO: 30:

```
CCATAGATTT TTGAGAGATT GGTTAAGGAT TTGCTGACAT CCTTAATATC TATC   54
```

(2) INFORMATION FOR SEQ ID NO: 31:

(i) SEQUENCE CHARACTERISTICS:
        (A) LENGTH: 30
        (B) TYPE: nucleic acid
        (C) STRANDEDNESS: single
        (D) TOPOLOGY: linear (ii) SEQUENCE DESCRIPTION: SEQ ID NO: 31:

```
GACCCTCGTC ACTTTCTGGA TGAAGGTGGA                              30
```

(2) INFORMATION FOR SEQ ID NO: 32:

(i) SEQUENCE CHARACTERISTICS:
        (A) LENGTH: 36
        (B) TYPE: nucleic acid
        (C) STRANDEDNESS: single
        (D) TOPOLOGY: linear (ii) SEQUENCE DESCRIPTION: SEQ ID NO: 32:

```
GAAGTAGTTA CTTTTCTTAA AATTTCCACC TTCATC                       36
```

(2) INFORMATION FOR SEQ ID NO: 33:

(i) SEQUENCE CHARACTERISTICS:
        (A) LENGTH: 37
        (B) TYPE: nucleic acid
        (C) STRANDEDNESS: single
        (D) TOPOLOGY: linear (ii) SEQUENCE DESCRIPTION: SEQ ID NO: 33:

```
AAAGAATTCC CCAACCCAGA GATGTTTGAC CCTCGTC                      37
```

(2) INFORMATION FOR SEQ ID NO: 34:

(i) SEQUENCE CHARACTERISTICS:
        (A) LENGTH: 59
        (B) TYPE: nucleic acid
        (C) STRANDEDNESS: single
        (D) TOPOLOGY: linear (ii) SEQUENCE DESCRIPTION: SEQ ID NO: 34:

```
GGCCAGGCCC TCTCCCACAC AAATCCGTTT TCCTGCTGAG AAAGGCATGA        50
AGTAGTTAC                                                     59
```

(2) INFORMATION FOR SEQ ID NO: 35:

(i) SEQUENCE CHARACTERISTICS:
        (A) LENGTH: 44
        (B) TYPE: nucleic acid
        (C) STRANDEDNESS: single
        (D) TOPOLOGY: linear (ii) SEQUENCE DESCRIPTION: SEQ ID NO: 35:

GAGAGGGCCT GGCCCGCATG GAGCTGTTTT TATTCCTGAC CTTC         44

(2) INFORMATION FOR SEQ ID NO: 36:

(i) SEQUENCE CHARACTERISTICS:
        (A) LENGTH: 34
        (B) TYPE: nucleic acid
        (C) STRANDEDNESS: single
        (D) TOPOLOGY: linear (ii) SEQUENCE DESCRIPTION: SEQ ID NO: 36:

CAGGAGTTGT GTCAAGGTCC TTTGGGTCAA TCAG         34

(2) INFORMATION FOR SEQ ID NO: 37:

(i) SEQUENCE CHARACTERISTICS:
        (A) LENGTH: 64
        (B) TYPE: nucleic acid
        (C) STRANDEDNESS: single
        (D) TOPOLOGY: linear (ii) SEQUENCE DESCRIPTION: SEQ ID NO: 37:

TTGTCAATGG ATTTGCTTCT GTCCCGCCCT TCTATCAGCT GTGCTTCATT         50

CCTGTCTGAG GATC         64

(2) INFORMATION FOR SEQ ID NO: 38:

(i) SEQUENCE CHARACTERISTICS:
        (A) LENGTH: 55
        (B) TYPE: nucleic acid
        (C) STRANDEDNESS: single
        (D) TOPOLOGY: linear (ii) SEQUENCE DESCRIPTION: SEQ ID NO: 38:

CAGAAGCAAA TCCATTGACA ACAGGAGTTG TGTCAAGGTC CTTTGGGTCA ATCAG         55

(2) INFORMATION FOR SEQ ID NO: 39:

(i) SEQUENCE CHARACTERISTICS:
        (A) LENGTH: 60
        (B) TYPE: nucleic acid
        (C) STRANDEDNESS: single
        (D) TOPOLOGY: linear (ii) SEQUENCE DESCRIPTION: SEQ ID NO: 39:

CTCAGACAGG AATGAAGCAC AGCTGATAGA AGGGCGGGAC AGAAGCAAAT         50

CCATTGACAA         60

(2) INFORMATION FOR SEQ ID NO: 40:

(i) SEQUENCE CHARACTERISTICS:
        (A) LENGTH: 32
        (B) TYPE: nucleic acid
        (C) STRANDEDNESS: single
        (D) TOPOLOGY: linear (ii) SEQUENCE DESCRIPTION: SEQ ID NO: 40:

```
GCAGCCAGAC CATCTGTGCT TCTTCAGACA GG                                32

(2) INFORMATION FOR SEQ ID NO: 41:

(i) SEQUENCE CHARACTERISTICS:
        (A) LENGTH: 44
        (B) TYPE: nucleic acid
        (C) STRANDEDNESS: single
        (D) TOPOLOGY: linear (ii) SEQUENCE DESCRIPTION: SEQ ID NO: 41:

CACCATATTA ACTTCCCTCA CTTCTGTGCT ACATGACAAC AAAG                   44

(2) INFORMATION FOR SEQ ID NO: 42:

(i) SEQUENCE CHARACTERISTICS:
        (A) LENGTH: 52
        (B) TYPE: nucleic acid
        (C) STRANDEDNESS: single
        (D) TOPOLOGY: linear (ii) SEQUENCE DESCRIPTION: SEQ ID NO: 42:

AATTCTTTGT TGTCATGTAG CACAGAAGTG AGGGAAGTTA ATATGGTGGT AC           52
```

METHOD FOR SAFETY EVALUATION OF CHEMICAL COMPOUND USING RECOMBINANT YEAST EXPRESSING HUMAN CYTOCHROME P450

FIELD OF THE INVENTION

The present invention relates to a method for evaluation of the safety of a chemical compound using recombinant yeasts expressing human cytochrome P450.

BACKGROUND OF THE INVENTION

The cytochrome P450 is an enzyme catalyzing the monooxygenation of a substance in the human liver.

It is known that recombinant human cells expressing heterogeneous human cytochrome P450 species have been used for determination of metabolisms and toxicities of chemical substances. However, this method is unsatisfactory as a method of evaluation of the safety of chemical compounds partly because the kinds of the human cytochrome P450 species expressed by the cells and the levels of the expression are so limited that the amount of metabolite obtained is not enough for determination of the metabolism and toxicity, and partly because it requires not only a high density culture technique but a high cultivation cost. Accordingly, there has been a great demand for developing an advantageous method.

SUMMARY OF THE INVENTION

As a result of the extensive study, the present inventors have found that yeasts are particularly suitable as hosts for production of human cytochrome P450 and yeast NADPH-P450 reductase to be used in vitro determination of metabolisms and toxicities of chemical substances because yeasts grow so rapidly and can stably express both the human cytochrome P450 and yeast NADPH-P450 reductase at high expression levels to provide sufficient amounts of the metabolites in a short period of time, thereby enabling a precise and quick analysis of the metabolites.

Moreover, they have also found that, despite that there are a considerable number of human cytochrome P450 molecular species, the human metabolic system for chemical compounds can be reproduced in vitro when at least four human cytochrome P450 molecular species, i.e., human cytochrome P450 1A2, P450 2C9, P450 2E1 and P450 3A4, are combined.

Thus, the present invention provides a method for evaluation of the safety of a chemical compound, which comprises the steps of:

(a) reacting a chemical compound with recombinant yeast cells expressing, or in other words producing, human cytochrome P450 molecular species P450 1A2, P450 2C9, P450 2E1 and P450 3A4 together with a yeast NADPH-P450 reductase, which may be in the form of a fused enzyme with each of said human cytochrome P450 molecular species, or with the cell free extracts of the yeast cells; and (b) analyzing the resulting metabolite to determine the safety of the compound.

The present invention further provides a method for determination of the human metabolite of a chemical compound, which comprises the steps of:

(a) reacting a chemical compound with recombinant yeast cells producing human cytochrome P450 molecular species P450 1A2, P450 2C9, P450 2E1 and P450 3A4 together with a yeast NADPH-P450 reductase, which may be in the form of a fused enzyme with each of said human cytochrome P450 molecular species, or with cell free extracts of the yeast cells; and (b) identifying the resulting metabolite.

BRIEF DESCRIPTION OF THE DRAWINGS

FIGS. 1 to 4 show various primers for cloning human P450 genes.

FIG. 5 shows a synthetic linker for human P450 gene cloning.

DETAILED DESCRIPTION OF THE INVENTION

Figure 6:
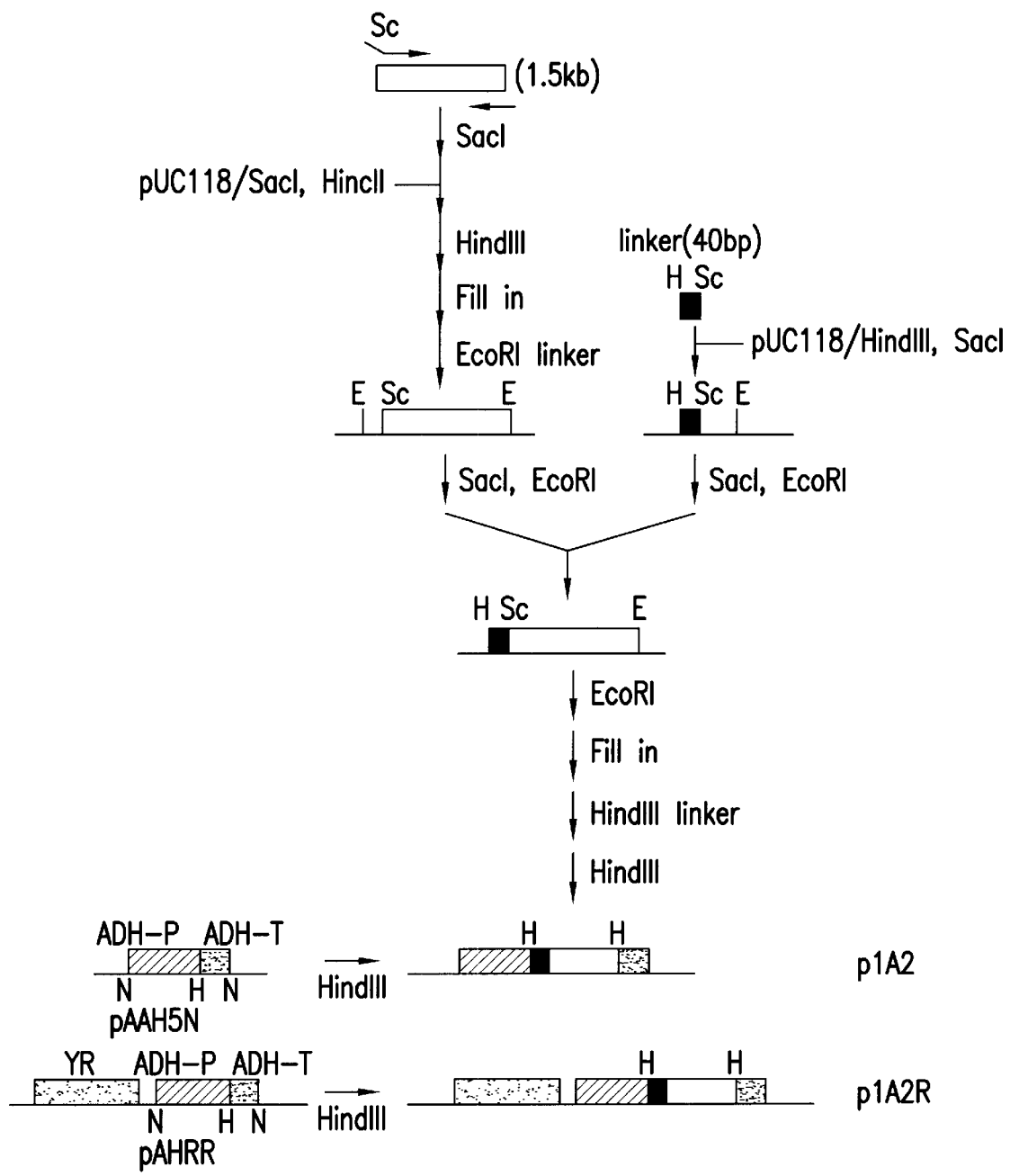
FIG. 6 shows a method of constructing yeast expression plasmids for human P450 1A2.

According to the present invention, it can be determined whether a test compound will be converted into a carcinogenic or mutagenic form through the metabolism in the human liver, and whether the test compound or its metabolite has mutagenicity.

Thus, the present invention provides a method for evaluation of safety of a chemical compound, and a method for determination of the human metabolite of a chemical compound.

Human Cytochrome P450 and Their Genes

The yeasts capable of expressing, or producing, said enzymes can be obtained by transforming them with expression plasmids containing genes encoding said enzymes with a conventional recombinant DNA method.

The human P450 molecular species to be used in the present invention include at least four human cytochrome P450 molecular species, i.e., human cytochrome P450 1A2, P450 2C9, P450 2E1 and P450 3A4. The genes encoding these essential human cytochrome P450 molecular species and yeast NADPH-P450 reductase are reported in Nucleic Acids Res., 14, 6773–6774, 1986; J. Biochem., 102, 1075–1082, 1987; J. Biol. Chem., 261, 16689–16697, 1986; DNA, 7, 79–86, 1988; and J. Biochem., 103, 1004–1010, 1988.

Although the kinds of P450 molecular species present in human liver vary among the race and individuals, the combination of said human P450 molecular species includes at least about 85% (molar ratio) of the total amount of the human P450 molecular species present in the human liver. Hence, the present method using the said combination of human P450 molecular species can accurately reproduce the human liver metabolism in vitro.

The combination of these P450 molecular species may optionally be varied, taking into account of the amounts of these P450 molecular species in the liver: the amount of P450 3A4 present in the human liver is about 35±10% of the total amount of the human P450 molecular species; P450 2C9 about 25±10%; P450 1A2 about 23±10%; and P450 2E1 about 17±10%.

In addition to the above-mentioned combination, human P450 molecular species P450 2A6, P450 2C19 and/or P450 2D6 (Biochemistry, 29, 1322–1329, 1990; Biochemistry, 30, 3247–3255, 1991; Am. J. Hum. Genet., 45, 889–904, 1989) may also be added. In this case, the combined human P450 molecular species covers at least 90% of the total amount of the human P450 molecular species present in the human liver.

The in vitro human metabolic system that reproduces accurately the human metabolism of a chemical compound, and can represent the differences among races and individuals can be obtained when these human P450 molecular species are properly combined, taking into account of the amounts of these species in the liver.

Furthermore, at least one human cytochrome P450 molecular species selected from the group of P450 1A1, P450 2B6, P450 2C8 and P450 2C18 (Science, 228, 80–83, 1985; Biochemistry, 28, 7340–7348, 1989; Nucleic Acids Res., 15, 10053–10054, 1987; Biochemistry, 30, 3247–3255, 1991) may be added to said human cytochrome P450 molecular species to reproduce in vitro the metabolism of the human liver more accurately.

The nucleotide sequences coding for the human P450 molecular species are disclosed in SEQ ID NOs: 1 to 19.

Cloning of Genes

The genes coding for the human cytochrome P450 molecular species are known and can be obtained by the conventional cloning methods.

For example, they may be obtained by:

(i) preparing a mRNA fraction containing the mRNA of the gene coding for human cytochrome P450 molecular species;

(ii) preparing a cDNA from the mRNA fraction using reverse transcriptase;

(iii) preparing a cDNA library by inserting said cDNA into a pharge vector or a plasmid vector; and (iv) cloning the gene coding for the human cytochrome P450 molecular species from the cDNA library obtained above or from a commercially available human liver-derived cDNA library using a DNA fragment having an identical sequence to some part of the desired gene or an antibody reactive to the protein produced by the gene.

The gene may also be obtained from the above-described cDNA library by the PCR method.

The gene coding for yeast NADPH-P450 reductase may be obtained by the same method as used for cloning of the genes coding for human P450 molecular species. More specifically, the gene may be obtained by such a known method as described in the Japanese Patent Laid-open Publication No. 62-19085.

Construction of Yeast Expression Plasmids

The yeasts capable of expressing said enzymes can be obtained by transforming them with expression plasmids containing genes encoding said enzymes with a conventional recombinant DNA method.

The yeast expression plasmid having a gene coding for human P450 molecular species and a gene coding for the yeast NADPH-P450 reductase can be constructed by using a conventional recombinant DNA method.

As to the promoter to be used for construction of the expression plasmids for the yeast of the present invention, there is no particular restriction so long as the promoter can be used in usual expression systems for yeasts, and a promoter of a yeast alcohol dehydrogenase gene (hereinafter referred to as ADH promoter), glyceraldehyde-3-phosphate dehydrogenase promoter (hereinafter referred to as GAPDH promoter), and phosphoglycerate kinase (hereinafter referred to as PGK promoter) are preferably used in the present invention.

The ADH promoter can be prepared by a usual genetic engineering method, for example, from a yeast expression vector pAAH5 possessing a yeast ADH1 promoter and terminator ("Methods in Enzymology" by Ammerer et al., vol.101, pp.192–201). The yeast ADH1 promoter is described in the U.S. Pat. No. 299,733 to Washington Research Foundation and it requires patent license from the patentee in a case of using the same for an industrial or commercial purpose.

The yeast expression plasmid having both a gene coding for human P450 molecular species and a gene coding for the yeast NADPH-P450 reductase can be constructed by, for example, inserting an NotI fragment prepared from yeast expression vector pAAH5N possessing the ADH promoter and terminator (Japanese Patent Laid-open Publication No. 2-211880) to an NotI site of plasmid pARRN possessing a gene coding for yeast NADPH-P450 reductase (Japanese Patent Laid-open Publication No. 2-211880) and then inserting cDNA coding for the human P450 molecular species to the HindIII site of the thus obtained plasmid pAHRR. Moreover, a vector obtained by exchanging a Hind III site of pAAH5N with other restriction enzyme site may be used for the same purpose.

In the present invention a gene coding for an artificial fused enzyme comprising human cytochrome P450 molecular species and yeast NADPH-P450 reductase can also be used. The artificial fused enzyme can catalyze mono-oxygenation reaction and the efficiency of the electron transfer from NADPH is so improved that the activity of the mono-oxygenation reaction is much enhanced. Accordingly, a great amount of metabolic products can be obtained in a shorter period of time, enabling accurate analysis.

The fused gene comprises a gene coding for the human cytochrome P450 molecule on the 5'-terminal and a gene coding for the yeast NADPH-P450 reductase on 3'-terminal.

The gene coding for such an artificial fused enzyme can be constructed by ligating a gene coding for a human cytochrome P450 species and a gene coding for yeast NADPH-P450 reductase by a conventional recombinant DNA method, and the constructed gene is usually inserted to the Hind III site of the yeast expression vector pAAH5N having ADH promoter and ADH terminator described in the Japanese Patent Laid-open Publication No. 2-211880.

Transformation of Yeast

The yeast cells expressing the human P450 molecular species and yeast NADPH-P450 reductase or yeast cells expressing an artificial fused enzyme comprising human P450 molecular species and NADPH-P450 reductase can be obtained by introducing the thus constructed yeast expression plasmid into a yeast by a known method such as a protoplast method or a method using alkaline metal salt (LiCl).

In the present invention, two or more expression plasmids may optionally be introduced into a single strain of yeast so that the yeast can express two or more molecular species simultaneously.

As the hosts, Saccharomyces cerevisiae is used in the method of the present invention, in particular, *Saccharomyces cerevisiae* AH22 (ATCC 38626) is preferably used.

Reaction of Test Compound

In the method of the present invention, a test compound is reacted with a mixture of at least said four human P450 molecular species, or separately with each of the said four human P450 molecular species in the presence of the yeast NADPH-P450 reductase.

Alternatively, it may be first reacted with one or more of the essential human P450 molecular species, and then with a mixture of, or separately with the rest of them; each of the reactions is carried out in the presence of the yeast NADPH-P450 reductase.

The reaction is carried out by reacting a test compound with the yeast obtained by the transformation with an expression plasmid containing a gene encoding a human P450 molecular species and a gene encoding yeast NADPH-P450 reductase, or a fused gene encoding a fused enzyme of a human P450 molecular species and a yeast NADPH-P450 reductase, or with the cell free extracts of the yeast cells.

In the reaction of a test compound with the enzymes of the present invention, living yeast cells and their cell free extracts are usually used.

As the cell free extracts, subcellular fraction of cells containing microsomal fractions, or fractions containing both microsome and cytoplasm is used. The cell free extracts or fractions can be prepared, for example, by a known method (DNA, Vol.4, No.3, pp.203–210 (1985)).

However, the present invention can be preferably carried out with the cell free extracts, especially with microsomal fractions of the cells. But, when biological analytic method is used to determination of the mutagenicity or carcinogenicity, fractions containing microsome and cytoplasm are preferably used.

The reaction can be conducted by adding a test compound to a culture solution or a buffer solution of yeast cells or cell free extracts, and the resultant solution is usually incubated at a temperature, for example, at about 10° C. to 40° C., for about 0.1 to 48 hours.

The amounts of the yeast cells or cell free extracts and the compound vary depending on the conditions such as reaction temperature, reaction time and the kind of the test compound to be used.

For instance, the amount of the yeast cells to be used in the solution is preferably from about $10^5$ to about $10^{10}$ per 1 ml of the solution, preferably, from about $10^7$ to about $10^8$ per 1 ml of the solution. When cell free extracts are used, from about $10^{10}$ to about $10^{15}$ of P450 molecules per 1 ml of the solution, preferably from about $10^{12}$ to about $10^{13}$ of P450 molecules per 1 ml of the solution is usually used.

The amount of the compound to be added is preferably within a range of from about 0.01 $\mu$mol to about 1 $\mu$mol per 1 ml of the solution.

The above ranges may be optionally varied, if necessary.

Determination of Metabolites

The metabolites present in the reaction solution can then be subjected to elucidation of the chemical structures and the measurement of their amounts. The analysis of the chemical structure can be conducted by known methods ("Guide to Apparatus Analysis (2)", edited by Jiro Shiokawa et al., (revised edition) first print, issued from Kagaku Dojin (1985); "Spectral Identification for Organic Compound" by R. M. Silverstein, fourth edition, third print, issued from Tokyo Kagaku Dojin (1984)).

From the results of the analysis of the metabolites, it can be determined whether the tested compound will be detoxicated or metabolized into a carcinogen in the human liver when administered.

Determination of Toxic Effects of Metabolites

The toxic effects, in particular mutagenicity, of the resulting metabolites can be determined by a conventional biological analytic method such as the Ames Test. For example, the metabolites present in the reaction solution are allowed to react with mutant bacteria such as histidine requiring Salmonella strain (*Salmonella typhimurium* (his−)), or tryptophan requiring *Escherichia coil* (*Escherichia coil* (trp−)), and then determine whether the metabolites cause the back mutation of the bacteria whether the colonies of revertant which is not requiring the amino acid (His+ or Trp+) are formed, and, if formed, how many colonies. In place of the bacteria, mammalian cells such as MCL-5 cells, which are sensitive to cell toxicity of a chemical compound (U.S. Pat. No. 4,532,204), can be used.

In this method, the compounds that cause the back mutation will be judged to be mutagenicity test-positive.

It is also possible to simultaneously proceed the step (a) of reacting the test compound with the yeast cells or the cell free extracts, and the step (b) of analyzing the metabolites present in the reaction solution.

The mutagenicity of arylamine derivatives, which are known to be metabolized by the liver into a mutagens, can be examined by the biological analytic method. For example, the mutagenicity of 2-aminoanthrathene can be detected at the concentration of about 0.1 $\mu$g of 2-aminoanthrathene when 20 pmol of P450 1A2, which is active specifically to 2-aminoanthrathene, is used (Table 1).

In the present invention, a metabolic probe for a human P450 molecular species can be obtained.

If a certain chemical compound is converted by a particular human P450 molecular species into a specific metabolite, the amount of such a human P450 molecular species can be determined by detecting such a metabolite in excretions such as blood or urine of a living body who has been administered the compound, and such a compound is called a metabolic probe.

In the present invention, such a metabolic probe can be obtained by screening the metabolites obtained by reacting chemical compounds with the yeasts of the present invention.

EXAMPLES

The present invention will be further illustrated by the following examples, which are not to be construed to limit the scope thereof.

Preparation of cDNA Coding for Human P450 Molecular Species cDNA coding for human P450 molecular species were obtained from commercially available human liver cDNA library (Clontech Co.) by the PCR method using primers for cloning human P450 genes as shown in FIGS. 1 to 4, and a method using a synthetic linker for human P450 gene cloning as shown in FIG. 5. Thus obtained nucleotide sequences for the cDNA and the deduced amino acid sequences are shown in the sequence listing.

Relationship between SEQ ID NOs and human P450 molecular species are as follows:

1. The essential human cytochrome P450 molecular species for the present invention.

| (1) SEQ ID NO: 1 | 1A2 |
| (2) SEQ ID NO: 2 | 2C9 |
| (3) SEQ ID NO: 3 | 2E1 |
| (4) SEQ ID NO: 4 | 3A4 |

2. Auxiliary Human cytochrome P450 molecular species

| (1) SEQ ID NOs: 5, 6 and 7 | 1A1 |
| (2) SEQ ID NOs: 8 and 9 | 2A6 |
| (3) SEQ ID NO: 10 | 2B6 |
| (4) SEQ ID NOs: 11, 12 and 13 | 2C8 |
| (5) SEQ ID NO: 14 | 2C18 |
| (6) SEQ ID NO: 15 | 2C19 |
| (7) SEQ ID NOs: 16, 17, 18 and 19 | 2D6 |

Construction of Yeast Expression Plasmids: p1A2 and p1A2R

FIG. 6 shows a method of constructing yeast expression plasmids for human P450 1A2. The protein coding region of P450 1A2 gene of about 1.5 kb excluding about 40 bp at the 5'-terminal was amplified by the PCR method using the primers shown in FIG. 1. The resultant fragment of about 1.5 kb was cleaved with SacI and sub-cloned to a pUC118 vector. About 40 bp at the 5'-terminal was chemically synthesized as the linkers shown in FIG. 5 and sub-cloned between the HindIII and SacI sites of the pUC118 vector. The plasmid having the 1.5 kb fragment was digested by HindIII, blunted, and then ligated with an EcoRI linker. The EcoRI-SacI fragment was prepared from the resulting plasmid and ligated into the plasmid containing the 5'-terminal 40 bp. Then, it was treated with EcoRI and blunted. A HindIII linker was inserted into the blunted fragment. The obtained fragment then cleaved with HindIII was inserted into pAAH5N and PAHRR to construct a yeast expression plasmid p1A2 for human P450 1A2, and a yeast expression plasmid p1A2R for simultaneous expression of human P450 1A2 and yeast NADPH-P450 reductase.

Construction of Yeast Expression Plasmids: p2C9 and P2C9R

Figure 7:
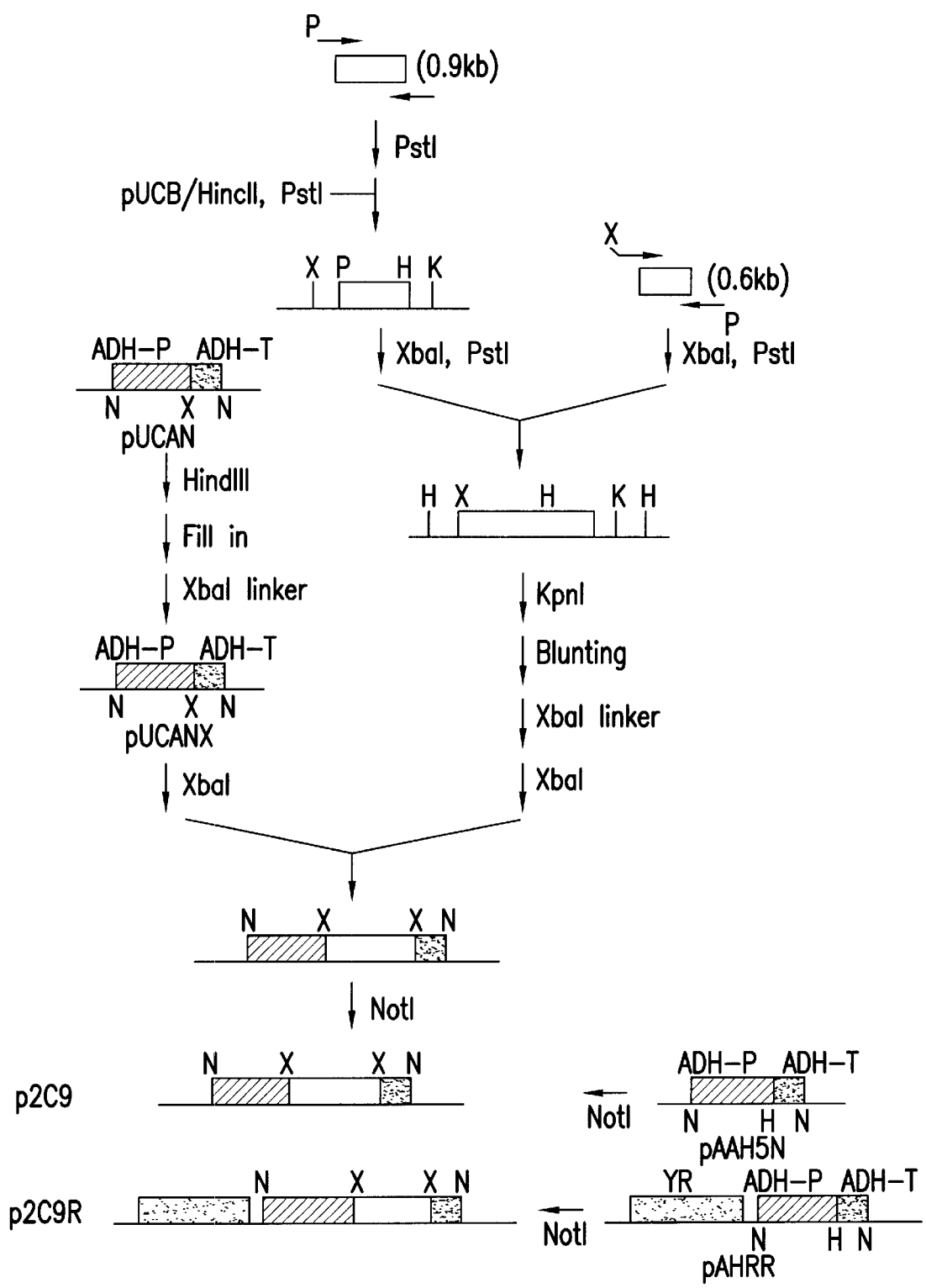
FIG. 7 shows a method of constructing yeast expression plasmids for human P450 2C9.

FIG. 7 shows a method of constructing yeast expression plasmids for human P450 2C9. The protein coding region of 450 2C9 gene was divided into two fragments of about 0.9 kb and about 0.6 kb, and the fragments were amplified by the PCR method using the primers shown in FIG. 1. The resultant fragment of about 0.9 kb was cleaved with PstI and sub-cloned to a pUC B vector, which was prepared by exchanging the cloning site located between the two HindIII sites, one of which was obtained by converting the EcoRI site of pUC19, with the following cloning sites:

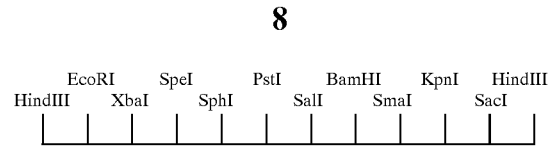

The fragment of about 0.6 kb was incorporated between the XbaI and PstI sites of the plasmid having the 0.9 kb fragment to ligate the two segments. The KpnI site of the plasmid was blunted. An XbaI linker was inserted to the blunted plasmid. The XbaI fragment containing the coding region was cut out from the resultant fragment. A modified pUC vector, pUCAN, was constructed by replacing the EcoRI and HindIII sites with NotI sites, followed by insertion of the NotI fragment prepared from pAAH5N between the two NotI sites. The HindIII site of pUCAN vector having the ADH promoter and terminator regions in the pUC vector was blunted and inserted into PUCANX introduced with the XbaI linker. The obtained plasmid was cleaved with NotI and inserted into pAAH5N and PAHRR treated in a similar manner with NotI to construct a yeast expression plasmid p2C9 for human P450 2C9, and a yeast expression plasmid p2C9R for simultaneous expression of human P450 2C9 and yeast NADPH-P450 reductase.

Construction of Yeast Expression Plasmids: p2E1 and p2E1R

Figure 8:
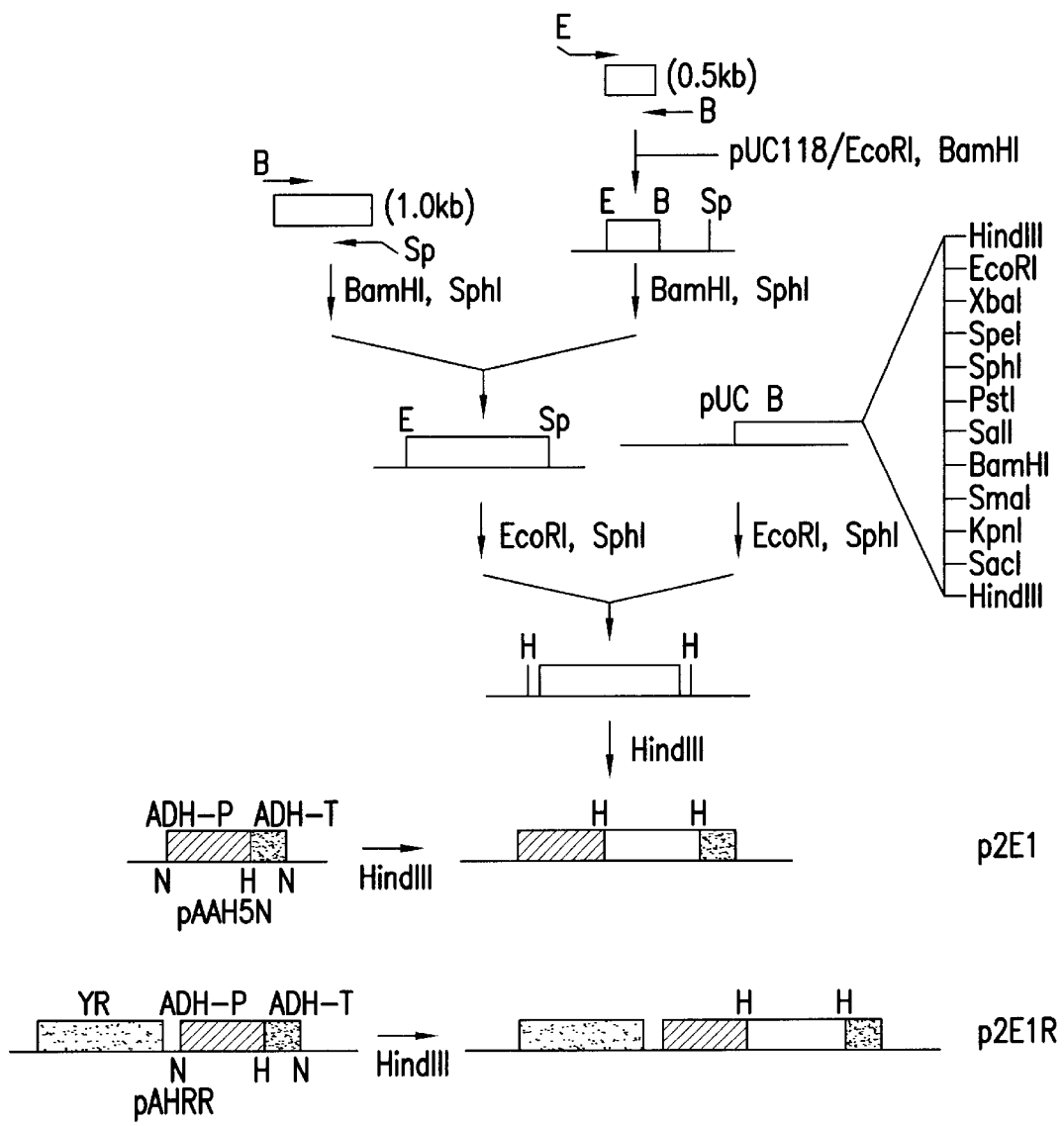
FIG. 8 shows a method of constructing yeast expression plasmids for human P450 2E1.

FIG. 8 shows a method of constructing yeast expression plasmids for human P450 2E1. The protein coding region of P450 2E1 gene was divided into two fragments of about 0.5 kb and about 1.0 kb, both of which were amplified by the PCR method using the primers shown in FIG. 1. The resultant fragment of about 0.5 kb was cleaved with EcoRI and BamHI and sub-cloned to a pUC118 vector. Then the fragment of about 1.0 kb was incorporated between the BamHI and SphI sites to ligate the two fragments. This was cleaved with EcoRI, and SphI, and inserted into pUC B first and then cut out with HindIII. The resultant fragment was inserted into pAAH5N and pAHRR vectors to construct a yeast expression plasmid p2El for human P450 2E1, and a yeast expression plasmid p2E1R for simultaneous expression of human P450 2E1 and yeast NADPH-P450 reductase.

Construction of Yeast Expression Plasmids: p3A4 and p3A4R

Figure 9:
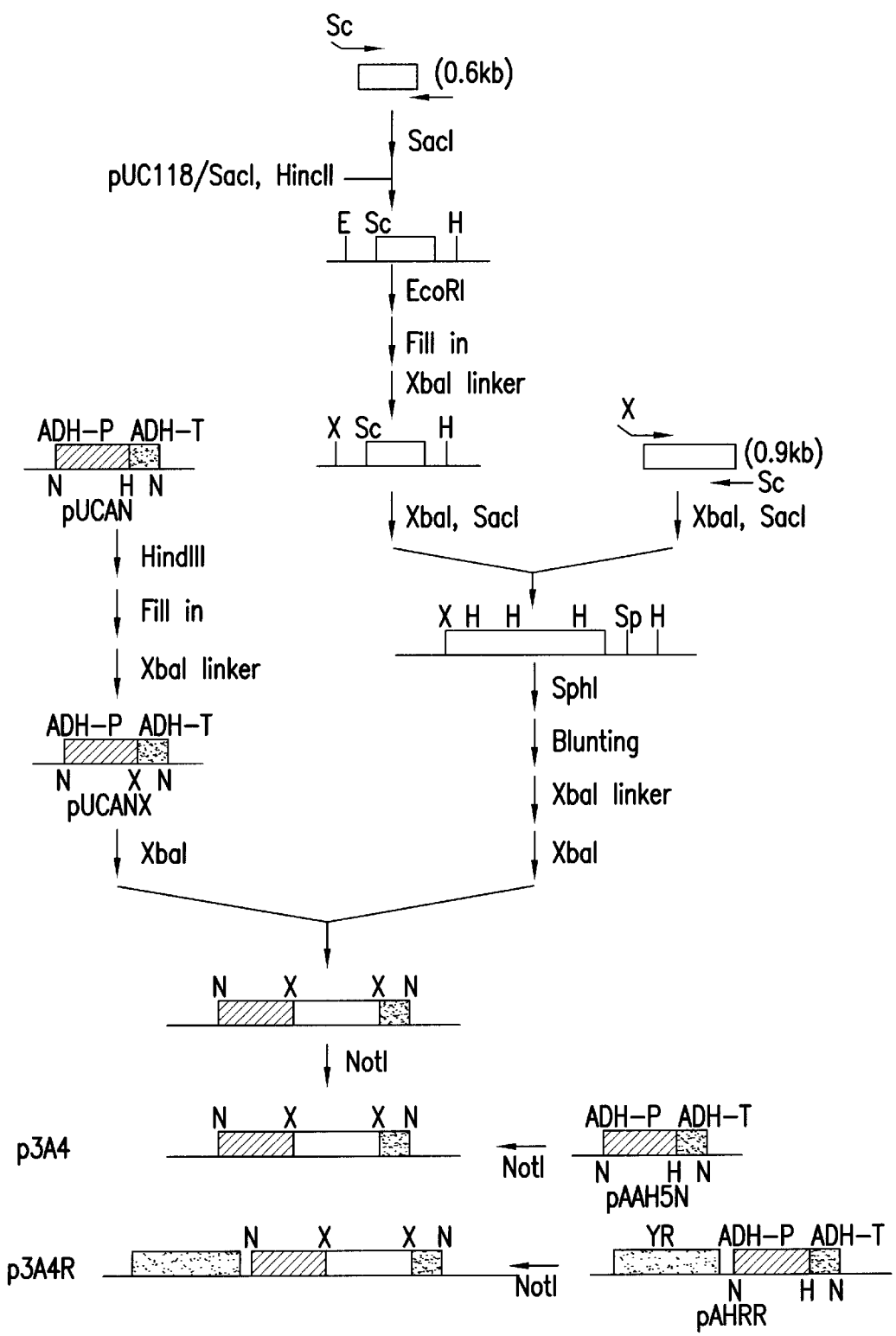
FIG. 9 shows a method of constructing yeast expression plasmids for human P450 3A4.

FIG. 9 shows a method of constructing yeast expression plasmids for human P450 3A4. The protein coding region of P450 3A4 gene was divided into two fragments of about 0.6 kb and about 0.9 kb, both of which were amplified by the PCR method using the primers shown in FIG. 2. The resultant fragment of about 0.6 kb was cleaved with SacI and sub-cloned to a pUC118 vector. Subsequently, it was cleaved with EcoRI and blunted. An XbaI linker was ligated to the blunted fragment. The fragment of 0.9 kb was cleaved with XbaI and SacI, and incorporated to the resultant fragment above, thus the two fragments were ligated. After cleaving the plasmid with SphI, it was blunted. An XbaI linker was ligated to the blunted fragment, from which the XbaI segment was cut out and inserted to an XbaI site of PUCANX. This was cut out with NotI and inserted into pAAH5N and PAHRR treated in a similar manner with NotI. Thus a yeast expression plasmid p3A4 for human P450 3A4, and a yeast expression plasmid p3A4R for simultaneous expression of human P450 3A4 and yeast NADPH-P450 reductase were constructed.

Construction of Yeast Expression Plasmids: p1A1 and p1A1R

Figure 10:
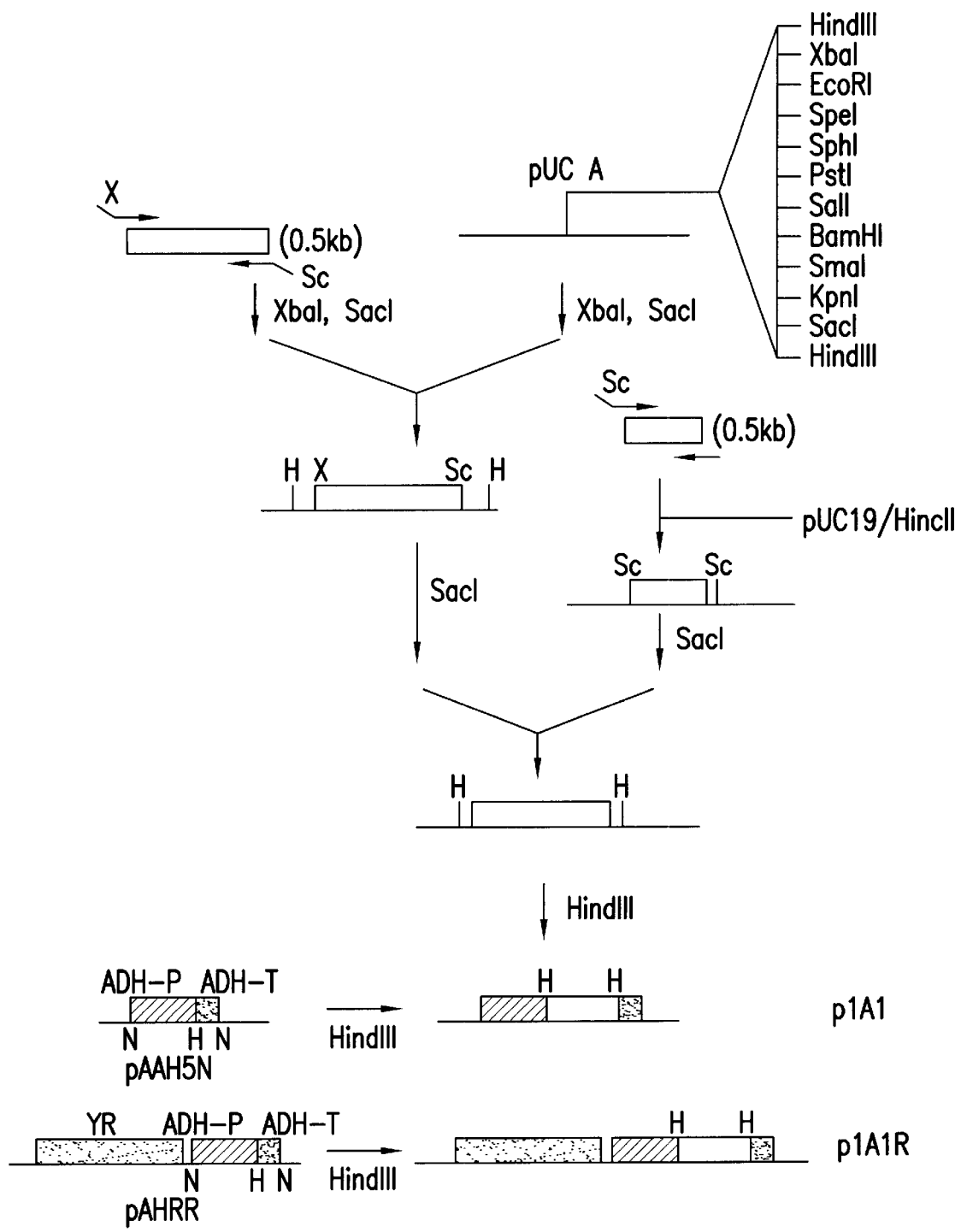
FIG. 10 shows a method of constructing yeast expression plasmids for human P450 1A1.

FIG. 10 shows a method of constructing yeast expression plasmids for human P450 1A1. The coding region for P450

1A1 protein was divided into two fragments of about 1.0 kb and about 0.5 kb and the resultant fragments were amplified by the PCR method using the primers shown in FIG. 2. Thus obtained fragment of about 1.0 kb was cleaved with XbaI and SacI and sub-cloned to a pUCA vector, which was prepared by exchanging the cloning site located between the two HindIII sites, one of which was obtained by converting the EcoRI site of pUC19, with the following cloning sites:

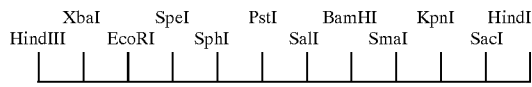

The amplified fragment of about 0.5 kb was sub-cloned into the HincII site of a pUC 19 vector and the resultant plasmid was then cleaved with SacI. The cleaved fragment was ligated with the plasmid having the 1.0 kb fragment. After cutting out the coding region from the thus obtained 1A1 gene with HindIII, the fragment was inserted to the HindIII site of the yeast expression vector pAAH5N having ADH promoter and terminator regions, and to the same site of vector pAHRR for simultaneous expression of P450 and yeast NADPH-P450 reductase of which gene is located upstream of the P450 gene. Thus yeast expression plasmid p1A1 for human P450 1A1 and yeast expression plasmid p1A1R for simultaneous expression of human P450 1A1 and yeast NADPH-P450 reductase were constructed.

In addition two kinds of human P450 1A1 gene fragments which were different only in a small portion of the nucleotide sequence were obtained in a similar manner and used to construct two kinds of yeast expression plasmid for human P450 1A1, p1A1 Variant 1 and p1A1 Variant 2, and two kinds of plasmids for simultaneous expression of human P450 1A1 and yeast NADPH-P450 reductase, p1A1R Variant 1 and p1A1R Variant 2.

Construction of Yeast Expression Plasmids: p2A6 and p2A6R

Figure 11:
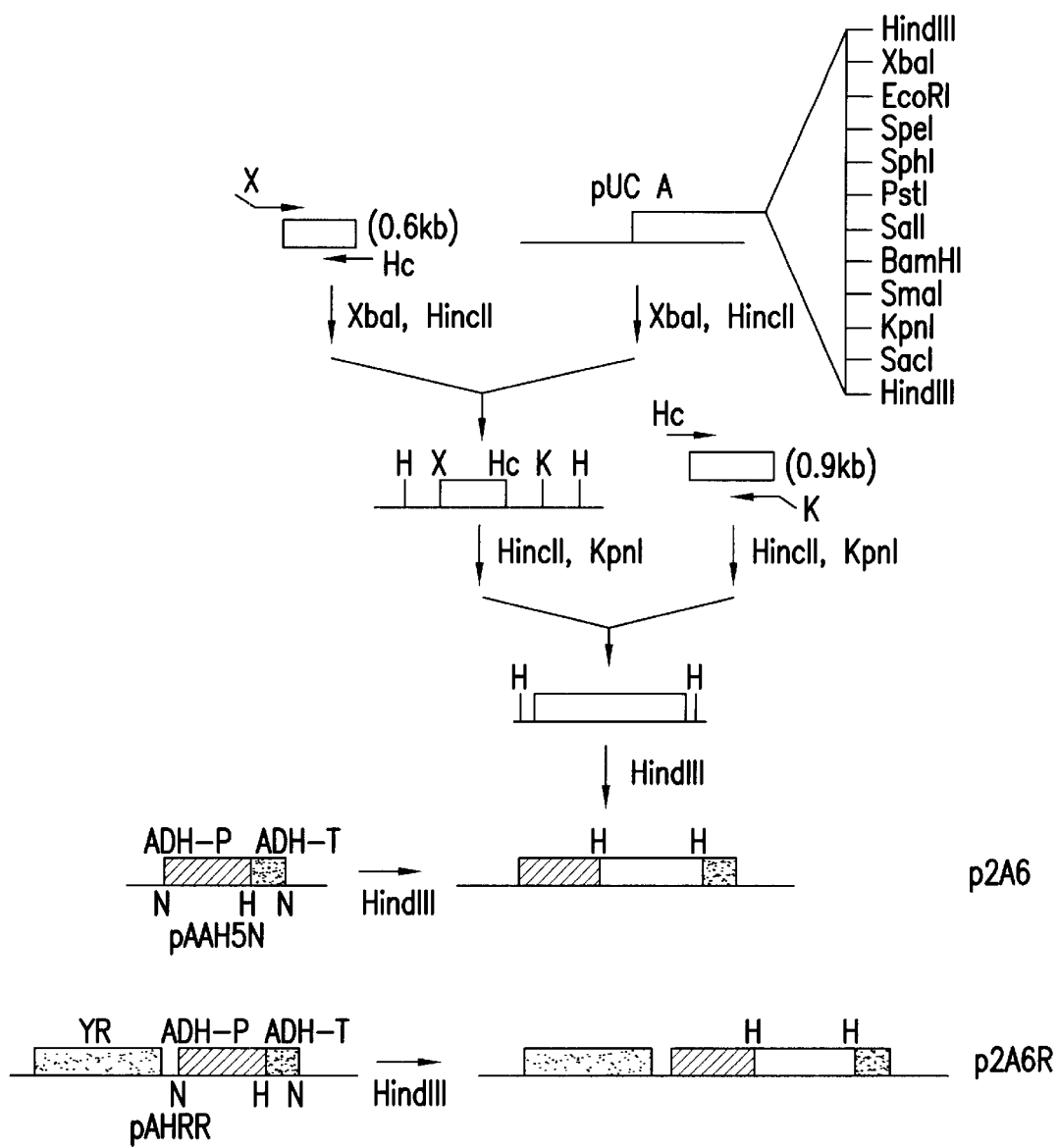
FIG. 11 shows a method of constructing yeast expression plasmids for human P450 2A6.

FIG. 11 shows a method of constructing yeast expression plasmids for human P450 2A6. A protein coding region of P450 2A6 gene was divided into two fragments of about 0.6 kb and about 0.9 kb, both of which were amplified by the PCR method using the primers shown in FIG. 2 to yield two kinds of human P450 2A6 gene fragments which were different only in a small portion of the nucleotide sequence. The resultant fragment of about 0.6 kb was cleaved with XbaI and HincII, and sub-cloned to a pUC A vector. Then the fragment of 0.9 kb was incorporated between the HincII and KpnI sites to ligate the two fragments. The obtained fragment was cleaved with HindIII and inserted into pAAH5N and pAHRR to construct two kinds of yeast expression plasmid for human P450 2A6, p2A6 and p2A6 Variant 1, and two kinds of yeast expression plasmid for simultaneous expression of human P450 2A6 and yeast NADPH-P450 reductase, p2A6R and p2A6R Variant 1.

Construction of Yeast Expression Plasmids: p2B6 and p2B6R

Figure 12:
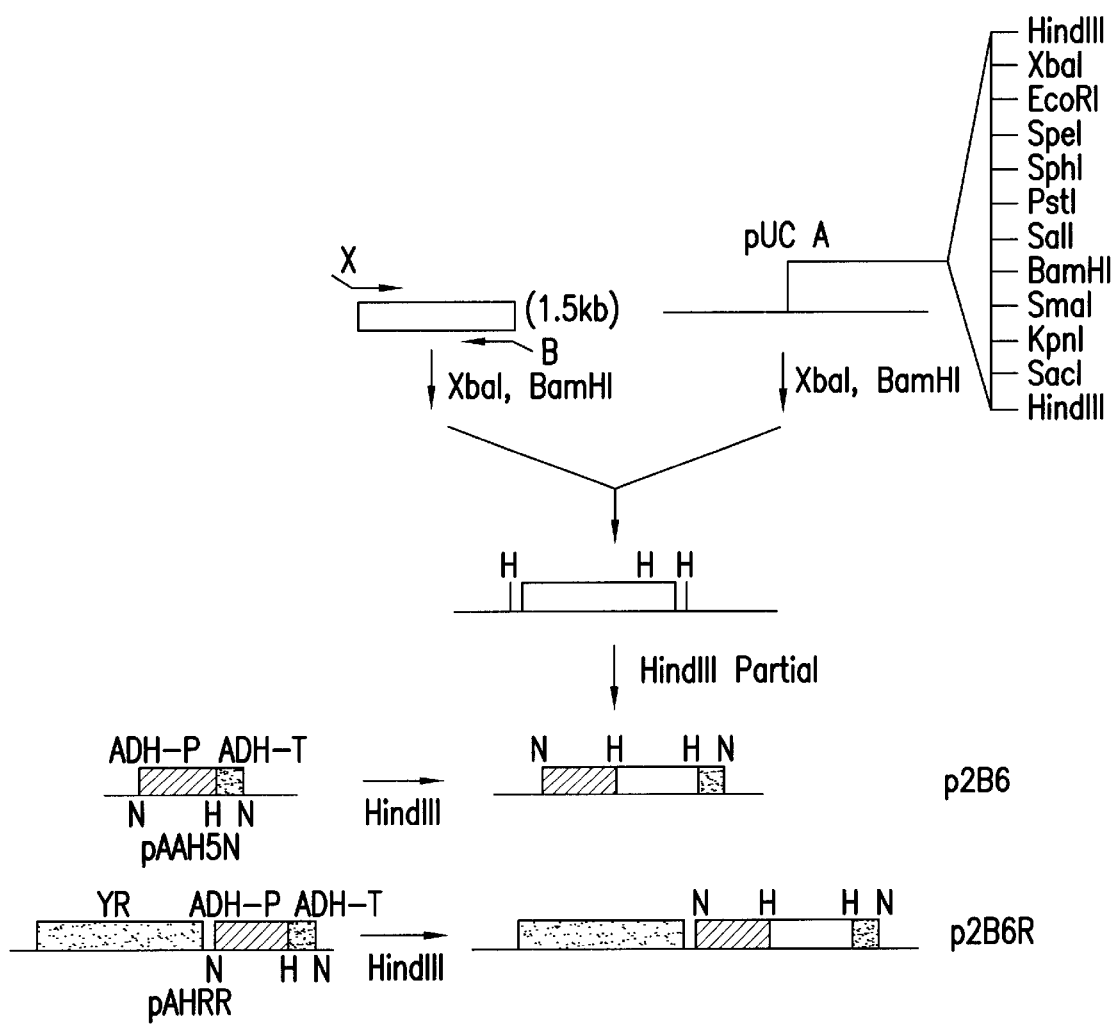
FIG. 12 shows a method of constructing yeast expression plasmids for human P450 2B6.

FIG. 12 shows a method of constructing yeast expression plasmids for human P450 2B6. The entire protein coding region of P450 2B6 gene was amplified by the PCR method using the primers shown in FIG. 3. The resultant fragment was cleaved with XbaI and BamHI and sub-cloned to pUC A. The resulting plasmid was partially digested with HindIII, and inserted into pAAH5N and PAHRR vectors to construct a yeast expression plasmid p2B6 for human P450 2B6, and a yeast expression plasmid p2B6R for simultaneous expression of human P450 2B6 and yeast NADPH-P450 reductase.

Construction of Yeast Expression Pplasmids: p2C8 and p2C8R

Figure 13:
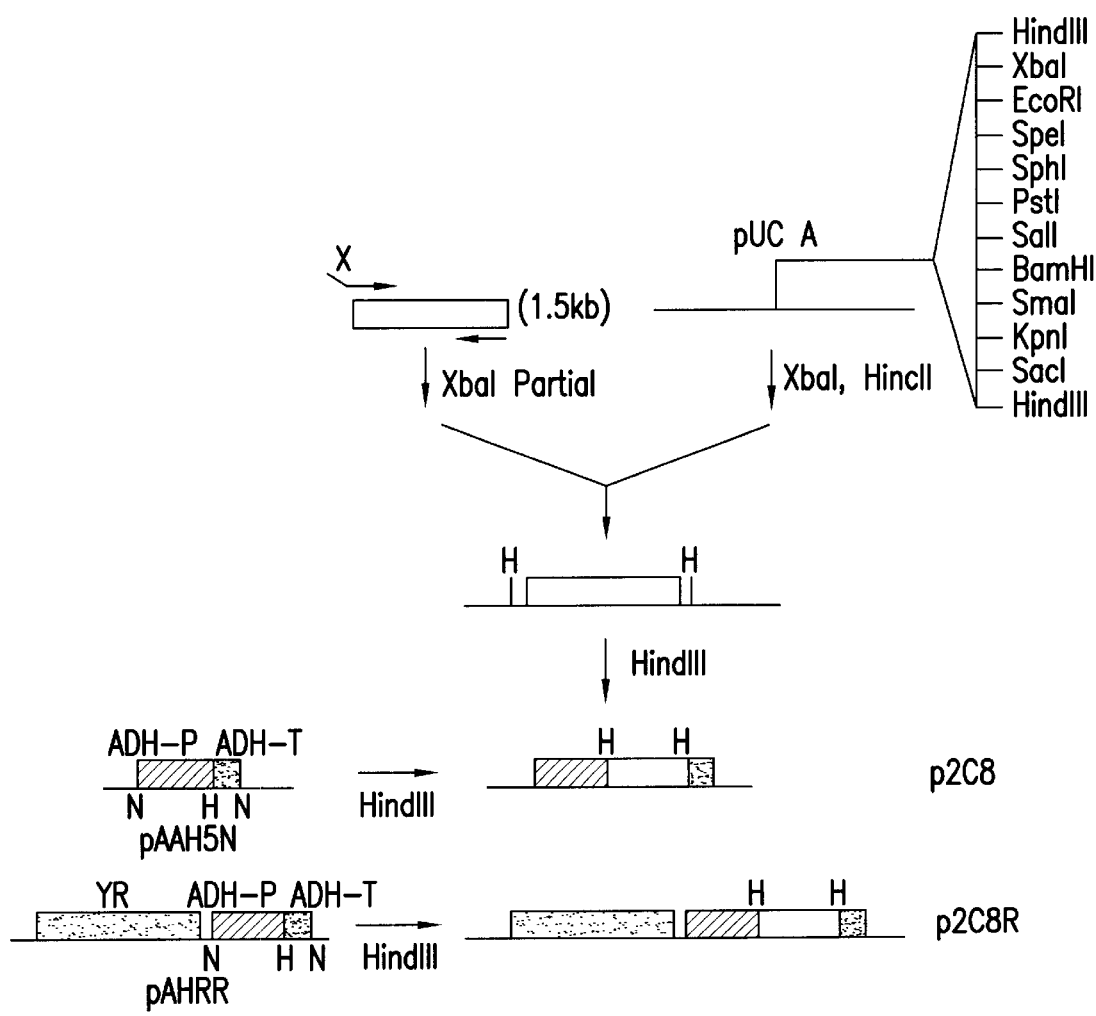
FIG. 13 shows a method of constructing yeast expression plasmids for human P450 2C8.

FIG. 13 shows a method of constructing yeast expressed plasmids for human P450 2C8. The entire protein coding region of the P450 2C8 gene was amplified by the PCR method using the primers shown in FIG. 3 to yield three kinds of P450 2C8 genes which were different only in a small portion of the nucleotide sequence. The resultant fragments were partially digested with XbaI, and sub-cloned to pUC A. The fragment was cleaved with HindIII and inserted into pAAH5N and pAHRR vectors to construct three kinds of yeast expression plasmids p2C8, p2C8 Variant 1 and p2C8 Variant 2 for human P450 2C8, and three kinds of yeast expression plasmids, p2C8R, p2C8R Variant 1 and p2C8R Variant 2 for simultaneous expression of human P450 2C8 and yeast NADPH-P450 reductase.

Construction of Yeast Expression Plasmids: p2C18 and p2C18R

Figure 14:
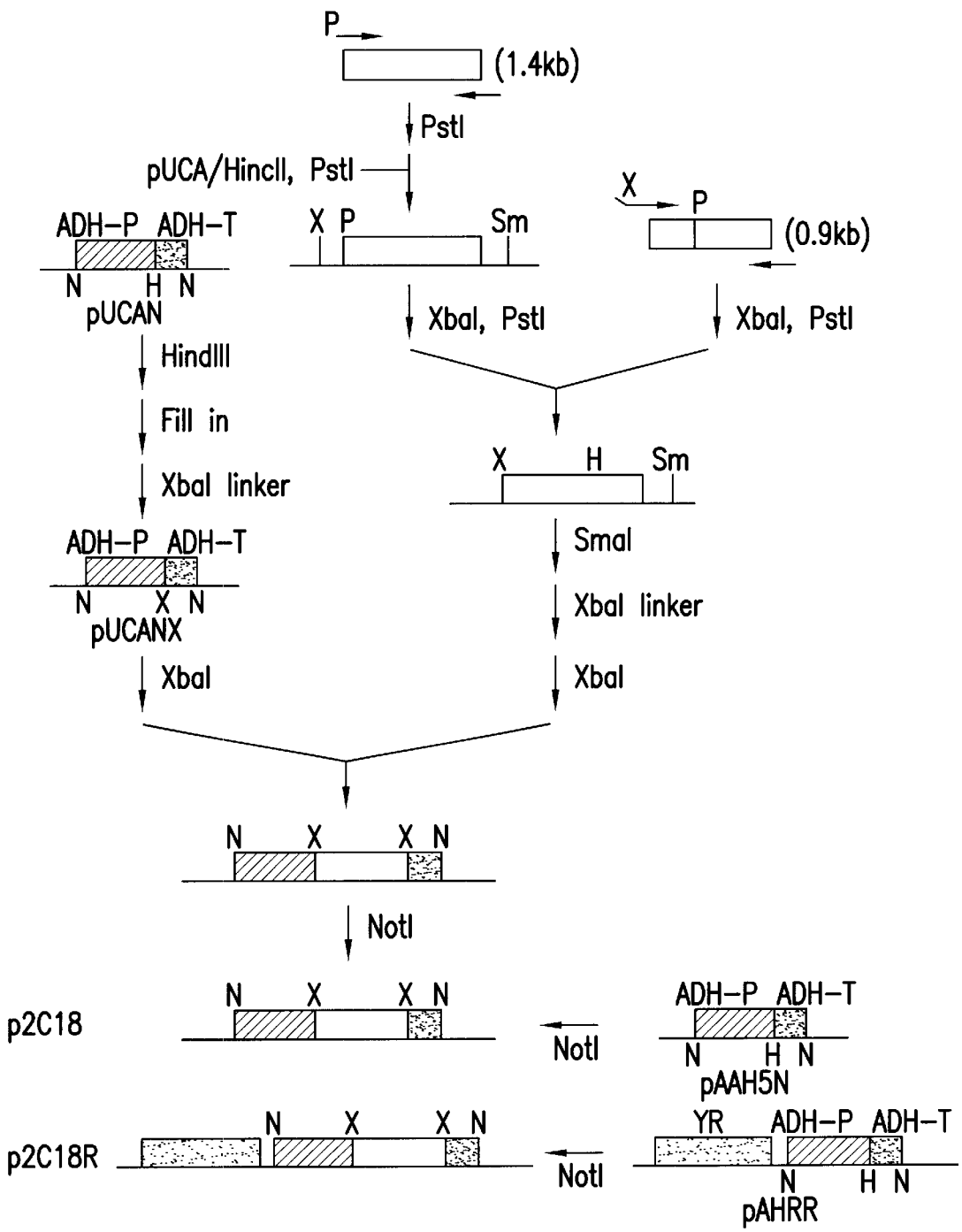
FIG. 14 shows a method of constructing yeast expression plasmids for human P450 2C18.

FIG. 14 shows a method of constructing yeast expression plasmids for human P450 2C18. The protein coding region of P450 2C18 gene was divided into two segment of about 1.4 kb and about 0.9 kb, then the both fragments were amplified by the PCR method using the primers shown in FIG. 3. The amplified fragment of about 1.4 kb was cleaved with PstI and sub-cloned to a pUC A vector. The fragment of about 0.9 kb was incorporated between the XbaI and PstI sites to ligate the two fragments. After cleaving the plasmid with SmaI, an XbaI linker was introduced. Then an XbaI fragment was prepared and inserted into the XbaI site of pUCANX. It was cleaved with NotI and inserted into pAAH5N and PAHRR treated in a similar manner with NotI to construct a yeast expression plasmid p2C18 for human P450 2C18, and a yeast expression plasmid p2C18R for simultaneous expression of human P450 2C18 yeast and NADPH-P4-50 reductase.

Construction of Yeast Expression Plasmids: p2C19 and p2C19R

Figure 15:
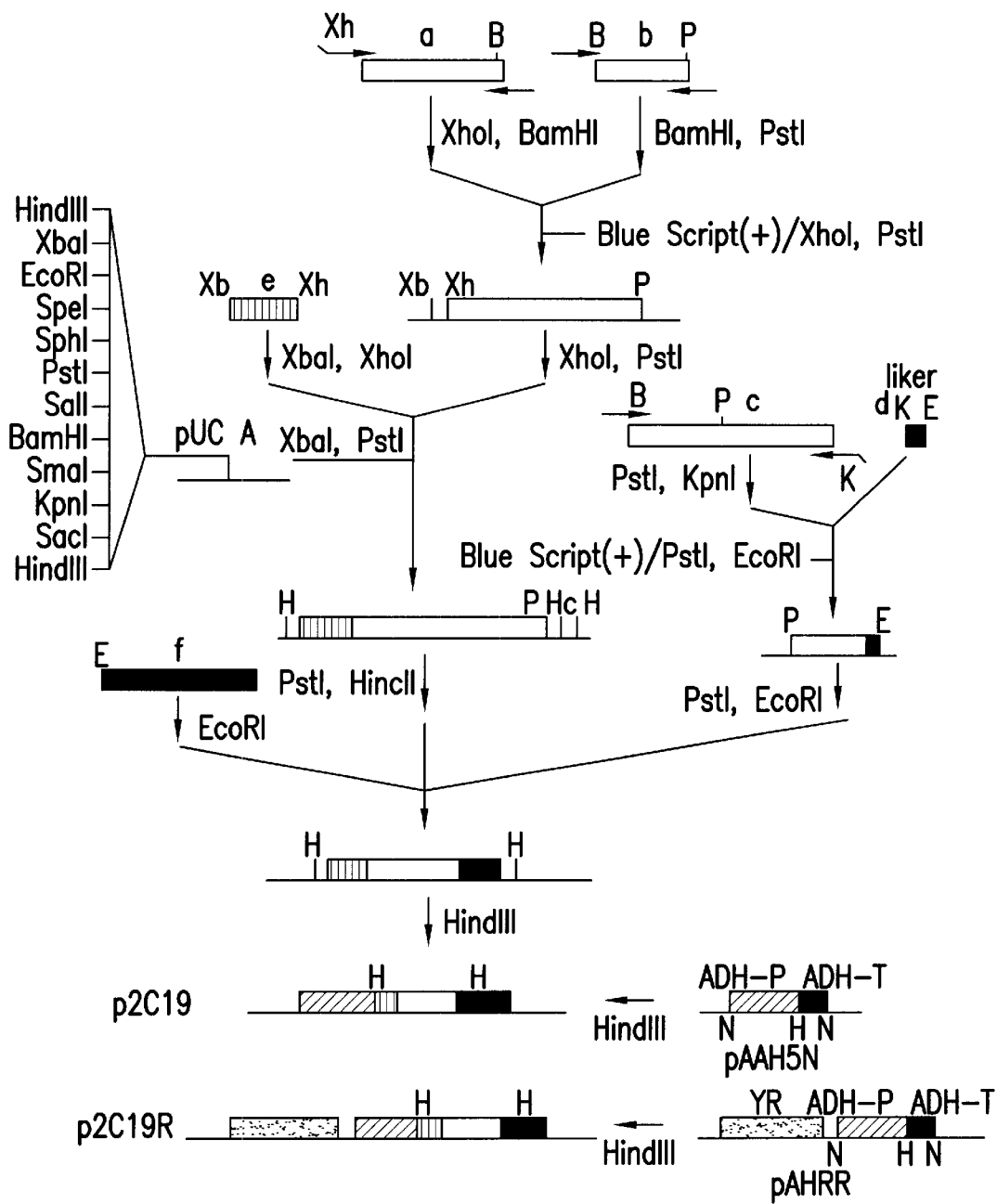
FIG. 15 shows a method of constructing yeast expression plasmids for human P450 2C19.

FIG. 15 shows a method of constructing yeast expression plasmids for human P450 2C19. Fragments a, b and c for the protein coding region of P450 2C19 gene were amplified by the PCR method using the primers No. 1, No. 2, No. 3 and No. 4, No.5 and No.6, and No.5 and No.7 defined by SEQ ID NOs: 20–26, respectively.

Fragments e and f for the protein coding region of human cytochrome P450 2C19 were also amplified against human cytochrome P450 2C9 gene by the PCR method using the primers No. 8 to 21 having nucleotide sequences with some mutations shown by SEQ ID NOs: 27 to 40. A fragment d for the linker Nos. 1 and 2 having nucleotide sequences shown by SEQ ID NOs: 41 and 42 was obtained by directly synthesizing the DNA to cover the rest of the protein coding region of the human P450 2C19 gene. Thus the fragments covering the whole protein coding region of the human cytochrome P450 2C19 were obtained.

After the fragments a and b were treated with XhoI and BamHI, and with BamHI and PstI, both fragments were simultaneously inserted between the XhoI and PstI sites of the Blue Script(+). The fragment e was treated with XbaI and XhoI and inserted to the XbaI and XhoI sites of the plasmid having the fragments a and b to give a plasmid having the fragments a, b and e.

After the fragment c was treated with PstI and KpnI, the resulting fragment was simultaneously inserted with the linker fragment d between the PstI and EcoRI sites of the Blue Script(+). The resultant plasmid was cut with PstI and EcoRI to give a fragment containing the fragments c and d. Then this fragment was simultaneously inserted between the fragment f treated with EcoRI to the PstI and HincII sites of the aforementioned plasmid containing the fragment a, b and e. Thus a plasmid having the whole coding region of the human cytochrome P450 2C19 gene was constructed. The constructed plasmid was cut with HindIII and the resultant fragment was inserted to pAAH5N and PAHRR both of which were treated with HindIII to give a yeast expression plasmid p2C19 for expressing the human P450 2C19 and a yeast expression plasmid p2C19R for simultaneous expression of the human P450 2C19 and yeast NADPH-P450 reductase.

SEQ ID NOs and primer Nos. are as follows:

| SEQ ID No: 20 | Primer No. 1 |
| SEQ ID NO: 21 | Primer No. 2 |
| SEQ ID NO: 22 | Primer No. 5 |
| SEQ ID NO: 23 | Primer No. 4 |
| SEQ ID NO: 24 | Primer No. 5 |
| SEQ ID NO: 25 | Primer No. 6 |
| SEQ ID NO: 26 | Primer No. 7 |
| SEQ ID NO: 27 | Primer No. 8 |
| SEQ ID NO: 28 | Primer No. 9 |
| SEQ ID NO: 29 | Primer No. 10 |
| SEQ ID NO: 30 | Primer No. 11 |
| SEQ ID NO: 31 | Primer No. 12 |
| SEQ ID NO: 32 | Primer No. 13 |
| SEQ ID NO: 33 | Primer No. 14 |
| SEQ ID NO: 34 | Primer No. 15 |
| SEQ ID NO: 35 | Primer No. 16 |
| SEQ ID NO: 36 | Primer No. 17 |
| SEQ ID NO: 37 | Primer No. 18 |
| SEQ ID NO: 38 | Primer No. 19 |
| SEQ ID NO: 39 | Primer No. 20 |
| SEQ ID NO: 40 | Primer No. 21 |
| SEQ ID NO: 41 | Linker No. 1 |
| SEQ ID NO: 42 | Linker No. 2 |

Construction of Yeast Expression Plasmids: p2D6 and P2D6R

Figure 16:
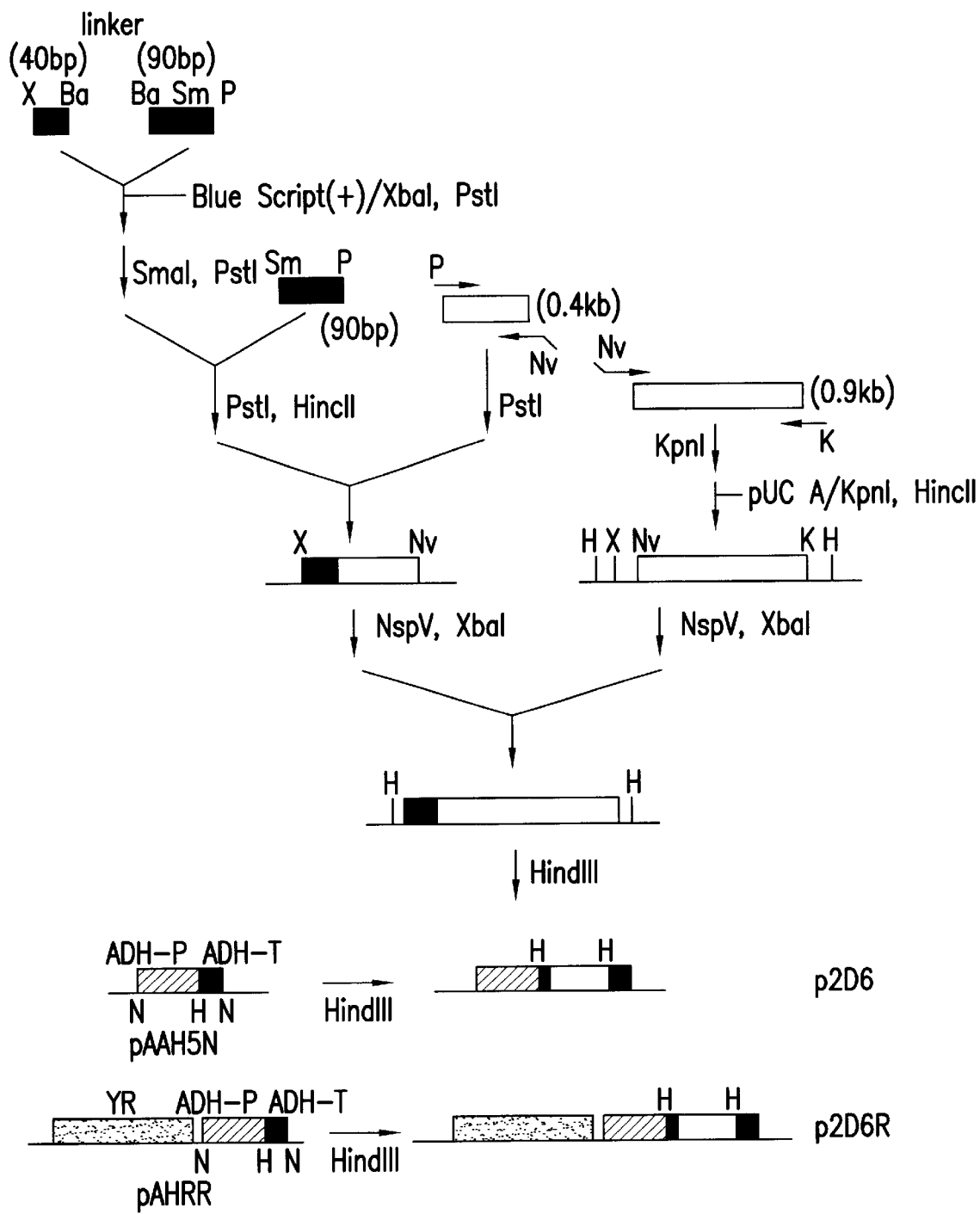
FIG. 16 shows a method of constructing yeast expression plasmids for human P450 2D6.

FIG. 16 shows a method of constructing yeast expression plasmids for human P450 2D6. The protein coding region of 1.3 kb excluding about 200 bp at the 5'-terminal of P450 2D6 gene was divided into two fragments of about 0.4 kb and about 0.9 kb, and the both fragments were amplified by the PCR method. The resultant fragment of about 0.9 kb was cleaved with KpnI and sub-cloned to pUC A. For the 200 bp on the 5'-terminal, three synthetic linkers shown in FIG. 5 were used and two linkers on the 5'-terminal were incorporated into XbaI and PstI sites of a Blue Script(+) vector and then other linkers were incorporated into SmaI and PstI sites. Then fragment of about 0.4 kb obtained by the PCR method was incorporated into the PstI and HincII sites of the plasmid and then cleaved with NspV and XbaI. The resultant fragment was inserted into the plasmid containing the 0.9 kb fragment to ligate the coding region. This was cleaved with HindIII and inserted into pAAH5N and pAHRR vectors to construct a yeast expression plasmid p2D6 for human P450 2D6, and a yeast expression plasmid p2D6R for simultaneous expression of human P450 2D6 and yeast NADPH-P450 reductase.

Then three kinds of human P450 2D6 gene fragments which were different only in a small portion of the nucleotide sequence were obtained in a similar manner as described above and used to construct two kinds of yeast expression plasmids for human P450 2D6, p2D6 Variant 1, p2D6 Variant 2 and p2D6 Variant 3, and three kinds of yeast expression plasmid 2D6R for simultaneous expression of human P450 2D6 yeast and NADPH-P450 reductase, p2D6R Variant 1, p2D6R Variant 2 and p2D6R Variant 3.

Figure 17:
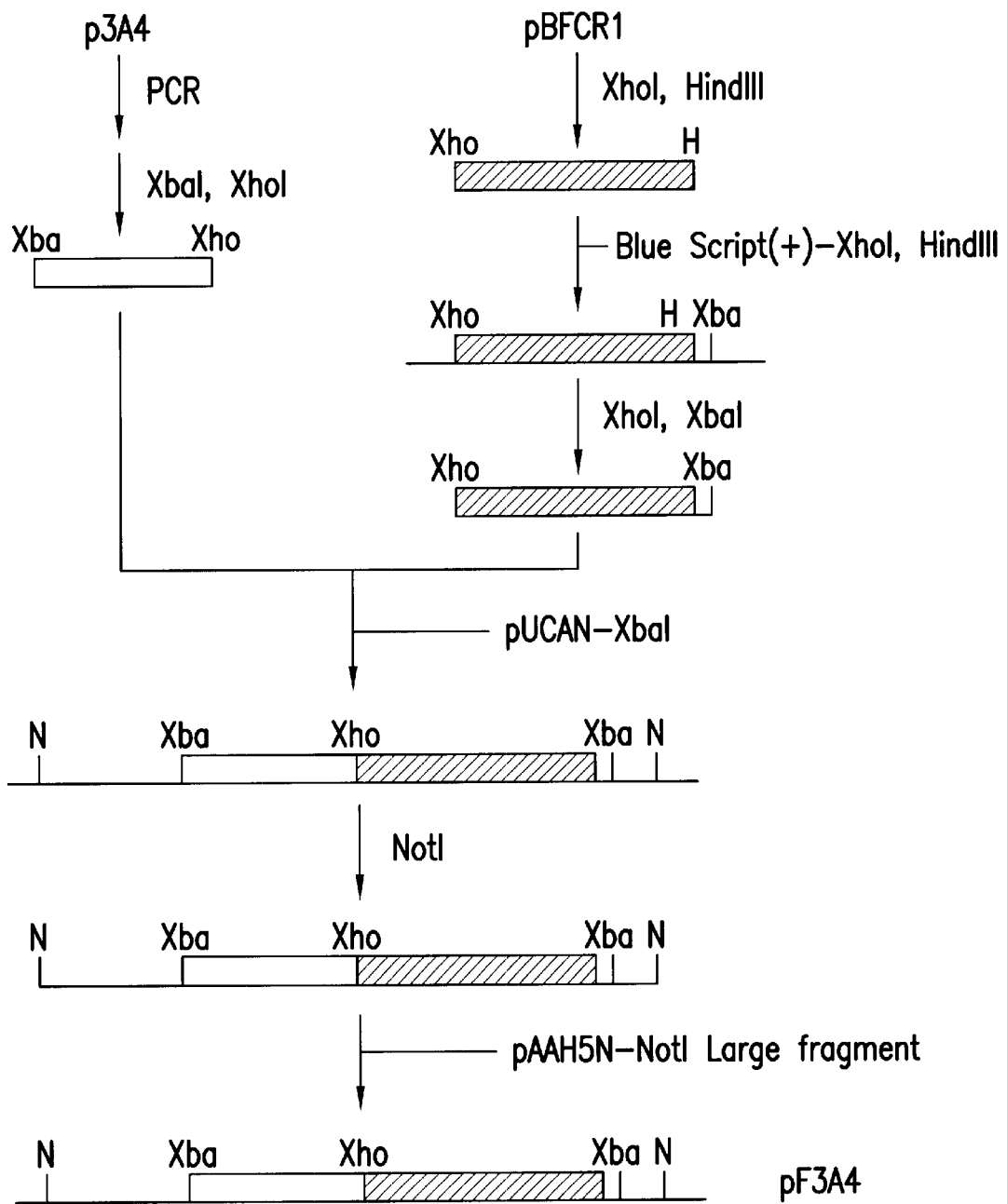
FIG. 17 shows a method of constructing a yeast expression plasmid containing an artificial fused enzyme gene.

Construction of Yeast Expression Plasmid Containing Artificial Fused Enzyme Gene An expression plasmid was constructed in accordance with FIG. 17. The XbaI-XhoI fragment was amplified with plasmid p3A4 by using the primers shown in FIG. 4. On the other hand, the XhoI-HindIII fragment of about 2.1 kb was obtained from the plasmid pBFCRI (Japanese Patent Application No. 4-209226) and inserted between the XhoI and HindIII sites of a commercial vector Blue Script(+), followed by digestion with restriction enzymes XhoI and XbaI. These two fragments were simultaneously inserted to the XbaI site of the vector pUCAN, which was then digested with NotI to give a fragment of about 5.6 kb. The desired yeast expression plasmid pF3A4 was obtained by ligating the fragment with the NotI fragment of about 10.5 kb obtained from vector pAAH5N (Japanese Patent Laid-open Publication No. 2-211880). The artificial fused enzyme consists of 1156 amino acid residues of which sequence structure comprising, successively, from the N-terminal end, an entire amino acid sequence (503 residues) of human liver cytochrome P450 3A4, a linker-derived sequence (Ala-Arg-Ala), and a sequence of from the 42nd residue to C-terminal of yeast NADPH-cytochrome P450 reductase.

Preparation of Transformed Yeast Cell

Saccharomyces cerevisiae AH 22 was inoculated to 1.0 ml of YPD culture medium (1% yeast extract, 2% polypeptone, 2% glucose). After shaken at 30 IC for 18 hours, the yeast cells were collected by centrifugation (5000×g, 10 min). The resultant cells were suspended in 10 ml of 0.2 M LiCl solution and then centrifuged again (5000×g, 10 min) to obtain pellets. Then 20 pl of 1 M LiCl solution, 30 1l1 of 70% polyethylene glycol 4000 and each 10 p1 solution containing about 1.0 $\mu$g of various kinds of yeast expression plasmids for the human P450 molecular species and yeast NADPH-reductase constructed as above were added to the resultant pellets. After sufficiently mixing them, they were incubated at 30° C. for one hour and further stirred after the addition of 140 $\mu$l of sterilized water. The solution was plated on SD synthetic culture medium (2.0% glucose, 0.67% nitrogen base w/o amino acids, manufactured by Difco Co., 20 $\mu$g/ml of histidine, 2.0% agar) and incubated at 30° C. for three days. Then transformed yeast cells possessing the yeast expression plasmid described above were selected. In this way, various kinds of yeast cells expressing the human P450 molecular species were prepared.

Quantitative Measurement of Human P450 Expressed in Yeast

Each 200 ml of culture broth of each kind of yeast cells expressing human P450 molecular species and yeast NADPH-reductase simultaneously or expressing an artificial fused enzyme comprising human P450 molecular species and yeast NADPH-reductase prepared as above (SD synthetic culture medium, cell concentration: about $1.5 \times 10^7$ cells/ml) was used to collect the cells. The collected cells were then suspended in 10 ml of 100 mM potassium phosphate buffer solution (pH 7.0) and centrifuged (5000×g, 10 min) to obtain pellets. Thus obtained pellets were resuspended in 2.0 ml of 100 mM potassium phosphate buffer solution (pH 7.0) and 1 ml of each of the solutions were poured into two cuvettes. After bubbling carbon monoxide to a sample cuvette, 5 to 10 mg of dithionite was added to both of the cuvettes, and stirred and then difference spectrum at 400–500 nm was measured to calculate the concentration of P450 present in the yeast. The amount of each kind of human P450 species or an artificial fused enzyme in each kind of transformed yeast cells was at a level from about 105 to about 106 molecules/cell.

Preparation of Yeast S-9 Mix Fraction, Cytoplasmic Fraction and Microsomal Fraction First, 3.8 liter of each kind of culture broth (SD synthetic culture medium, cell concentration: about $1.0 \times 10^8$ cells/ml) of yeast cells expressing human P450 molecular species and yeast NADPH-reductase simultaneously or an artificial fused enzyme comprising human P450 molecular species and yeast NADPH-reductase prepared as above was collected and the resultant cells were suspended in 400 ml of a buffer solution A (10 mM Tris-HCl (pH 7.5), 2 M sorbitol, 0.1 mM DTT, 0.2 mM EDTA), to which 160 mg of Zymolyase 100,000 (Zymolyase 100T) was added, and the obtained solution was incubated at 30° C. for 60 min. Spheroplast obtained by centrifugation (5000×g, 10 min) was suspended in 100 ml of the buffer solution A and then centrifuged (5000×g, 10 min). Washing the spheroplast by repeating the same centrifugal operation once again, the spheroplast was finally suspended in 200 ml of a buffer solution (10 mM Tris-HCl (pH 7.5), 0.65 M sorbitol, 0.1 mM DTT), which was then subjected to ultrasonic pulverization (50 W, for 5 min). The cell free extracts were centrifuged (9000×g, 20 min) and supernatants were recovered to obtain a yeast S-9 Mix fraction. Further, the fraction was centrifuged (125,000×g, 70 min) to collect precipitates which were suspended again into 10 ml of 0.1 M potassium phosphate buffer solution (pH 7.4) to obtain a microsomal fraction. On the other hand, a cytoplasmic fraction was obtained by recovering the supernatants.

Figure 18:
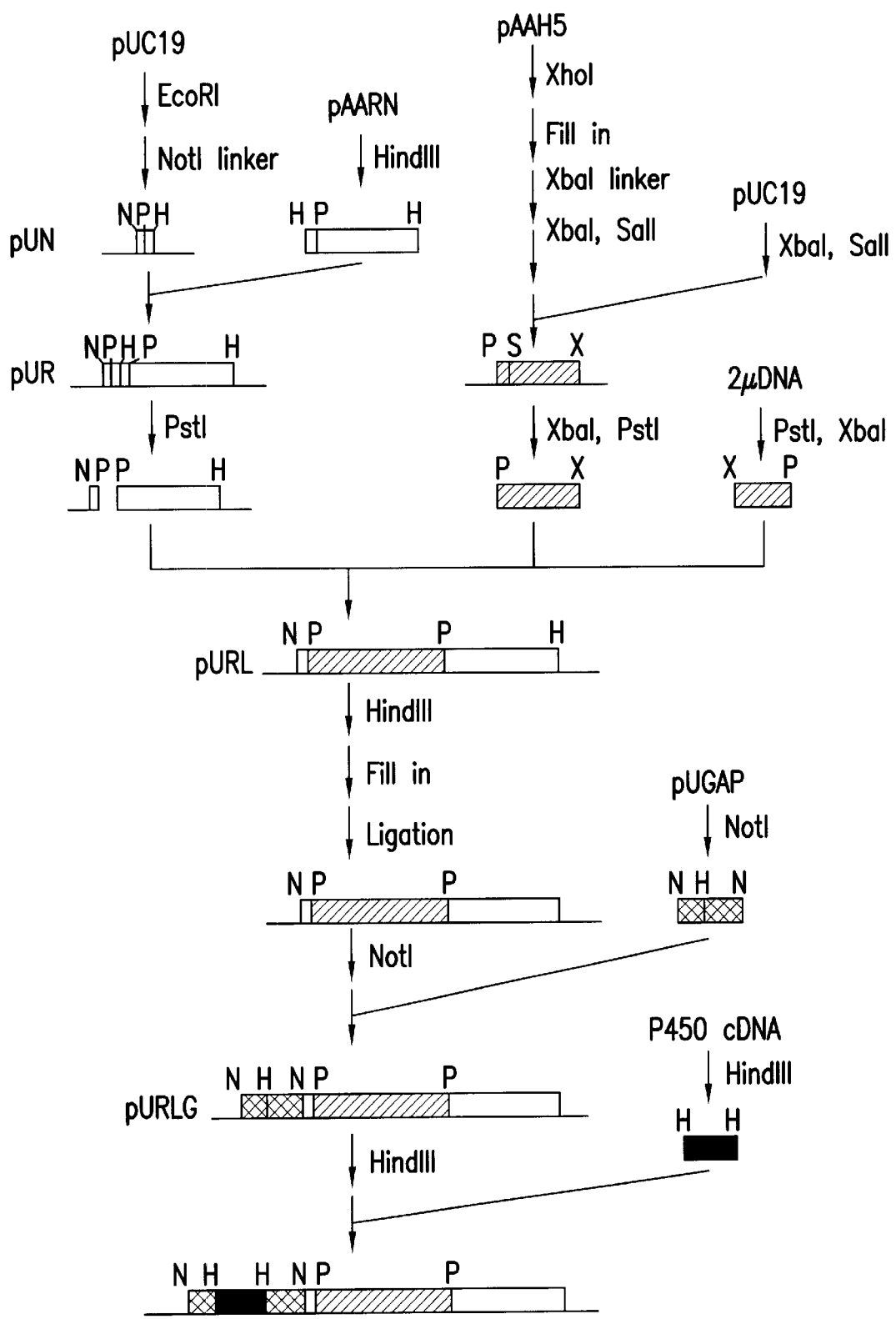
FIG. 18 shows a method of constructing a yeast expression plasmid using a GAPDH promoter.

Construction of Yeast Expression Plasmid using GAPDH Promoter and its Expression in Yeast FIG. 18 shows a method of constructing a yeast expression plasmid using a GAPDH promoter. A HindIII fragment (about 3.0 kb) obtained from PARRN (described in the Japanese Patent Laid-open Publication No. 2-211880) was inserted into a HindIII site of plasmid pUN, which was obtained by cleaving pUC19 with EcoRI, blunt-ending and ligation with an NotI linker to give pUR. On the other hand, after blunting an XhoI site of plasmid pAAH5 and inserting an XbaI linker, it was cleaved with restriction enzymes XbaI and SalI and the resultant fragment (about 2.2 kb) was inserted to XbaI and SalI sites of pUC19. The three fragments, namely, a fragment (about 2.2 kb) obtained by cleaving the resultant plasmid with XbaI and PstI, the XbaI-PstI fragment (about 1.3 kb) cut out from 2 $\mu$m DNA of Saccharomyces cerevisiae AH22, and a fragment obtained by cleaving pUR with PstI were ligated to give a plasmid pURL. Further, the pURL was cleaved with HindIII, blunted and ligated to remove the HindIII site. Then, an NotI fragment (about 1.6 kb) containing GAPDH promoter and terminator (obtained by the method as described in Agric. Biol. Chem., 51, 1641–1647 (1987) and J. Biol. Chem., 267, 16497–16502 (1992)) was ligated to the NotI site of pURL to give a plasmid pURLG. Human P450 2D6 cDNA obtained by the method used for the construction of p2D6 was inserted to a HindIII site of pURLG to obtain a yeast expression plasmid pG2D6R for simultaneous expression of human P450 2D6 and yeast NADPH-P450 reductase. When the plasmid was introduced by the method used in the preparation of transformed yeast cells as above to Saccharomyces cerevisiae AH22, production of human P450 2D6 was observed.

Metabolism of 7-Ethoxycoumarin Using Transformed Yeast Cells

7-Ethoxycoumarin was added to each 2 ml of the culture media of the transformed yeast cells expressing (i) human cytochrome P450 molecular species and yeast NADPH-P450 reductase; or (ii) an artificial fused enzyme comprising human cytochrome P450 molecular species and yeast NADPH-P450 reductase (SD synthetic culture medium, cell concentration: about $2.0 \times 10^7$ cells/ml) so that the final concentration of 7-eth-oxycoumarin was 0.5 mM. After incubation at 30° C. for 2 or 5 hours, supernatants were obtained by centrifugation (5000×g, 10 min). To the supernatants 62.5 $\mu$l of 15% TCA (trichlo-roacetic acid) and 2 ml of chloroform were added and, after well stirring, a chloroform layer was recovered by centrifugation (5000×g, 10 min), to which 4 ml of 0.01 N NaOH containing 0.1 M NaCl was added and stirred sufficiently and then centrifuged (5000×g, 10 min). After recovering the supernatants, fluorescence was measured for the supernatant fraction (ex. 366 nm, em 452 nm) to quantitatively measure the reaction product 7-hydroxycoumarin. As a result, O-deethylation activity for 7-ethoxycoumarin can be observed for all of 11 kinds of the yeast cells expressing the human P450 molecular species. P450 1A1 and P450 2B6 showed strong activity; and P450 1A2, P450 2E1, P450 2A6 and P450 2D6 showed good activity, while P450 2C8, P450 2C9, P450 3A4, P450 2C18 and P450 2C19 showed moderate activity.

Metabolism of Tolbutamide Using Transformed Yeast Cells

In the same manner as above, tolbutamide was added to each of the culture solutions of the transformed yeast cells expressing (i) human cytochrome P450 molecular species and yeast NADPH-P450 reductase; or (ii) an artificial fused enzyme comprising human cytochrome P450 molecular species and yeast NADPH-P450 reductase so that the concentration of the compound was 1.0 mM. After incubation at 30° C. for 15 hours, the culture supernatant was then obtained by centrifugation (5000×g, 10 min). To the supernatant, 2 ml of dichloromethane was added. After sufficient stirring, the dichloromethane layer was recovered by centrifugation (5000×g, 10 min), and the solvent was evaporated under reduced pressure. The resultant residue was dissolved in 100 $\mu$l of acetonitrile, and the solution was analyzed by HPLC under the following conditions. As a result, hydroxylated tolbutamide was detected in the solution of yeast cells expressing human P450 2C8, P450 2C9, P450 2C18 and P450 2C19. The human P450 2C9 showed high activity and 2C19 showed good activity. On the other hand, hydroxylated tolbutamide was not detected in the solution of yeast cells expressing other human P450 than described above.

Conditions for HPLC

Column: $\mu$Bondapak C18 (manufactured by Waters Co.)

Carrier: 10–70% acetonitrile-distilled water (linear concentration gradient for 20 min)

Temperature: 50° C.

Detection: UV 230 nm

Injection amount: 50 µl

Metabolism of Testosterone Using Transformed Yeast Cells

In the same manner as above, testosterone was added to each of the culture solutions of the transformed yeast cells expressing (i) human cytochrome P450 molecular species and yeast NADPH-P450 reductase; or (ii) an artificial fused enzyme comprising human cytochrome P450 molecular species and yeast NADPH-P450 reductase so that the concentration of the compound was 0.05 mM. After incubation at 30° C. for 15 hours, the supernatant was obtained by centrifugation (5000×g, 10 min). Then 2 ml of dichloromethane was added. After sufficient stirring, the solution was centrifuged again (5000×g, 10 min). The dichloromethane layer was recovered from the separated layer and the solvent was evaporated under reduced pressure. The resultant residue was dissolved in 100 µl of acetonitrile, and the solution was analyzed by HPLC under the following conditions. As a result, hydroxylated testosterone was detected for yeast cells expressing human P450 1A1, P450 2C8 and P450 3A4. On the other hand, hydroxylate testosterone was not detected for yeast cells expressing other human P450 than described above.

Conditions for HPLC

Column: µBondapak C18 (manufactured by Waters Co.)

Carrier: 20–70% acetonitrile-distilled water (linear concentration gradient for 25 min)

Temperature: 50° C.

Detection: UV 254 nm

Injection amount: 50 µl

Metabolism of Chlorzoxazone Using Transformed Yeast Cells and Microsomal Fractions Thereof Chlorzoxazone was added to each of the culture solutions of the transformed yeast cells expressing (i) human cytochrome P450 molecular species and yeast NADPH-P450 reductase; or (ii) an artificial fused enzyme comprising human cytochrome P450 molecular species and yeast NADPH-P450 reductase as above so that the concentration of the compound was 0.5 mM. After incubation at 30° C. for 15 hours, the supernatant was obtained by centrifugation (5000×g, 10 min). Then 2 ml of dichloromethane was added to the supernatant and vigorously stirred and centrifuged (5000×g, 10 min). The dichloromethane layer was recovered from the separated layer, then evaporated under reduced pressure. The obtained residue was dissolved in 100 µl of acetonitrile, and the solution was analyzed by HPLC under the following conditions.

NADPH and chlorzoxazone were added to a microsomal fraction of yeasts expressing (i) human cytochrome P450 molecular species and yeast NADPH-P450 reductase; or (ii) an artificial fused enzyme comprising human cytochrome P450 molecular species and yeast NADPH-P450 reductase prepared as above so that the concentrations of NADPDH and chlorzoxazone were 0.5 mM and 250 µM. Then the solutions were incubated at 37° C. for 10 min. After that, trichloroacetic acid was added to the solutions so that the concentration of the trichloroacetic acid was about 10% (v/v). Then 2 ml of dichloromethane was added to the solution, and the solution was stirred vigorously and centrifuged (15,000×g, 5 min). The dichloromethane layer was recovered, and the solvent was removed under reduced pressure. The obtained residue was dissolved in 100 µl of acetonitrile and the solution was subjected to analysis by HPLC under the same conditions as above.

All of the yeast cells expressing eleven human P450 molecular species gave hydroxylated chlorzoxazone. P450 2E1 showed high activity, and P450 1A1, P450 1A2, P450 2A6, P450 2D6 showed good activity, while P450 2C8, 2C9, 2B6, 2C18, 2C19 and 3A4 showed moderate activity.

Ames Test Using Yeast S-9 Mix Fraction and Microsomal Fraction

The Ames test method was in accordance with the customary method described, for example, in Mutat. Res., (1975) 31, 347. 2-Aminoanthrathene which is an arylamine type compound was used as a specimen compound. (1) Rat S-9 Mix supernatant fraction (obtained by homogenizing liver and then subjected to centrifugation (9000×g, 10 min), manufactured by Kikkoman) containing each kind of rat P450 molecular species at the concentration of 1200 pmol per 1 sample and (2) Yeast S-9 Mix fraction obtained from each kind of yeast cells expressing human P450 or a microsomal fraction prepared from the yeast S-9 Mix fraction were used as a metabolic activation source in the Ames test. As a result, more than 1000 revertant colonies were detected for the compound at 1 µg/plate (90 mm dia.) only in the case of using the yeast S-9 Mix fraction obtained from the yeast cells expressing human P450 1A2 (*Saccharomyces cerevisiae* AH22/p1A2R) and yeast cells expressing human P450 2E1 (*Saccharomyces cerevisiae* AH22/p2E1R) and a microsomal fraction prepared from the yeast S-9 Mix fraction, while the amounts of the human P450 molecules of these fractions were only one five hundredth and one thirtieth of the human P450 molecules present in the Rat S-9 mixture.

The human cytochrome P450 1A2 showed high activity, and human P450 2E1 showed only moderate activity. But the revertant colonies were not found for the human cytochrome P450 3A4, 2C8 and 2A6.

Metabolism of Acetanilide Using Transformed Yeast Cells

Acetanilide was added to each of the culture solutions of the transformed yeast cells expressing (i) human cytochrome P450 molecular species and yeast NADPH-P450 reductase; or (ii) an artificial fused enzyme comprising human cytochrome P450 molecular species and yeast NADPH-P450 reductase, so that the concentration of the compound was 5 mM, and the solution was incubated at 30° C. for 15 hours. Then the solution was centrifuged (5000×g, 10 min) to give a supernatant. The obtained supernatant solution was subjected to the HPLC analysis under the following conditions. The hydroxylated acetanilide was found for all of the tested eleven human P450 molecular species.

Among them, P450 1A2 and 2D6 showed high activity and P450 1A1, 2A6, 2B6, 2C8, 2C9, 2C18, 2C19 and 2E1 showed good activity, while 3A4 showed moderate activity.

Conditions for HPLC

Column: µBondapak C18 (manufactured by Waters Co.)

Carrier: Methanol:water:acetic acid=15:84:1

Temperature: 30° C.

Detection: UV 254 nm

Injection amount: 50 µl

Metabolism of Coumarin Using Transformed Yeast Cells

Coumarin was added to 6 ml of each of the culture solutions (SDS synthetic culture medium, cell concentration of about $2.0 \times 10^7$ cells/ml) of the transformed yeast cells expressing (i) human cytochrome P450 molecular species and yeast NADPH-P450 reductase; or (ii) an artificial fused enzyme comprising human cytochrome P450 molecular species and yeast NADPH-P450 reductase prepared as above, so that the concentration of the compound was 5 mM, and the solution was incubated at 30° C. for 2 or 5 hours. Then the solution was centrifuged (5000×g, 10 min) to give a supernatant. 62.5 μl of 15% trichloroacetic acid and 2 ml of chloroform were added to the obtained supernatant solution, and the resultant solution was stirred well. The chloroform layer was recovered from the separated layer. Then 4 ml of sodium hydroxide solution containing 0.1 M NaCl was added to the solution and centrifuged again (5000×g, 10 min). The supernatant fraction was recovered and subjected to fluorescence analysis (ex. 366 nm, em. 452 nm) to measure the 7-hydroxycoumarin formed. The hydroxylation activity was specifically found only for the yeast cells expressing the human P450 2A6, while other yeast cells showed no activity.

Metabolism of Debrisoguine Using the Microsomal Fraction of Transformed Yeast Whole Cells NADPDH and [$^{14}$C]debrisoquine were added to each microsomal fraction solution of (i) human cytochrome P450 molecular species and yeast NADPH-P450 reductase; or (ii) an artificial fused enzyme comprising human cytochrome P450 molecular species and yeast NADPH-P450 reductase prepared as above, so that the concentration of the compound was 100 μM and that of NADPH is 6 mM, and the solution was incubated at 30° C. for 30 minutes. Then perchlorate was added to the solution, so that the final concentration of the perchlorate was 10% (v/v). The solution was sufficiently stirred and centrifuged (15,000×g, 15 min) to give the supernatant. The obtained supernatant was subjected to HPLC analysis according to the following conditions.

Microsomal fractions of yeasts expressing P450 1A1 and 2D6 showed good activity for the hydroxylation of the debrisoquine, while those of yeast cells expressing other human P450 molecular species showed no activity.

Conditions for HPLC

Column: COSMOSIL 5C18 (manufactured by Nakarai Tesq Co.)

Carrier: A(acetonitrile)/B(20mM Sodium Perchlorate, pH=2.5)

| Time (minute) | A/B |
|---|---|
| 0–15 | 9/91 |
| 15–30 | 9/91–25/75 (linear gradient) |
| 30–32 | 100/0 |
| 32–42 | 9/91 |

Temperature: room temperature

Detector: RI $^{14}$C

Injection amount: 100 μl

Metabolism of S-mephenytoin Using the Microsomal Fraction of Transformed Yeast Cells NADPH and [$^{14}$C]S-mephenytoin were added to each microsomal fraction solution of (i) human cytochrome P450 molecular species and yeast NADPH-P450 reductase; or (ii) an artificial fused enzyme comprising human cytochrome P450 molecular species and yeast NADPH-P450 reductase prepared as above, so that the concentration of the compound was 25 μM and that of NADPH was 3 mM, and the solution was incubated at 30° C. for 30 minutes. Then the solution was diluted with equal volume of methanol, sufficiently stirred and centrifuged (15,000×g, 5 min) to give the supernatant. The obtained supernatant was subjected to HPLC analysis according to the following conditions.

Microsomal fractions of yeasts expressing P450 2C19 showed good activity for the hydroxylation of the S-mephenytoin, while those of yeast cells expressing other human P450 molecular species showed no activity.

Conditions for HPLC

Column: COSMOSIL 5C18 (manufactured by Nakarai Tesq Co.)

Carrier: A:(Methanol)/(20 mM Potassium phosphate buffer, pH=7.0)=40/60 B: Methanol

| Time (minute) | A/B |
|---|---|
| 0–18 | 100/0 |
| 18–20 | 0/100 |
| 20–35 | 100/0 |

Temperature: room temperature

Detector: RI $^{14}$C

Specimen amount: 100 μl

TABLE 1

Results of the hydroxylation activity using human P450 molecular species

| Substrate | Human P450 molecular species | | | | | | | | | | |
|---|---|---|---|---|---|---|---|---|---|---|---|
| | 1A2 | 2C9 | 2E1 | 3A4 | 1A1 | 2A6 | 2B6 | 2C8 | 2C18 | 2C19 | 2D6 |
| 7-Ethoxycoumarin | ++ | + | ++ | + | +++ | ++ | +++ | + | + | + | ++ |
| Tolbutamide | − | +++ | − | − | − | − | − | + | + | ++ | − |
| Testosterone | − | − | − | +++ | + | − | − | + | − | − | − |
| Chlorzoxazone | ++ | + | +++ | + | ++ | ++ | + | + | + | + | ++ |
| 2-Aminoanthracene | +++ | * | ++ | − | * | − | * | − | * | * | * |
| Acetanilide | +++ | ++ | ++ | + | ++ | ++ | ++ | ++ | ++ | ++ | +++ |
| Coumarin | − | − | − | − | − | +++ | − | − | − | − | − |

TABLE 1-continued

Results of the hydroxylation activity using human P450 molecular species

| | Human P450 molecular species | | | | | | | | | | |
|---|---|---|---|---|---|---|---|---|---|---|---|
| Substrate | 1A2 | 2C9 | 2E1 | 3A4 | 1A1 | 2A6 | 2B6 | 2C8 | 2C18 | 2C19 | 2D6 |
| Debrisoquine | – | – | – | – | + + | – | – | – | – | – | + + + |
| S-Mephenytoin | – | – | – | – | – | – | – | – | + + + | – |

Hydroxylation activity is designated as follows:
+, moderate activity; + +, good activity; + + +, high activity; –, no activity; *, not examined.

Metabolism of Chlorzoxazone Using a Mixture of Microsomal Fractions of Transformed Yeast Cells Microsomal fractions of yeast expressing cytochrome P450 prepared as above were mixed in the following molar ratios, and the hydroxylation activities of the mixed solutions were measured using chlorzoxazone.

| P450 | System A | System B |
|---|---|---|
| 3A4 | 35% | 33% |
| 2C9 | 25% | 5.8% |
| 2C8 | | 5.8% |
| 2C18 | | 5.8% |
| 2C19 | | 5.8% |
| 1A2 | 23% | 19% |
| 2E1 | 17% | 15% |
| 1A1 | | 2.4% |
| 2A6 | | 3.0% |
| 2B6 | | 2.4% |
| 2D6 | | 2.4% |

The substrate, [$^{14}$C]chlorzoxazone and NADPH were added to the mixed yeast microsomal fractions, so that the concentrations of the compound and NADPH were 382 M and 3 mM. The solutions were incubated at 37° C. for 30 min, and then 1 ml of dichloromethane was added thereto to stop the reaction. After stirring, dichloromethane layer was recovered by centrifugation (10,000×g, 5 min). Then the solvent was evaporated by the stream of nitrogen gas. The obtained residue was dissolved in 54 μl of acetonitrile and 146 μl of water, the solution was subjected to HPLC analysis under the following conditions.

Conditions for HPLC
Column: COSMOSIL 5C18 (manufactured by Nakarai Tesq Co.)
Carrier: A(Acetonitrile/Water=27/73) B(Acetonitrile)

| Time (minute) | A/B |
|---|---|
| 0–15 | 100/0 |
| 15–17 | 0/100 |
| 17–25 | 100/0 |

Temperature: room temperature
Detector: RI $^{14}$C
Injection amount: 100 μl

The metabolites of chlorzoxazone observed by each of the mixed systems A and B were similar to those metabolites which Guengerich reported based on their experimental results by using human liver microsomal fractions (Guengerich, F. P., Chem. Toxicil., Vol.3, pp.566–573, 1990).

Furthermore, the metabolic turnover numbers were calculated for the human liver microsomal fraction (by Guengerich) and for the present yeast microsomal fractions.

The turnover numbers were calculated to be 1.8 and 1.6 in the mixed systems A and B, respectively. The turnover V for the human liver microsomal fraction was calculated using $V_{max}$, $K_m$ and substrate concentration [S] described in the literature according to the following manner. The results are shown in Table 2. The values somewhat varied due to the difference of individuals, the lowest value being 1.0 and the highest value being 5.9. The values of V for the mixed system B and A fell within this range, both of which were the same level. It was confirmed that the four kinds of molecular species in system A can well reproduce the metabolic system in human liver in vitro.

A turnover V for human cytochrome P450 at an optional substrate concentration can be calculated by substituting $V_{max}$ and $K_m$ described in the literature and substrate concentration [S] of the present example into the Michaelis-Menten's equation:

$$V=(V_{max}*[S])/(K_m+[S])$$

TABLE 2

| Liver sample | Metabolic turnover V [product mnol/mnol P450/min] |
|---|---|
| #1001 | 5.9 |
| KDL 14 | 2.2 |
| KDL 21 | 1.7 |
| KDL 23 | 3.0 |
| KDL 27 | 5.0 |
| H 10 | 1.1 |
| H 11 | 1.0 |
| H 12 | 4.2 |
| H 13 | 3.3 |
| H 14 | 2.1 |
| H 15 | 4.3 |
| H 16 | 4.0 |
| H 17 | 3.6 |
| H 18 | 3.4 |

Designations of the human liver sample were those used by Guengerich.

Metabolism of Debrisoguine Using Mixture of Microsomal Fractions of Transformed Yeast Cells Microsomal fractions of yeasts expressing human cytochrome P450 were mixed, and the hydroxylation activity of the mixed fraction was measured using debrisoquine. The mixing molar ratio of the human cytochrome P450 molecular species were as follows:

| P450 | Molar ratio |
|------|-------------|
| 3A4  | 33%         |
| 2C9  | 5.8%        |
| 2C8  | 5.8%        |
| 2C18 | 5.8%        |
| 2C19 | 5.8%        |
| 1A2  | 19%         |
| 2E1  | 15%         |
| 1A1  | 2.4%        |
| 2B6  | 2.4%        |
| 2D6  | 2.4%        |

The substrate debrisoquine and NADPH were added to the mixed microsomal fraction solutions, so that the concentrations were 100 µM for the NADPH and 6 mM for the compound. After the mixture was incubated at 37° C. for 30 min, 50 µl of 60% perchlorate was added to the solution to stop the reaction. The concentration of the perchlorate was finally 12.5% (v/v). After vigorous stirring, the mixture was centrifuged (15,000×g, 5 min) to recover the supernatant, which was subjected to HPLC analysis under the same conditions used for analyzing the metabolites of debrisoquine.

The metabolites well coincided with the metabolites which Kronbach reported based on the experiments to metabolize the debrisoquine using the human liver microsome (Methods in Enzymology, Vol.206, pp.509–517, 1991).

Metabolism of S-mephenytoin Using Mixture of Microsomal Fractions of Transformed Yeast Cells Microsomal fractions of yeasts expressing various human cytochrome P450 prepared were mixed, and the hydroxylation activity of the mixed fraction was measured for S-mephenytoin. The mixing ratio of the human cytochrome P450 molecular species was the same as that of the mixing system B as described above.

The substrate, [$^{14}$C]S-mephenytoin and NADPH were added to the mixed microsomal fraction solutions, so that the concentrations were 28 µM for the NADPH and 6 mM for the compound. After the mixture was incubated at 37° C. for 30 min, 250 µl of methanol was added to the solution to stop the reaction. After vigorous stirring, the mixture was centrifuged (15,000×g, 5 min) to recover the supernatant, which was subjected to HPLC analysis under the same conditions used for the hydroxylation of S-mephenytoin using microsomal fraction. The metabolites obtained well coincided with the metabolites which Goldstein reported based on the experiments to metabolize the S-mephenytoin using the human liver microsome (Biochemistry, Vol.33, pp.1743–1752, 1994).

What is claimed is:

1. A method for evaluation of the safety of a chemical compound, which comprises:
   (a) reacting the chemical compound with recombinant yeast cells that produce the four human cytochrome P450 molecular species consisting of P450 1A2, P450 2C9, P450 2E1 and P450 3A4 and a yeast NADPH-P450 reductase, wherein said yeast NADPH-P450 reductase is optionally in the form of a fused enzyme with each of said human cytochrome P450 molecular species, or reacting the chemical compound with cell free extracts of the yeast cells; and
   (b) analyzing the resulting metabolite to determine the safety of the compound.

2. A method according to claim 1, wherein the recombinant yeast cells are yeast cells transformed with a plurality of plasmids, wherein each plasmid comprises a gene coding for human cytochrome P450 1A2, P450 2C9, P450 2E1 or P450 3A4 and a gene coding for yeast NADPH-P450 reductase.

3. A method according to claim 1, wherein the recombinant yeast cells are yeast cells transformed with a plurality of plasmids, each of which has a fused gene comprising a gene coding for one of said human cytochrome P450 molecular species located 5' to a gene coding for the yeast NADPH-P450 reductase.

4. A method according to claim 1, wherein the analyzing of the metabolite is carried out by the Ames Test.

5. A method according to claim 4, wherein the test is carried out using His⁻ Salmonella or Trp⁻ *Escherichia coli*.

6. A method according to claim 1, wherein the recombinant yeast cells further produce at least one additional human cytochrome P450 molecular species selected from a group of human cytochrome P450 2A6, P450 2C19 and P450 2D6.

7. A method according to claim 1 or 6, wherein the recombinant yeast cells further produce at least one additional human cytochrome P450 molecular species selected from a group of human cytochrome P450 1A1, P450 2B6, P450 2C8 and P450 2C18.

8. An artificial fused enzyme, which comprises human cytochrome P450 3A4 connected with yeast NADPH-P450 reductase.

9. A yeast expression plasmid having a fused gene comprising a gene coding for human P450 3A4 connected with a gene coding for yeast NADPH-P450 reductase.

10. A method of determining in vitro the potential human metabolite of a chemical compound, which comprises:
    (a) reacting the chemical compound with recombinant yeast cells that produce the four human cytochrome P450 molecular species consisting of P450 1A2, P450 2C9, P450 2E1 and P450 3A4 and a yeast NADPH-P450 reductase, wherein said yeast NADPH-P450 reductase is optionally in the form of a fused enzyme with each of said human cytochrome P450 molecular species, or reacting the chemical compound with cell free extracts of the yeast cells; and
    (b) identifying the resulting metabolite.

11. A method according to claim 1, wherein the yeast NADPH-P450 reductase is in the form of a fused enzyme with each of said human cytochrome P450 molecular species.

12. A method according to claim 10, wherein the yeast NADPH-P450 reductase is in the form of a fused enzyme with each of said human cytochrome P450 molecular species.

13. A method according to claim 11, wherein the analyzing step (b) is performed by assay of mutagenicity of the metabolite.

14. A method according to claim 11, wherein the analyzing step (b) is performed by assay of carcinogenicity of the metabolite.

* * * * *